(12) United States Patent
Krepski et al.

(10) Patent No.: US 7,579,359 B2
(45) Date of Patent: Aug. 25, 2009

(54) 1-ALKOXY 1H-IMIDAZO RING SYSTEMS AND METHODS

(75) Inventors: Larry R. Krepski, White Bear Lake, MN (US); Daniel E. Duffy, White Bear Lake Township, MN (US); John F. Gerster, Woodbury, MN (US); Joan T. Moseman, Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 391 days.

(21) Appl. No.: 11/574,463

(22) PCT Filed: Sep. 1, 2005

(86) PCT No.: PCT/US2005/031310
§ 371 (c)(1),
(2), (4) Date: Feb. 28, 2007

(87) PCT Pub. No.: WO2006/028962
PCT Pub. Date: Mar. 16, 2006

(65) Prior Publication Data
US 2009/0005376 A1 Jan. 1, 2009

Related U.S. Application Data

(60) Provisional application No. 60/606,629, filed on Sep. 2, 2004.

(51) Int. Cl.
*A01N 43/42* (2006.01)
*A61K 31/55* (2006.01)
*C07D 471/00* (2006.01)
*C07D 491/00* (2006.01)
*C07D 471/02* (2006.01)

(52) U.S. Cl. .................. 514/293; 514/303; 546/82; 546/118

(58) Field of Classification Search .................. 546/82, 546/118; 514/293, 303
See application file for complete search history.

(56) References Cited

U.S. PATENT DOCUMENTS

| | | |
|---|---|---|
| 3,314,941 A | 4/1967 | Littell et at |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gester |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,446,153 A | 8/1995 | Llindstrom et al. |
| 5,482,936 A | 1/1996 | Lindstrom |
| 5,693,811 A | 12/1997 | Lindstrom |
| 5,741,908 A | 4/1998 | Gerster et al. |
| 5,756,747 A | 5/1998 | Gerster et al. |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,245,776 B1 | 6/2001 | Skwierczynski et al. |
| 6,331,539 B1 | 12/2001 | Crooks et al. |
| 6,376,669 B1 | 4/2002 | Rice et al. |
| 6,451,810 B1 | 9/2002 | Coleman et al. |
| 6,518,265 B1 | 2/2003 | Kato et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |

(Continued)

FOREIGN PATENT DOCUMENTS

| | | |
|---|---|---|
| EP | 0 394 026 | 10/1990 |
| EP | 1 104 764 | 6/2001 |
| JP | 9-208584 | 8/1997 |
| JP | 11-080156 A | 3/1999 |
| JP | 11-222432 | 8/1999 |
| JP | 2000-247884 | 9/2000 |
| WO | WO 02/36592 | 5/2002 |
| WO | WO 2005/018551 | 3/2005 |
| WO | WO 2005/018555 | 3/2005 |
| WO | WO 2005/018556 | 3/2005 |

(Continued)

OTHER PUBLICATIONS

Wozniak et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.

(Continued)

*Primary Examiner*—D. Margaret Seaman
*Assistant Examiner*—Niloofar Rahmani
(74) *Attorney, Agent, or Firm*—Dean A. Ersfeld

(57) ABSTRACT

Imidazo-containing compounds (e.g., imidazonaphthyridines, imidazopyridines, imidazoquinolines, and imidazote-trahydroquinolines) with an alkoxy substituent at the 1-position, pharmaceutical compositions containing the compounds and methods of use of these compounds as immunomodulators, for inducing cytokine biosynthesis in animals and in the treatment of diseases including viral and neoplastic diseases are disclosed.

16 Claims, No Drawings

U.S. PATENT DOCUMENTS

| | | |
|---|---|---|
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,465 B2 | 2/2004 | Dellaria et al. |
| 6,706,728 B2 | 3/2004 | Hedenstrom et al. |
| 6,743,920 B2 | 6/2004 | Lindstrom et al. |
| 6,756,382 B2 | 6/2004 | Coleman et al. |
| 6,797,718 B2 | 9/2004 | Dellaria et al. |
| 6,818,650 B2 | 11/2004 | Griesgraber |
| 6,841,678 B2 | 1/2005 | Merli et al. |
| 6,852,861 B2 | 2/2005 | Merli et al. |
| 7,163,947 B2 | 1/2007 | Griesgraber et al. |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2002/0110840 A1 | 8/2002 | Tomai et al. |
| 2003/0096835 A1 | 5/2003 | Crooks et al. |
| 2003/0130299 A1 | 7/2003 | Crooks et al. |
| 2003/0133913 A1 | 7/2003 | Tomai et al. |
| 2003/0139364 A1 | 7/2003 | Krieg et al. |
| 2003/0144286 A1 | 7/2003 | Frenkel et al. |
| 2003/0161797 A1 | 8/2003 | Miller et al. |
| 2003/0185835 A1* | 10/2003 | Braun .................... 424/184.1 |
| 2003/0199538 A1 | 10/2003 | Skwierczynski et al. |
| 2004/0014779 A1 | 1/2004 | Gorden et al. |
| 2004/0091491 A1 | 5/2004 | Kedl et al. |
| 2004/0132079 A1 | 7/2004 | Gupta et al. |
| 2004/0141950 A1 | 7/2004 | Noelle et al. |
| 2004/0147543 A1 | 7/2004 | Hays et al. |
| 2004/0162309 A1 | 8/2004 | Gorden et al. |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0180919 A1 | 9/2004 | Miller et al. |
| 2004/0181130 A1 | 9/2004 | Miller et al. |
| 2004/0181211 A1 | 9/2004 | Graham et al. |
| 2004/0191833 A1 | 9/2004 | Fink et al. |
| 2004/0192585 A1 | 9/2004 | Owens et al. |
| 2004/0197865 A1 | 10/2004 | Gupta et al. |
| 2004/0202720 A1 | 10/2004 | Wightman et al. |
| 2004/0214851 A1 | 10/2004 | Birmachu et al. |
| 2005/0054590 A1 | 3/2005 | Averett |
| 2005/0085500 A1 | 4/2005 | Gutman et al. |
| 2005/0165236 A1 | 7/2005 | Colombo et al. |
| 2005/0245562 A1 | 11/2005 | Garcia-Echeverria et al. |

FOREIGN PATENT DOCUMENTS

| | | |
|---|---|---|
| WO | WO 2005/020999 | 3/2005 |
| WO | WO 2005/032484 | 4/2005 |
| WO | WO 2005/048933 | 6/2005 |
| WO | WO 2005/048945 | 6/2005 |
| WO | WO 2005/051317 | 6/2005 |
| WO | WO 2005/051324 | 6/2005 |
| WO | WO 2005/054237 | 6/2005 |
| WO | WO 2005/054238 | 6/2005 |
| WO | WO 2005/066169 | 7/2005 |
| WO | WO 2005/066170 | 7/2005 |
| WO | WO 2005/066172 | 7/2005 |
| WO | WO 2005/076783 | 8/2005 |
| WO | WO 2005/079195 | 9/2005 |
| WO | WO 2005/094531 | 10/2005 |
| WO | WO 2005/123079 | 12/2005 |
| WO | WO 2005/123080 | 12/2005 |
| WO | WO 2006/009826 | 1/2006 |
| WO | WO 2006/009832 | 1/2006 |
| WO | WO 2006/026760 | 3/2006 |
| WO | WO 2006/028451 | 3/2006 |
| WO | WO 2006/028545 | 3/2006 |
| WO | WO 2006/028962 | 3/2006 |
| WO | WO 2006/029115 | 3/2006 |
| WO | WO 2006/031878 | 3/2006 |
| WO | WO 2006/038923 | 4/2006 |
| WO | WO 2006/065280 | 6/2006 |
| WO | WO 2006/074003 | 7/2006 |
| WO | WO 2006/074046 | 7/2006 |
| WO | WO 2006/004737 | 8/2006 |
| WO | WO 2006/083400 | 8/2006 |
| WO | WO 2006/083440 | 8/2006 |
| WO | WO 2006/086449 | 8/2006 |
| WO | WO 2006/086633 | 8/2006 |
| WO | WO 2006/091394 | 8/2006 |
| WO | WO 2006/091567 | 8/2006 |
| WO | WO 2006/091568 | 8/2006 |
| WO | WO 2006/091647 | 8/2006 |
| WO | WO 2006/098852 | 9/2006 |
| WO | WO 2006/107771 | 10/2006 |
| WO | WO 2006/107851 | 10/2006 |
| WO | WO 2006/107853 | 10/2006 |
| WO | WO 2006/121528 | 11/2006 |
| WO | WO 2007/028129 | 3/2007 |
| WO | WO 2007/030775 | 3/2007 |
| WO | WO 2007/030777 | 3/2007 |
| WO | WO 2007/035935 | 3/2007 |
| WO | WO 2007/056112 | 5/2007 |

OTHER PUBLICATIONS

Brennan et al., "Automated Bioassay of Interferons in Micro-test Plates.", *Biotechniques*, Jun./Jul., 78, 1983.

Testerman et al., "Cytokine Induction by the Immunomodulators Imiquimod and S-27609.", *Journal of Leukocyte Biology*, vol. 58, pp. 365-372, Sep. 1995.

Bachman et al., "Synthesis of Substituted Quinolylamines. Derivatives of 4-Amino-7-Chloroquinoline.", *J. Org. Chem*, pp. 1278-1284 (1950).

Jain et al., "Chemical and Pharmacological Investigations of Some ω-Substituted Alkylamino-3-aminopyridines.", *J. Med. Chem.*, 11, pp. 87-92 (1968).

Baranov et al., "Pyrazoles, Imidazoles, and Other 5-Membered Rings.", *Chem. Abs.* 85, 94362, (1976).

Berènyi et al., "Ring Transformation of Condensed Dihydro-astriazines.", *J. Heterocyclic Chem.*, 18, pp. 1537-1540 (1981).

Chollet et al., "Development of a Topically Active Imiquimod Formulation.", *Pharmaceutical Development and Technology*, 4(1), pp. 35-43 (1999).

Izumi et al., "1H-Imidazo[4,5-c]quinoline Derivatives as Novel Potent TNF-α Suppressors: Synthesis and Structure-Activity Relationship of 1-, 2- and 4-Substituted 1H-imidazo[4,5-c]pyridines.", *Bioorganic & Medicinal Chemistry*, 11, pp. 2541-2550 (2003).

* cited by examiner

1-ALKOXY 1H-IMIDAZO RING SYSTEMS AND METHODS

RELATED APPLICATION

This application is the National Stage of International Application No. PCT/US2005/031310, filed Sep. 1, 2005, which claims priority to U.S. Provisional Application Ser. No. 60/606629, filed Sep. 2, 2004, which is incorporated herein by reference in its entirety.

BACKGROUND

In the 1950's the 1H-imidazo[4,5-c]quinoline ring system was developed, and 1-(6-methoxy-8-quinolinyl)-2-methyl-1H-imidazo[4,5-c]quinoline was synthesized for possible use as an antimalarial agent. Subsequently, syntheses of various substituted 1H-imidazo[4,5-c]quinolines were reported. For example, 1-[2-(4-piperidyl)ethyl]-1H-imidazo[4,5-c]quinoline was synthesized as a possible anticonvulsant and cardiovascular agent. Also, several 2-oxoimidazo[4,5-c]quinolines have been reported.

Certain 1H-imidazo[4,5-c]quinolin-4-amines and 1- and 2-substituted derivatives thereof were later found to be useful as antiviral agents, bronchodilators and immunomodulators. Subsequently, certain substituted 1H-imidazo[4,5-c]pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds were synthesized and found to be useful as immune response modifiers (IRMs), rendering them useful in the treatment of a variety of disorders.

There continues to be interest in and a need for compounds that have the ability to modulate the immune response, by induction of cytokine biosynthesis or other mechanisms.

SUMMARY OF THE INVENTION

It has now been found that certain 1-alkoxy 1H-imidazo ring systems modulate cytokine biosynthesis. In one aspect, the present invention provides compounds of the Formula I:

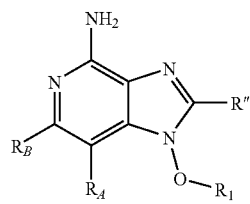

I and more specifically the following compounds of the Formulas II, III, IV, V, VI, VII, VIII, IX, X, XI, XII, XIII, and XIV:

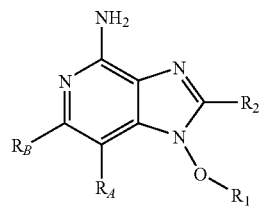

II

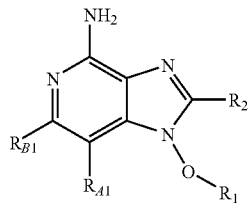

III

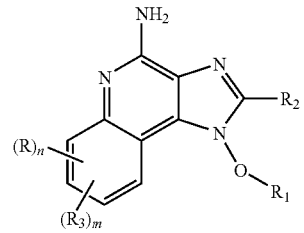

IV

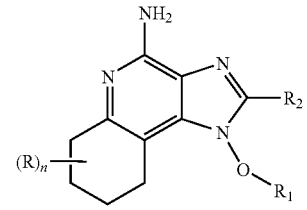

V

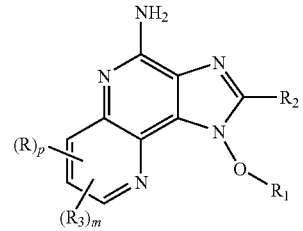

VI

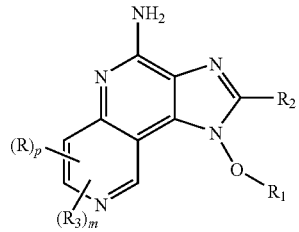

VII

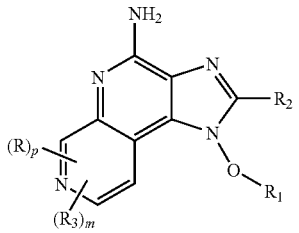

VIII

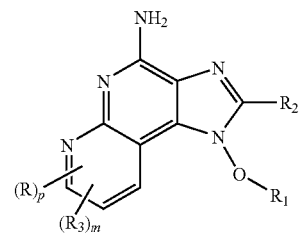

IX

3

-continued

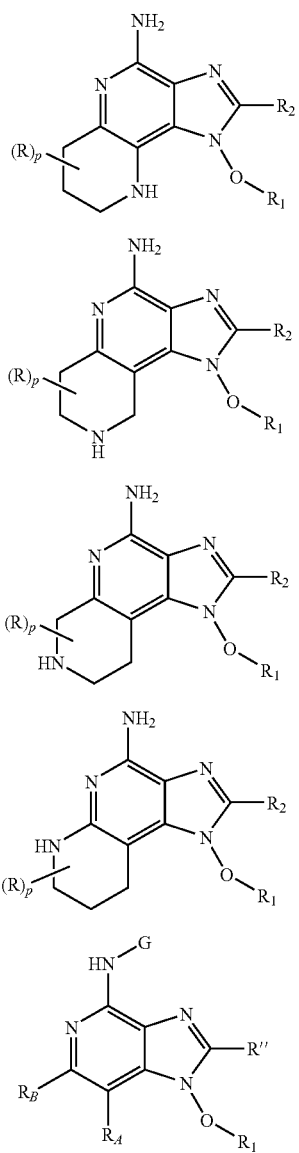

X

XI

XII

XIII

XIV wherein $R_1$, $R_2$, $R_3$, R", R, $R_A$, $R_B$, $R_{A1}$, $R_{B1}$, m, n, p, and G are as defined below; and pharmaceutically acceptable salts thereof.

The compounds of Formulas I, II, III, IV, V, VI, VII, VIII, IX, X, XI, XII, XIII, and XIV are useful as immune response modifiers (IRMs) due to their ability to modulate cytokine biosynthesis (e.g., induce or inhibit the biosynthesis or production of one or more cytokines) and otherwise modulate the immune response when administered to animals. Compounds can be tested per the test procedures described in the Examples Section. Compounds can be tested for induction of cytokine biosynthesis by incubating human peripheral blood mononuclear cells (PBMC) in a culture with the compound(s) at a concentration range of 30 to 0.014 μM and analyzing for interferon (α) or tumor necrosis factor (α) in the culture supernatant. Compounds can be tested for inhibition of cytokine biosynthesis by incubating mouse macrophage cell line Raw 264.7 in a culture with the compound(s) at a single concentration of, for example, 5 μM and analyzing for tumor

4 necrosis factor (α) in the culture supernatant. The ability to modulate cytokine biosynthesis, for example, induce the biosynthesis of one or more cytokines, makes the compounds useful in the treatment of a variety of conditions such as viral diseases and neoplastic diseases, that are responsive to such changes in the immune response.

In another aspect, the present invention provides pharmaceutical compositions containing the immune response modifier compounds, and methods of inducing cytokine biosynthesis in animal cells, treating a viral disease in an animal, and/or treating a neoplastic disease in an animal by administering to the animal one or more compounds of the Formulas I, II, III, IV, V, VI, VII, VIII, IX, X, XI, XII, XIII, and/or XIV, and/or pharmaceutically acceptable salts thereof.

In another aspect, the invention provides methods of synthesizing the compounds of Formulas I, II, III, IV, V, VI, VII, VIII, IX, X, XI, XII, XIII, and XIV and intermediates useful in the synthesis of these compounds.

As used herein, "a," "an," "the," "at least one," and "one or more" are used interchangeably.

The terms "comprising" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. Guidance is also provided herein through lists of examples, which can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formulas I through XIV:

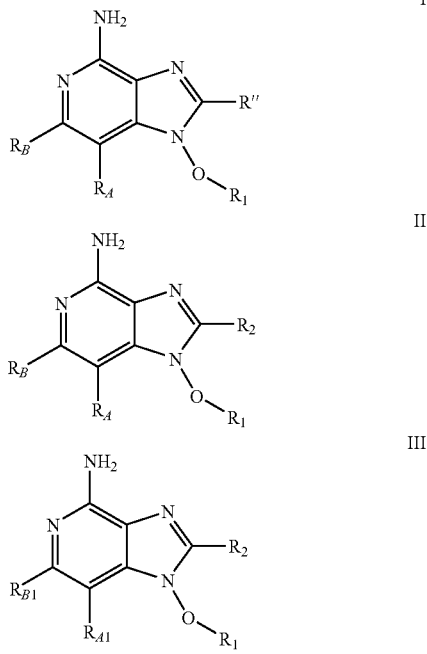

I

II

III

-continued
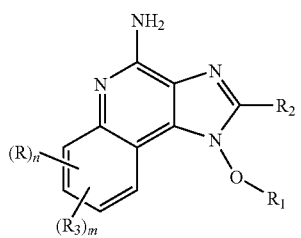
IV
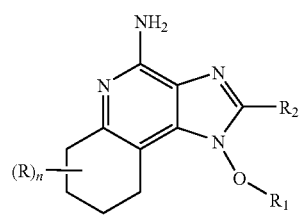
V
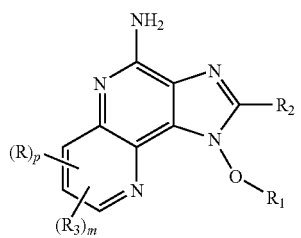
VI
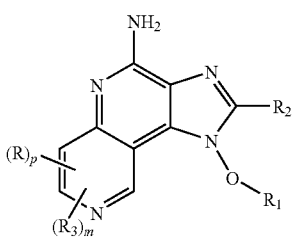
VII
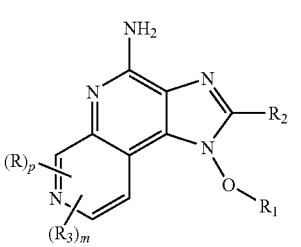
VIII
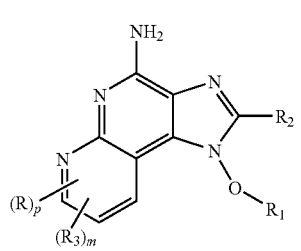
IX
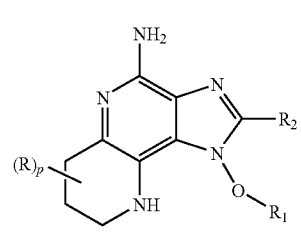
X
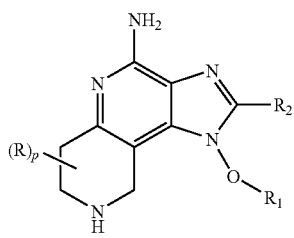
XI
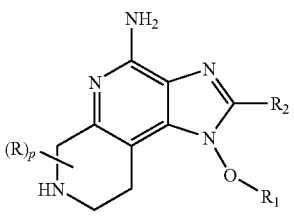
XII
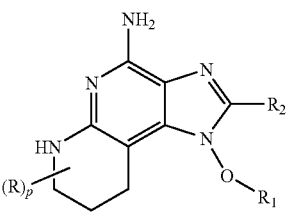
XIII
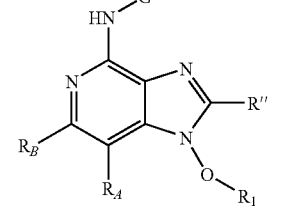
XIV
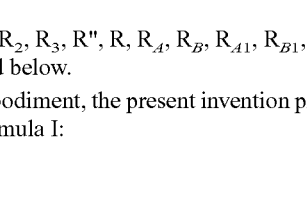
wherein: $R_1$, $R_2$, $R_3$, R", R, $R_A$, $R_B$, $R_{A1}$, $R_{B1}$, m, n, p, and G are as defined below.
In one embodiment, the present invention provides a compound of Formula I:
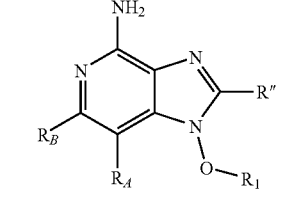
I
wherein:
$R_1$ is selected from the group consisting of:
—$R_4$,
—X—$R_5$,
—X—N($R_6$)—Y—$R_4$,
—X"—C($R_7$)—N($R_9$)—$R_4$,
—X—O—C($R_7$)—N($R_6$)—$R_4$,
—X—S(O)$_2$—N($R_6$)—$R_4$, and
—X—O—$R_4$;

$R_A$ and $R_B$ are each independently selected from the group consisting of:
hydrogen,
halogen,
alkyl,
alkenyl,
alkoxy,
alkylthio, and
—$N(R_{12})_2$;
or when taken together, $R_A$ and $R_B$ form a fused benzene or pyridine ring which is unsubstituted or substituted by one or more R''' groups;
or when taken together, $R_A$ and $R_B$ form a fused cyclohexene or tetrahydropyridine ring which is unsubstituted or substituted by one or more R groups;
R is selected from the group consisting of:
halogen,
hydroxyl,
alkyl,
alkenyl,
haloalkyl,
alkoxy,
alkylthio, and
—$N(R_{12})_2$;
$R_4$ is selected from the group consisting of hydrogen, alkyl, alkenyl, alkynyl, aryl, arylalkylenyl, heteroaryl, and heterocyclyl wherein the alkyl, alkenyl, alkynyl, aryl, arylalkylenyl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when $R_4$ is a substituted alkyl group and the substituent contains a hetero atom which bonds directly to the alkyl group then the alkyl group contains at least two carbons between the substituent and the oxygen atom to which $R_1$ is bonded;
$R_5$ is selected from the group consisting of:

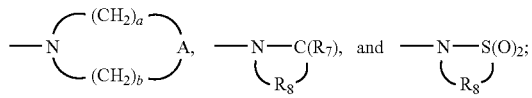

$R_6$ is selected from the group consisting of hydrogen, alkyl, and arylalkylenyl;
$R_7$ is selected from the group consisting of =O and =S;
$R_8$ is $C_{2-7}$ alkylene;
$R_9$ is selected from the group consisting of hydrogen, alkyl, and arylalkylenyl; or $R_9$ and $R_4$ together with the nitrogen atom to which $R_9$ is bonded can join to form the group

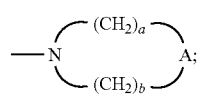

$R_{12}$ is selected from the group consisting of hydrogen and alkyl;
A is selected from the group consisting of —$CH(R_6)$—, —O—, —$N(R_6)$—, —$N(Y—R_4)$—, and —$N(X—N(R_6)—Y—R_4)$—;

X is $C_{2-20}$ alkylene;
X" is $C_{1-20}$ alkylene;
Y is selected from the group consisting of —$C(R_7)$—, —$C(R_7)$—O—, —$S(O)_2$—, —$S(O)_2$—$N(R_6)$—, and —$C(R_7)$—$N(R_9)$—;
a and b are independently integers from 1 to 4 with the proviso that when A is —O—, —$N(R_6)$—, —$N(Y—R_4)$—, or —$N(X—N(R_6)—Y—R_4)$— then a and b are independently integers from 2 to 4;
R" hydrogen or a non-interfering substituent; and
R''' is a non-interfering substituent;

or a pharmaceutically acceptable salt thereof.

In one embodiment, the present invention provides a compound of Formula II:

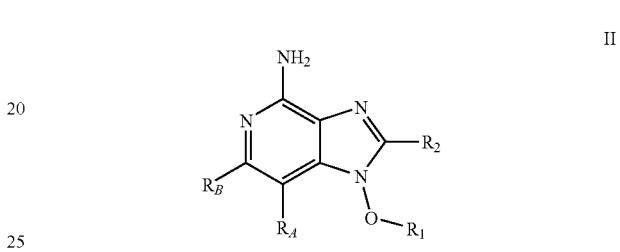

wherein:
$R_1$ is selected from the group consisting of:
—$R_4$,
—X—$R_5$,
—X—$N(R_6)$—Y—$R_4$,
—X"—$C(R_7)$—$N(R_9)$—$R_4$,
—X—O—$C(R_7)$—$N(R_6)$—$R_4$,
—X—$S(O)_2$—$N(R_6)$—$R_4$, and
—X—O—$R_4$;
$R_2$ is selected from the group consisting of:
hydrogen,
alkyl,
alkenyl,
aryl,
heteroaryl,
heterocyclyl,
alkyl-Z-alkylenyl,
aryl-Z-alkylenyl,
alkenyl-Z-alkylenyl, and
alkyl or alkenyl substituted by one or more substituents selected from the group consisting of:
hydroxy,
halogen,
—$N(R_6)_2$,
—$C(R_7)$—$N(R_6)_2$,
—$S(O)_2$—$N(R_6)_2$,
—$N(R_6)$—$C(R_7)$—$C_{1-10}$ alkyl,
—$N(R_6)$—$S(O)_2$—$C_{1-10}$ alkyl,
—$C(O)$—$C_{1-10}$ alkyl,
—$C(O)$—O—$C_{1-10}$ alkyl,
—$N_3$,
aryl,
heteroaryl,
heterocyclyl,
—$C(O)$-aryl,
—$C(O)$-heteroaryl,
—$N(R_6)$—$C(R_7)$-aryl,
—$N(R_6)$—$S(O)_2$-aryl,
—O—$C(R_7)$—$C_{1-10}$ alkyl,
—O—$C(R_7)$-aryl, —O—C(R$_7$)—N(R$_6$)—C$_{1-10}$ alkyl, and
—O—C(R$_7$)—N(R$_6$)-aryl;

R$_A$ and R$_B$ are each independently selected from the group consisting of:
hydrogen,
halogen,
alkyl,
alkenyl,
alkoxy,
alkylthio, and
—N(R$_{12}$)$_2$;

or when taken together, R$_A$ and R$_B$ form a fused benzene or pyridine ring which is unsubstituted or substituted by one or more R groups, or substituted by one R$_3$ group, or substituted by one R$_3$ group and one R group, or substituted by one R$_3$ group and two R groups;

or when taken together, R$_A$ and R$_B$ form a fused cyclohexene or tetrahydropyridine ring which is unsubstituted or substituted by one or more R groups;

R is selected from the group consisting of:
halogen,
hydroxy,
alkyl,
alkenyl,
haloalkyl,
alkoxy,
alkylthio, and
—N(R$_{12}$)$_2$;

R$_3$ is selected from the group consisting of:
-Z'-R$_4$',
-Z'-X'—R$_4$',
-Z'-X'—Y'—R$_4$', and
-Z'-X'—R$_5$';

R$_4$ is selected from the group consisting of hydrogen, alkyl, alkenyl, alkynyl, aryl, arylalkylenyl, heteroaryl, and heterocyclyl wherein the alkyl, alkenyl, alkynyl, aryl, arylalkylenyl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when R$_4$ is a substituted alkyl group and the substituent contains a hetero atom which bonds directly to the alkyl group then the alkyl group contains at least two carbons between the substituent and the oxygen atom to which R$_1$ is bonded;

R$_5$ is selected from the group consisting of:

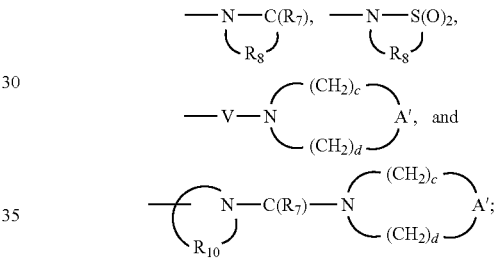

X is C$_{2-20}$ alkylene;
X" is C$_{1-20}$ alkylene;
Y is selected from the group consisting of —C(R$_7$)—, —C(R$_7$)—O—, —S(O)$_2$—, —S(O)$_2$—N(R$_6$)—, and —C(R$_7$)—N(R$_9$)—;
Z is selected from the group consisting of —O— and —S(O)$_{0-2}$—;

A is selected from the group consisting of —CH(R$_6$)—, —O—, —N(R$_6$)—, —N(Y—R$_4$)—, and —N(X—N(R$_6$)—Y—R$_4$)—;

a and b are independently integers from 1 to 4 with the proviso that when A is —O—, —N(R$_6$)—, —N(Y—R$_4$)—, or —N(X—N(R$_6$)—Y—R$_4$)— then a and b are independently integers from 2 to 4;

R$_4$' is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$' is selected from the group consisting of:

X' is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene, or heterocyclylene and optionally interrupted by one or more —O— groups;

Y' is selected from the group consisting of:

Z' is a bond or —O—;

A' is selected from the group consisting of —CH$_2$—, —O—, —C(O)—, —S(O)$_{0-2}$—, and —N(R$_4$')—;

Q is selected from the group consisting of a bond, —C(R$_7$)—, —C(R$_7$)—C(R$_7$)—, —S(O)$_2$—, —C(R$_7$)—N(R$_{11}$)—W—, —S(O)$_2$—N(R$_{11}$)—, —C(R$_7$)—O—, and —C(R$_7$)—N(OR$_{12}$)—;

V is selected from the group consisting of —C(R$_7$)—, —O—C(R$_7$)—, —N(R$_{11}$)—C(R$_7$)—, and —S(O)$_2$—;

W is selected from the group consisting of a bond, —C(O)—, and —S(O)$_2$—;

c and d are independently integers from 1 to 6 with the proviso that c+d is ≦7, and when A' is —O— or —N(R$_4$')— then c and d are independently integers from 2 to 4;

R$_6$ is selected from the group consisting of hydrogen, alkyl, and arylalkylenyl;

R$_7$ is selected from the group consisting of =O and =S;

R$_8$ is C$_{2-7}$ alkylene;

R$_9$ is selected from the group consisting of hydrogen, alkyl, and arylalkylenyl; or R$_9$ and R$_4$ together with the nitrogen atom to which R$_9$ is bonded can join to form the group

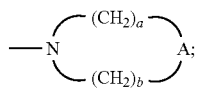

R$_{10}$ is C$_{3-8}$ alkylene;

R$_{11}$ is selected from the group consisting of hydrogen, C$_{1-10}$ alkyl, C$_{2-10}$ alkenyl, C$_{1-10}$ alkoxyC$_{2-10}$ alkylenyl, and arylC$_{1-10}$ alkylenyl; and R$_{12}$ is selected from the group consisting of hydrogen and alkyl;

or a pharmaceutically acceptable salt thereof.

In one embodiment, the present invention provides a compound of Formula III:

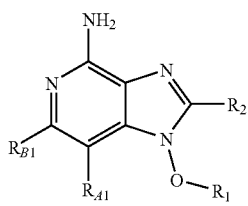

III wherein:

R$_1$ is selected from the group consisting of:
—R$_4$,
—X—R$_5$,
—X—N(R$_6$)—Y—R$_4$,
—X"—C(R$_7$)—N(R$_9$)—R$_4$,
—X—O—C(R$_7$)—N(R$_6$)—R$_4$,
—X—S(O)$_2$—N(R$_6$)—R$_4$, and
—X—O—R$_4$;

R$_2$ is selected from the group consisting of:
hydrogen,
alkyl,
alkenyl,
aryl,
heteroaryl,
heterocyclyl,
alkyl-Z-alkylenyl,
aryl-Z-alkylenyl,
alkenyl-Z-alkylenyl, and
alkyl or alkenyl substituted by one or more substituents selected from the group consisting of:
hydroxy,
halogen,
—N(R$_6$)$_2$,
—C(R$_7$)—N(R$_6$)$_2$,
—S(O)$_2$—N(R$_6$)$_2$,
—N(R$_6$)—C(R$_7$)—C$_{1-10}$ alkyl,
—N(R$_6$)—S(O)$_2$—C$_{1-10}$ alkyl,
—C(O)—C$_{1-10}$ alkyl,
—C(O)—O—C$_{1-10}$ alkyl,
—N$_3$,
aryl,
heteroaryl,
heterocyclyl,
—C(O)-aryl,
—C(O)-heteroaryl,
—N(R$_6$)—C(R$_7$)-aryl,
—N(R$_6$)—S(O)$_2$-aryl,
—O—C(R$_7$)—C$_{1-10}$ alkyl,
—O—C(R$_7$)-aryl,
—O—C(R$_7$)—N(R$_6$)—C$_{1-10}$ alkyl, and
—O—C(R$_7$)—N(R$_6$)-aryl;

R$_{A1}$ and R$_{B1}$ are each independently selected from the group consisting of:
hydrogen,
halogen,
alkyl,
alkenyl,
alkoxy,
alkylthio, and
—N(R$_{12}$)$_2$;

R$_4$ is selected from the group consisting of hydrogen, alkyl, alkenyl, alkynyl, aryl, arylalkylenyl, heteroaryl, and heterocyclyl wherein the alkyl, alkenyl, alkynyl, aryl, arylalkylenyl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when R$_4$ is a substituted alkyl group and the substituent contains a hetero atom which bonds directly to the alkyl group then the alkyl group contains at least two carbons between the substituent and the oxygen atom to which R$_1$ is bonded;

R$_5$ is selected from the group consisting of:

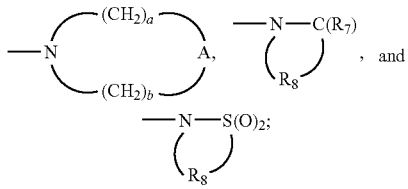

R$_6$ is selected from the group consisting of hydrogen, alkyl, and arylalkylenyl;

R$_7$ is selected from the group consisting of =O and =S;

R$_8$ is C$_{2-7}$ alkylene;

$R_9$ is selected from the group consisting of hydrogen, alkyl, and arylalkylenyl; or $R_9$ and $R_4$ together with the nitrogen atom to which $R_9$ is bonded can join to form the group

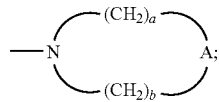

$R_{12}$ is selected from the group consisting of hydrogen and alkyl;

A is selected from the group consisting of —CH($R_6$)—, —O—, —N($R_6$)—, —N(Y—$R_4$)—, and —N(X—N($R_6$)—Y—$R_4$)—;

X is $C_{2-20}$ alkylene;

X" is $C_{1-20}$ alkylene;

Y is selected from the group consisting of —C($R_7$)—, —C($R_7$)—O—, —S(O)$_2$—, —S(O)$_2$—N($R_6$)—, and —C($R_7$)—N($R_9$)—;

Z is selected from the group consisting of —O— and —S(O)$_{0-2}$—; and a and b are independently integers from 1 to 4 with the proviso that when A is —O—, —N($R_6$)—, —N(Y—$R_4$)—, or —N(X—N($R_6$)—Y—$R_4$)— then a and b are independently integers from 2 to 4;

or a pharmaceutically acceptable salt thereof.

In one embodiment, the present invention provides a compound of Formula IV:

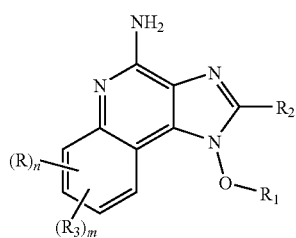

IV wherein:

$R_1$ is selected from the group consisting of:
—$R_4$,
—X—$R_5$,
—X—N($R_6$)—Y—$R_4$,
—X"—C($R_7$)—N($R_9$)—$R_4$,
—X—O—C($R_7$)—N($R_6$)—$R_4$,
—X—S(O)$_2$—N($R_6$)—$R_4$, and
—X—O—$R_4$;

$R_2$ is selected from the group consisting of:
hydrogen,
alkyl,
alkenyl,
aryl,
heteroaryl,
heterocyclyl,
alkyl-Z-alkylenyl,
aryl-Z-alkylenyl,
alkenyl-Z-alkylenyl, and
alkyl or alkenyl substituted by one or more substituents selected from the group consisting of:
hydroxy,
halogen,
—N($R_6$)$_2$,
—C($R_7$)—N($R_6$)$_2$,
—S(O)$_2$—N($R_6$)$_2$,
—N($R_6$)—C($R_7$)—$C_{1-10}$ alkyl,
—N($R_6$)—S(O)$_2$—$C_{1-10}$ alkyl,
—C(O)—$C_{1-10}$ alkyl,
—C(O)—O—$C_{1-10}$ alkyl,
—$N_3$,
aryl,
heteroaryl,
heterocyclyl,
—C(O)-aryl,
—C(O)-heteroaryl,
—N($R_6$)—C($R_7$)-aryl,
—N($R_6$)—S(O)$_2$-aryl,
—O—C($R_7$)—$C_{1-10}$ alkyl,
—O—C($R_7$)-aryl,
—O—C($R_7$)—N($R_6$)—$C_{1-10}$ alkyl, and
—O—C($R_7$)—N($R_6$)-aryl;

R is selected from the group consisting of:
halogen,
hydroxyl,
alkyl,
alkenyl,
haloalkyl,
alkoxy,
alkylthio, and
—N($R_{12}$)$_2$;

$R_3$ is selected from the group consisting of:
-Z'-$R_4$',
-Z'-X'—$R_4$',
-Z'-X'—Y'—$R_4$', and
-Z'-X'—$R_5$';

n is an integer from 0 to 4;

m is 0 or 1, with the proviso that when m is 1, n is 0, 1, or 2;

$R_4$ is selected from the group consisting of hydrogen, alkyl, alkenyl, alkynyl, aryl, arylalkylenyl, heteroaryl, and heterocyclyl wherein the alkyl, alkenyl, alkynyl, aryl, arylalkylenyl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when $R_4$ is a substituted alkyl group and the substituent contains a hetero atom which bonds directly to the alkyl group then the alkyl group contains at least two carbons between the substituent and the oxygen atom to which $R_1$ is bonded;

$R_5$ is selected from the group consisting of:

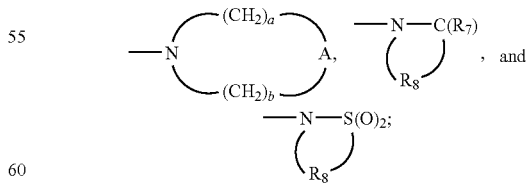

, and

X is $C_{2-20}$ alkylene;

X" is $C_{1-20}$ alkylene;

Y is selected from the group consisting of —C($R_7$)—, —C($R_7$)—O—, —S(O)$_2$—, —S(O)$_2$—N($R_6$)—, and —C($R_7$)—N($R_9$)—;

Z is selected from the group consisting of —O— and —S(O)$_{0-2}$—;

A is selected from the group consisting of —CH(R$_6$)—, —O—, —N(R$_6$)—, —N(Y—R$_4$)—, and —N(X—N(R$_6$)—Y—R$_4$)—;

a and b are independently integers from 1 to 4 with the proviso that when A is —O—, —N(R$_6$)—, —N(Y—R$_4$)—, or —N(X—N(R$_6$)—Y—R$_4$)— then a and b are independently integers from 2 to 4;

R$_4$' is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$' is selected from the group consisting of:

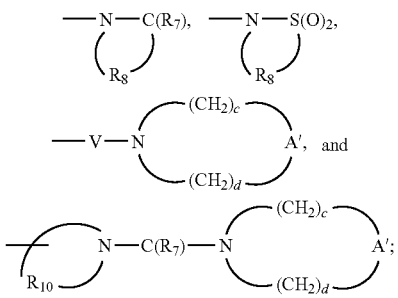

X' is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene, or heterocyclylene and optionally interrupted by one or more —O— groups;

Y' is selected from the group consisting of:

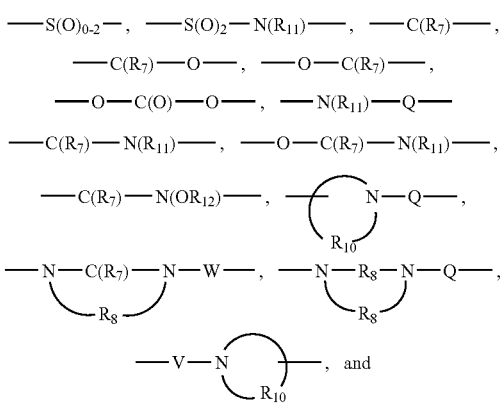

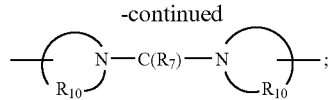

Z' is a bond or —O—;

A' is selected from the group consisting of —CH$_2$—, —O—, —C(O)—, —S(O)$_{0-2}$—, and —N(R$_4$')—;

Q is selected from the group consisting of a bond, —C(R$_7$)—, —C(R$_7$)—C(R$_7$)—, —S(O)$_2$—, —C(R$_7$)—N(R$_{11}$)—W—, —S(O)$_2$—N(R$_{11}$)—, —C(R$_7$)—O—, and —C(R$_7$)—N(OR$_{12}$)—;

V is selected from the group consisting of —C(R$_7$)—, —O—C(R$_7$)—, —N(R$_{11}$)—C(R$_7$)—, and —S(O)$_2$—;

W is selected from the group consisting of a bond, —C(O)—, and —S(O)$_2$—;

c and d are independently integers from 1 to 6 with the proviso that c+d is ≦7, and when A' is —O— or —N(R$_4$')— then c and d are independently integers from 2 to 4;

R$_6$ is selected from the group consisting of hydrogen, alkyl, and arylalkylenyl;

R$_7$ is selected from the group consisting of =O and =S;

R$_8$ is C$_{2-7}$ alkylene;

R$_9$ is selected from the group consisting of hydrogen, alkyl, and arylalkylenyl; or R$_9$ and R$_4$ together with the nitrogen atom to which R$_9$ is bonded can join to form the group

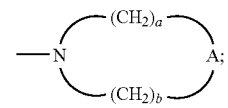

R$_{10}$ is C$_{3-8}$ alkylene;

R$_{11}$ is selected from the group consisting of hydrogen, C$_{1-10}$ alkyl, C$_{2-10}$ alkenyl, C$_{1-10}$ alkoxyC$_{2-10}$ alkylenyl, and arylC$_{1-10}$ alkylenyl; and R$_{12}$ is selected from the group consisting of hydrogen and alkyl;

or a pharmaceutically acceptable salt thereof.

In one embodiment, the present invention provides a compound of Formula V:

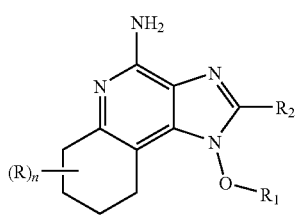

wherein:
R$_1$ is selected from the group consisting of:
—R$_4$,
—X—R$_5$,
—X—N(R$_6$)—Y—R$_4$,
—X''—C(R$_7$)—N(R$_9$)—R$_4$,
—X—O—C(R$_7$)—N(R$_6$)—R$_4$,
—X—S(O)$_2$—N(R$_6$)—R$_4$, and
—X—O—R$_4$;

$R_2$ is selected from the group consisting of:
hydrogen,
alkyl,
alkenyl,
aryl,
heteroaryl,
heterocyclyl,
alkyl-Z-alkylenyl,
aryl-Z-alkylenyl,
alkenyl-Z-alkylenyl, and
alkyl or alkenyl substituted by one or more substituents selected from the group consisting of:
hydroxy,
halogen,
—N($R_6$)$_2$,
—C($R_7$)—N($R_6$)$_2$,
—S(O)$_2$—N($R_6$)$_2$,
—N($R_6$)—C($R_7$)—$C_{1-10}$ alkyl,
—N($R_6$)—S(O)$_2$—$C_{1-10}$ alkyl,
—C(O)—$C_{1-10}$ alkyl,
—C(O)—O—$C_{1-10}$ alkyl,
—$N_3$,
aryl,
heteroaryl,
heterocyclyl,
—C(O)-aryl,
—C(O)-heteroaryl,
—N($R_6$)—C($R_7$)-aryl,
—N($R_6$)—S(O)$_2$-aryl,
—O—C($R_7$)—$C_{1-10}$ alkyl,
—O—C($R_7$)-aryl,
—O—C($R_7$)—N($R_6$)—$C_{1-10}$ alkyl, and
—O—C($R_7$)—N($R_6$)-aryl;
R is selected from the group consisting of:
halogen,
hydroxy,
alkyl,
alkenyl,
haloalkyl,
alkoxy,
alkylthio, and
—N($R_{12}$)$_2$;
n is an integer from 0 to 4;
$R_4$ is selected from the group consisting of hydrogen, alkyl, alkenyl, alkynyl, aryl, arylalkylenyl, heteroaryl, and heterocyclyl wherein the alkyl, alkenyl, alkynyl, aryl, arylalkylenyl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when $R_4$ is a substituted alkyl group and the substituent contains a hetero atom which bonds directly to the alkyl group then the alkyl group contains at least two carbons between the substituent and the oxygen atom to which $R_1$ is bonded;
$R_5$ is selected from the group consisting of:

$$\overset{(CH_2)_a}{\underset{(CH_2)_b}{-N\diagup\phantom{xx}\diagdown}A,}\quad \overset{-N-C(R_7)}{\underset{R_8}{(\phantom{xx})}}, \text{ and}$$

-continued
$$-\underset{R_8}{N}-S(O)_2;$$

$R_6$ is selected from the group consisting of hydrogen, alkyl, and arylalkylenyl;
$R_7$ is selected from the group consisting of =O and =S;
$R_8$ is $C_{2-7}$ alkylene;
$R_9$ is selected from the group consisting of hydrogen, alkyl, and arylalkylenyl; or
$R_9$ and $R_4$ together with the nitrogen atom to which $R_9$ is bonded can join to form the group $$-\underset{(CH_2)_b}{N\diagup\phantom{xx}\diagdown}A;$$

$R_{12}$ is selected from the group consisting of hydrogen and alkyl;
A is selected from the group consisting of —CH($R_6$)—, —O—, —N($R_6$)—, —N(Y—$R_4$)—, and —N(X—N($R_6$)—Y—$R_4$)—;
X is $C_{2-20}$ alkylene;
X" is $C_{1-20}$ alkylene;
Y is selected from the group consisting of —C($R_7$)—, —C($R_7$)—O—, —S(O)$_2$—, —S(O)$_2$—N($R_6$)—, and —C($R_7$)—N($R_9$)—;
Z is selected from the group consisting of —O— and —S(O)$_{0-2}$—; and
a and b are independently integers from 1 to 4 with the proviso that when A is —O—, —N($R_6$)—, —N(Y—$R_4$)—, or —N(X—N($R_6$)—Y—$R_4$)— then a and b are independently integers from 2 to 4;
or a pharmaceutically acceptable salt thereof.

In some embodiments, the present invention provides a compound selected from the group consisting of the following Formulas VI, VII, VIII, and IX (preferably, a compound of Formula VI):

VI

VII

-continued

VIII

[Structure VIII: imidazo-naphthyridine with NH2, R2, O-R1, (R)p, (R3)m substituents]

IX

[Structure IX: imidazo-naphthyridine with NH2, R2, O-R1, (R)p, (R3)m substituents]

wherein:

$R_1$ is selected from the group consisting of:
—$R_4$,
—X—$R_5$,
—X—N($R_6$)—Y—$R_4$,
—X"—C($R_7$)—N($R_9$)—$R_4$,
—X—O—C($R_7$)—N($R_6$)—$R_4$,
—X—S(O)$_2$—N($R_6$)—$R_4$, and
—X—O—$R_4$;

$R_2$ is selected from the group consisting of:
hydrogen,
alkyl,
alkenyl,
aryl,
heteroaryl,
heterocyclyl,
alkyl-Z-alkylenyl,
aryl-Z-alkylenyl,
alkenyl-Z-alkylenyl, and
alkyl or alkenyl substituted by one or more substituents selected from the group consisting of:
hydroxy,
halogen,
—N($R_6$)$_2$,
—C($R_7$)—N($R_6$)$_2$,
—S(O)$_2$—N($R_6$)$_2$,
—N($R_6$)—C($R_7$)—$C_{1-10}$ alkyl,
—N($R_6$)—S(O)$_2$—$C_{1-10}$ alkyl,
—C(O)—$C_{1-10}$ alkyl,
—C(O)—O—$C_{1-10}$ alkyl,
—$N_3$,
aryl,
heteroaryl,
heterocyclyl,
—C(O)-aryl,
—C(O)-heteroaryl,
—N($R_6$)—C($R_7$)-aryl,
—N($R_6$)—S(O)$_2$-aryl,
—O—C($R_7$)—$C_{1-10}$ alkyl,
—O—C($R_7$)-aryl,
—O—C($R_7$)—N($R_6$)—$C_{1-10}$ alkyl, and
—O—C($R_7$)—N($R_6$)-aryl;

R is selected from the group consisting of:
halogen,
hydroxyl,
alkyl,
alkenyl,
haloalkyl,
alkoxy,
alkylthio, and
—N($R_{12}$)$_2$;

$R_3$ is selected from the group consisting of:
-Z'-$R_4$',
-Z'-X'—$R_4$',
-Z'-X'—Y'—$R_4$', and
-Z'-X'—$R_5$';

p is an integer from 0 to 3;
m is 0 or 1, with the proviso that when m is 1, p is 0, 1, or 2;

$R_4$ is selected from the group consisting of hydrogen, alkyl, alkenyl, alkynyl, aryl, arylalkylenyl, heteroaryl, and heterocyclyl wherein the alkyl, alkenyl, alkynyl, aryl, arylalkylenyl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when $R_4$ is a substituted alkyl group and the substituent contains a hetero atom which bonds directly to the alkyl group then the alkyl group contains at least two carbons between the substituent and the oxygen atom to which $R_1$ is bonded;

$R_5$ is selected from the group consisting of:

[Structures showing ring systems with (CH2)a, (CH2)b, A, N—C(R7), R8, and N—S(O)2, R8]

X is $C_{2-20}$ alkylene;
X" is $C_{1-20}$ alkylene;
Y is selected from the group consisting of —C($R_7$)—, —C($R_7$)—O—, —S(O)$_2$—, —S(O)$_2$—N($R_6$)—, and —C($R_7$)—N($R_9$)—;
Z is selected from the group consisting of —O— and —S(O)$_{0-2}$—;
A is selected from the group consisting of —CH($R_6$)—, —O—, —N($R_6$)—, —N(Y—$R_4$)—, and —N(X—N($R_6$)—Y—$R_4$)—;
a and b are independently integers from 1 to 4 with the proviso that when A is —O—, —N($R_6$)—, —N(Y—$R_4$)—, or —N(X—N($R_6$)—Y—$R_4$)— then a and b are independently integers from 2 to 4;

$R_4$' is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5'$ is selected from the group consisting of:

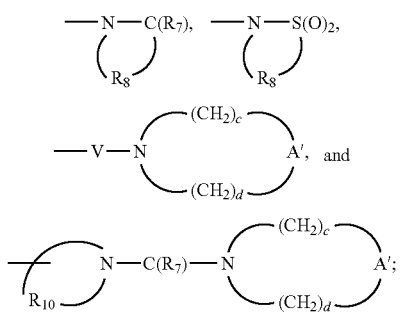

X' is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene, or heterocyclylene and optionally interrupted by one or more —O— groups;

Y' is selected from the group consisting of:

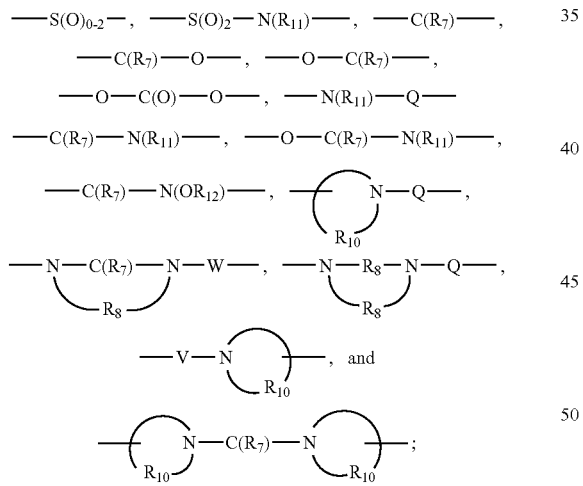

Z' is a bond or —O—;

A' is selected from the group consisting of —CH$_2$—, —O—, —C(O)—, —S(O)$_{0-2}$—, and —N(R$_4'$)—;

Q is selected from the group consisting of a bond, —C(R$_7$)—, —C(R$_7$)—C(R$_7$)—, —S(O)$_2$—, —C(R$_7$)—N(R$_{11}$)—W—, —S(O)$_2$—N(R$_{11}$)—, —C(R$_7$)—O—, and —C(R$_7$)—N(OR$_{12}$)—;

V is selected from the group consisting of —C(R$_7$)—, —O—C(R$_7$)—, —N(R$_{11}$)—C(R$_7$)—, and —S(O)$_2$—;

W is selected from the group consisting of a bond, —C(O)—, and —S(O)$_2$—;

c and d are independently integers from 1 to 6 with the proviso that c+d is ≦7, and when A' is —O— or —N(R$_4'$)— then c and d are independently integers from 2 to 4;

$R_6$ is selected from the group consisting of hydrogen, alkyl, and arylalkylenyl;

$R_7$ is selected from the group consisting of =O and =S;

$R_8$ is C$_{2-7}$ alkylene;

$R_9$ is selected from the group consisting of hydrogen, alkyl, and arylalkylenyl; or $R_9$ and $R_4$ together with the nitrogen atom to which $R_9$ is bonded can join to form the group

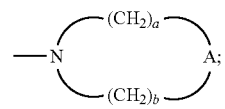

$R_{10}$ is C$_{3-8}$ alkylene;

$R_{11}$ is selected from the group consisting of hydrogen, C$_{1-10}$ alkyl, C$_{2-10}$ alkenyl, C$_{1-10}$ alkoxyC$_{2-10}$ alkylenyl, and arylC$_{1-10}$ alkylenyl; and $R_{12}$ is selected from the group consisting of hydrogen and alkyl;

or a pharmaceutically acceptable salt thereof.

In some embodiments, the present invention provides a compound selected from the group consisting of the following Formulas X, XI, XII, and XIII:

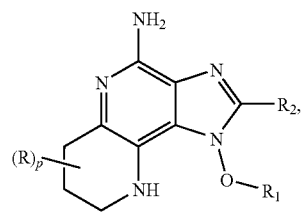

X

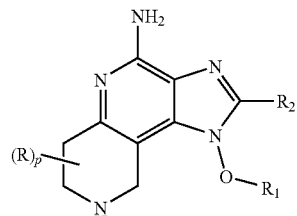

XI

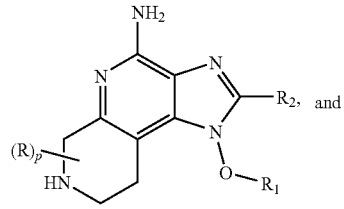

XII

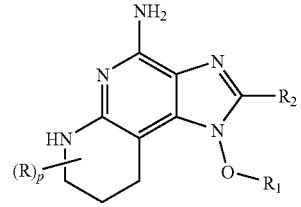

XIII wherein:
R₁ is selected from the group consisting of:
—R₄,
—X—R₅,
—X—N(R₆)—Y—R₄,
—X"—C(R₇)—N(R₉)—R₄,
—X—O—C(R₇)—N(R₆)—R₄,
—X—S(O)₂—N(R₆)—R₄, and
—X—O—R₄;
R₂ is selected from the group consisting of:
hydrogen,
alkyl,
alkenyl,
aryl,
heteroaryl,
heterocyclyl,
alkyl-Z-alkylenyl,
aryl-Z-alkylenyl,
alkenyl-Z-alkylenyl, and
alkyl or alkenyl substituted by one or more substituents selected from the group consisting of:
hydroxy,
halogen,
—N(R₆)₂,
—C(R₇)—N(R₆)₂,
—S(O)₂—N(R₆)₂,
—N(R₆)—C(R₇)—C₁₋₁₀ alkyl,
—N(R₆)—S(O)₂—C₁₋₁₀ alkyl,
—C(O)—C₁₋₁₀ alkyl,
—C(O)—O—C₁₋₁₀ alkyl,
—N₃,
aryl,
heteroaryl,
heterocyclyl,
—C(O)-aryl,
—C(O)-heteroaryl,
—N(R₆)—C(R₇)-aryl,
—N(R₆)—S(O)₂-aryl,
—O—C(R₇)—C₁₋₁₀ alkyl,
—O—C(R₇)-aryl,
—O—C(R₇)—N(R₆)—C₁₋₁₀ alkyl, and
—O—C(R₇)—N(R₆)-aryl;
R is selected from the group consisting of:
halogen,
hydroxy,
alkyl,
alkenyl,
haloalkyl,
alkoxy,
alkylthio, and
—N(R₁₂)₂;
p is an integer from 0 to 3;
R₄ is selected from the group consisting of hydrogen, alkyl, alkenyl, alkynyl, aryl, arylalkylenyl, heteroaryl, and heterocyclyl wherein the alkyl, alkenyl, alkynyl, aryl, arylalkylenyl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when R₄ is a substituted alkyl group and the substituent contains a hetero atom which bonds directly to the alkyl group then the alkyl group contains at least two carbons between the substituent and the oxygen atom to which R₁ is bonded;
R₅ is selected from the group consisting of:

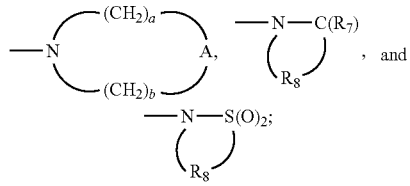

R₆ is selected from the group consisting of hydrogen, alkyl, and arylalkylenyl;
R₇ is selected from the group consisting of =O and =S;
R₈ is C₂₋₇ alkylene;
R₉ is selected from the group consisting of hydrogen, alkyl, and arylalkylenyl; or
R₉ and R₄ together with the nitrogen atom to which R₉ is bonded can join to form the group

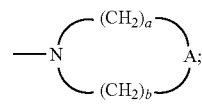

R₁₂ is selected from the group consisting of hydrogen and alkyl;
A is selected from the group consisting of —CH(R₆)—, —O—, —N(R₆)—, —N(Y—R₄)—, and —N(X—N(R₆)—Y—R₄)—;
X is C₂₋₂₀ alkylene;
X" is C₁₋₂₀ alkylene;
Y is selected from the group consisting of —C(R₇)—, —C(R₇)—O—, —S(O)₂—, —S(O)₂—N(R₆)—, and —C(R₇)—N(R₉)—;
Z is selected from the group consisting of —O— and —S(O)₀₋₂—; and
a and b are independently integers from 1 to 4 with the proviso that when A is —O—, —N(R₆)—, —N(Y—R₄)—, or —N(X—N(R₆)—Y—R₄)— then a and b are independently integers from 2 to 4;
or a pharmaceutically acceptable salt thereof.
In one embodiment, the present invention provides a compound of Formula XIV:

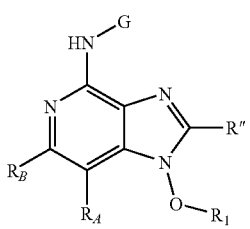

wherein:
G is selected from the group consisting of:
—C(O)—R',
α-aminoacyl,
α-aminoacyl-α-aminoacyl,
—C(O)—O—R', —C(O)—N(R'''')—R',
—C(=NY$_2$)—R',
—CH(OH)—C(O)—OY$_2$,
—CH(OC$_{1-4}$ alkyl)Y$_0$,
—CH$_2$Y$_1$, or
—CH(CH$_3$)Y$_1$;

wherein:

R' and R'''' are each independently C$_{1-10}$ alkyl, C$_{3-7}$ cycloalkyl, phenyl, or benzyl, each of which may be unsubstituted or substituted by one or more substituents selected from the group consisting of halogen, hydroxy, nitro, cyano, carboxy, C$_{1-6}$ alkyl, C$_{1-4}$ alkoxy, aryl, heteroaryl, arylC$_{1-4}$ alkylenyl, heteroarylC$_{1-4}$ alkylenyl, haloC$_{1-4}$ alkyl, haloC$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$;

α-aminoacyl is an acyl group derived from an amino acid selected from the group consisting of racemic, D-, and L-amino acids;

Y$_2$ is selected from the group consisting of hydrogen, C$_{1-6}$ alkyl, and benzyl;

Y$_0$ is selected from the group consisting of C$_{1-6}$ alkyl, carboxyC$_{1-6}$ alkyl, aminoC$_{1-4}$ alkyl, mono-N—C$_{1-6}$ alkylaminoC$_{1-4}$ alkyl, and di-N,N—C$_{1-6}$ alkylaminoC$_{1-4}$ alkyl;

Y$_1$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl.

R$_1$ is selected from the group consisting of:
—R$_4$,
—X—R$_5$,
—X—N(R$_6$)—Y—R$_4$,
—X''—C(R$_7$)—N(R$_9$)—R$_4$,
—X—O—C(R$_7$)—N(R$_6$)—R$_4$,
—X—S(O)$_2$—N(R$_6$)—R$_4$, and
—X—O—R$_4$;

R$_A$ and R$_B$ are each independently selected from the group consisting of:
hydrogen,
halogen,
alkyl,
alkenyl,
alkoxy,
alkylthio, and
—N(R$_{12}$)$_2$;

or when taken together, R$_A$ and R$_B$ form a fused benzene or pyridine ring which is unsubstituted or substituted by one or more R''' groups;

or when taken together, R$_A$ and R$_B$ form a fused cyclohexene or tetrahydropyridine ring which is unsubstituted or substituted by one or more R groups;

R is selected from the group consisting of:
halogen,
hydroxyl,
alkyl,
alkenyl,
haloalkyl,
alkoxy,
alkylthio, and
—N(R$_{12}$)$_2$;

R$_4$ is selected from the group consisting of hydrogen, alkyl, alkenyl, alkynyl, aryl, arylalkylenyl, heteroaryl, and heterocyclyl wherein the alkyl, alkenyl, alkynyl, aryl, arylalkylenyl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when R$_4$ is a substituted alkyl group and the substituent contains a hetero atom which bonds directly to the alkyl group then the alkyl group contains at least two carbons between the substituent and the oxygen atom to which R$_1$ is bonded;

R$_5$ is selected from the group consisting of:

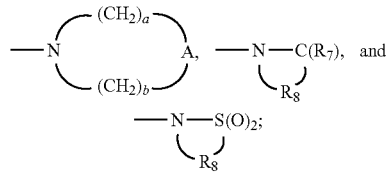

R$_6$ is selected from the group consisting of hydrogen, alkyl, and arylalkylenyl;

R$_7$ is selected from the group consisting of =O and =S;

R$_8$ is C$_{2-7}$ alkylene;

R$_9$ is selected from the group consisting of hydrogen, alkyl, and arylalkylenyl; or R$_9$ and R$_4$ together with the nitrogen atom to which R$_9$ is bonded can join to form the group

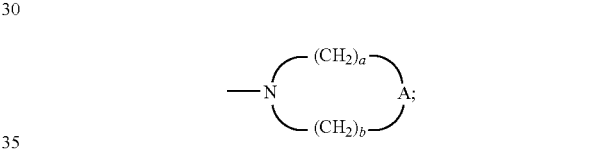

R$_{12}$ is selected from the group consisting of hydrogen and alkyl;

A is selected from the group consisting of —CH(R$_6$)—, —O—, —N(R$_6$)—, —N(Y—R$_4$)—, and —N(X—N(R$_6$)—Y—R$_4$)—;

X is C$_{2-20}$ alkylene;

X'' is C$_{1-20}$ alkylene;

Y is selected from the group consisting of —C(R$_7$)—, —C(R$_7$)—O—, —S(O)$_2$—, —S(O)$_2$—N(R$_6$)—, and —C(R$_7$)—N(R$_9$)—;

a and b are independently integers from 1 to 4 with the proviso that when A is —O—, —N(R$_6$)—, —N(Y—R$_4$)—, or —N(X—N(R$_6$)—Y—R$_4$)— then a and b are independently integers from 2 to 4;

R'' hydrogen or a non-interfering substituent; and

R''' is a non-interfering substituent; or a pharmaceutically acceptable salt thereof.

For any of the compounds presented herein, each one of the following variables (e.g., R, R'', R''', R$_1$, R$_2$, R$_3$, R$_4$', R$_A$, R$_B$, m, n, p, A, G, and so on) in any of its embodiments can be combined with any one or more of the other variables in any of their embodiments as would be understood by one of skill in the art. Each of the resulting combinations of variables is an embodiment of the present invention.

For certain embodiments, each of R'' and R''' is independently a non-interfering substituent. For certain embodiments, each R'' is independently selected from the group consisting of hydrogen and non-interfering substituents. Herein, "non-interfering" means that the immunomodulator activity (for example, the ability to induce the biosynthesis of one or more cytokines or the ability to inhibit the biosynthesis of one or more cytokines) of the compound, which includes a non-interfering substituent, is not destroyed. Illustrative R‴ groups include those described herein for $R_2$. Illustrative R‴ groups include those described herein for R and $R_3$.

For certain embodiments, $R_A$ and $R_B$ are each independently selected from the group consisting of: hydrogen, halogen, alkyl, alkenyl, alkoxy, alkylthio, and —N($R_{12}$)$_2$; or when taken together, $R_A$ and $R_B$ form a fused benzene or pyridine ring which is unsubstituted or substituted by one or more R‴ groups; or when taken together, $R_A$ and $R_B$ form a fused cyclohexene or tetrahydropyridine ring which is unsubstituted or substituted by one or more R groups.

For certain embodiments, $R_A$ and $R_B$ are each independently selected from the group consisting of: hydrogen, halogen, alkyl, alkenyl, alkoxy, alkylthio, and —N($R_{12}$)$_2$; or when taken together, $R_A$ and $R_B$ form a fused benzene or pyridine ring which is unsubstituted or substituted by one or more R groups, or substituted by one $R_3$ group, or substituted by one $R_3$ group and one R group, or substituted by one $R_3$ group and two R groups; or when taken together, $R_A$ and $R_B$ form a fused cyclohexene or tetrahydropyridine ring which is unsubstituted or substituted by one or more R groups.

For certain embodiments, $R_A$ and $R_B$ are each independently selected from the group consisting of: hydrogen, halogen, alkyl, alkenyl, alkoxy, alkylthio, and —N($R_{12}$)$_2$. For certain embodiments, $R_A$ and $R_B$ are each independently selected from hydrogen and alkyl. For certain embodiments, $R_A$ and $R_B$ are each methyl. For certain embodiments, $R_A$ and $R_B$ form a fused benzene or pyridine ring which is unsubstituted or substituted by one or more R‴ groups. For certain embodiments, $R_A$ and $R_B$ form a fused benzene or pyridine ring which is unsubstituted or substituted by one or more R groups, or substituted by one $R_3$ group, or substituted by one $R_3$ group and one R group, or substituted by one $R_3$ group and two R groups.

For certain embodiments, $R_A$ and $R_B$ form a fused benzene ring. For certain of these embodiments, the fused benzene ring is unsubstituted.

For certain embodiments, $R_A$ and $R_B$ form a fused pyridine ring. For certain of these embodiments, the fused pyridine ring is

wherein the highlighted bond indicates the position where the ring is fused. For certain of these embodiments, the fused pyridine ring is unsubstituted.

For certain embodiments, $R_A$ and $R_B$ form a fused cyclohexene or tetrahydropyridine ring which is unsubstituted or substituted by one or more R groups. For certain embodiments, $R_A$ and $R_B$ form a fused cyclohexene ring. For certain of these embodiments, the fused cyclohexene ring is unsubstituted.

For certain embodiments, $R_A$ and $R_B$ form a fused tetrahydropyridine ring. For certain of these embodiments, the fused tetrahydropyridine ring is

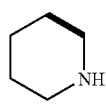

wherein the highlighted bond indicates the position where the ring is fused. For certain of these embodiments, the fused tetrahydropyridine ring is unsubstituted.

As used herein, the fused cyclohexene ring and fused tetrahydropyridine ring are each fused to the ring system such that the unsaturated carbon atoms of each of these rings are in common with the pyridine ring. A fused cyclohexene ring is illustrated within the following formulas:

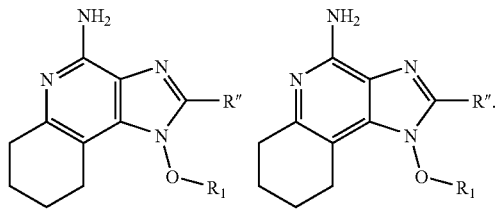

A fused tetrahydropyridine ring is illustrated within the following formulas:

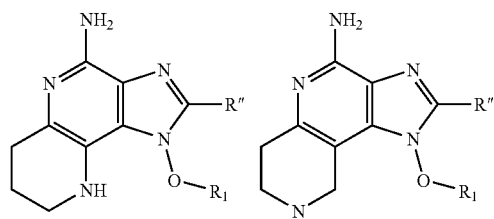

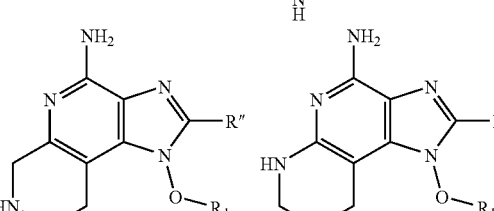

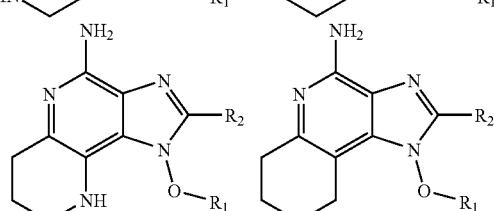

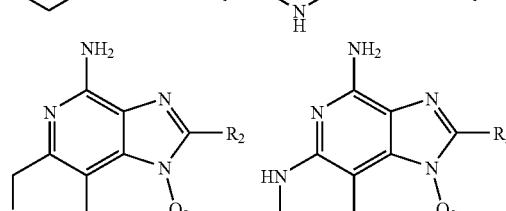

For certain embodiments, $R_{A1}$ and $R_{B1}$ are each independently selected from the group consisting of: hydrogen, halogen, alkyl, alkenyl, alkoxy, alkylthio, and —N($R_{12}$)$_2$. For certain embodiments, $R_{A1}$ and $R_{B1}$ are each independently selected from hydrogen and alkyl. For certain embodiments, $R_{A1}$ and $R_{B1}$ are each methyl.

For certain embodiments, R is selected from the group consisting of: halogen, hydroxyl, alkyl, alkenyl, haloalkyl, alkoxy, alkylthio, and —N($R_{12}$)$_2$.

For certain embodiments, $R_1$ is selected from the group consisting of:
—$R_4$, —X—$R_5$, —X—N($R_6$)—Y—$R_4$, —X"—C($R_7$)—N($R_9$)—$R_4$, —X"—C($R_7$)—O—N($R_6$)—$R_4$, —X—S(O)$_2$—N($R_6$)—$R_4$, and —X—O—$R_4$. For certain embodiments, $R_1$ is —$R_4$, —X—N($R_6$)—Y—$R_4$, or —X"—C($R_7$)—N($R_9$)—$R_4$.

For certain embodiments, $R_1$ is —$R_4$. For certain of these embodiments, —$R_4$ is alkyl, aryl, or arylalkylenyl.

For certain embodiments, $R_1$ is selected from the group consisting of hydrogen, methyl, ethyl, n-propyl, isopropyl, n-butyl, tert-butyl, isobutyl, cyclohexyl, benzyl, phenyl, 3-phenylpropyl, 2-nitrobenzyl, 2-phenoxyethyl, and (pyridin-3-yl)methyl. For certain of these embodiments, $R_1$ is (and, hence, $R_4$ is) methyl, ethyl, n-propyl, n-butyl, isobutyl, cyclohexyl, phenyl, 3-phenylpropyl, or (pyridin-3-yl)methyl. For certain embodiments, $R_1$ is selected from the group consisting of hydrogen, methyl, ethyl, isopropyl, tert-butyl, isobutyl, benzyl, 2-nitrobenzyl, and 2-phenoxyethyl.

For certain embodiments, $R_1$ is —X—N($R_6$)—Y—$R_4$ or —X"—C($R_7$)—N($R_9$)—$R_4$.

For certain embodiments, $R_1$ is 3-[(methanesulfonyl)amino]propyl, 3-(acetylamino)propyl, 3-[(isopropylcarbonyl)amino]propyl, 3-[(cyclohexylcarbonyl)amino]propyl, 3-[(morpholin-4-ylcarbonyl)amino]propyl, 3-{[(isopropylamino)carbonyl]amino}propyl, 2-(morpholin-4-yl)-2-oxoethyl, or carbamoylmethyl.

For certain embodiments, $R_1$ is 3-[(methanesulfonyl)amino]propyl, 3-(acetylamino)propyl, 3-[(isopropylcarbonyl)amino]propyl, 3-[(cyclohexylcarbonyl)amino]propyl, 3-[(morpholin-4-ylcarbonyl)amino]propyl, 3-{[(isopropylamino)carbonyl]amino}propyl, or 2-(morpholin-4-yl)-2-oxoethyl.

For certain embodiments, $R_1$ is methyl, ethyl, n-propyl, isopropyl, n-butyl, isobutyl, cyclohexyl, benzyl, phenyl, 3-phenylpropyl, (pyridin-3-yl)methyl, 3-[(methanesulfonyl)amino]propyl, 3-(acetylamino)propyl, 3-[(isopropylcarbonyl)amino]propyl, 3-[(cyclohexylcarbonyl)amino]propyl, 3-[(morpholin-4-ylcarbonyl)amino]propyl, 3-{[(isopropylamino)carbonyl]amino}propyl, or 2-(morpholin-4-yl)-2-oxoethyl.

For certain embodiments, $R_2$ is selected from the group consisting of: hydrogen, alkyl, alkenyl, aryl, heteroaryl, heterocyclyl, alkyl-Z-alkylenyl, aryl-Z-alkylenyl, alkenyl-Z-alkylenyl, and alkyl or alkenyl substituted by one or more substituents selected from the group consisting of: hydroxy, halogen, —N($R_6$)$_2$, —C($R_7$)—N($R_6$)$_2$, —S(O)$_2$—N($R_6$)$_2$, —N($R_6$)—C($R_7$)—$C_{1-10}$ alkyl, —N($R_6$)—S(O)$_2$—$C_{1-10}$ alkyl, —C(O)—$C_{1-10}$ alkyl, —C(O)—O—$C_{1-10}$ alkyl, —N$_3$, aryl, heteroaryl, heterocyclyl, —C(O)-aryl, —C(O)-heteroaryl, —N($R_6$)—C($R_7$)-aryl, —N($R_6$)—S(O)$_2$-aryl, —O—C($R_7$)—$C_{1-10}$ alkyl, —O—C($R_7$)-aryl, —O—C($R_7$)—N($R_6$)—$C_{1-10}$ alkyl, and —O—C($R_7$)—N($R_6$)-aryl.

For certain embodiments, $R_2$ is selected from the group consisting of hydrogen, alkyl, hydroxyalkyl, alkoxyalkylenyl, heterocyclyl arylalkylenyl, and aryl. For certain embodiments, $R_2$ is selected from the group consisting of hydrogen, alkyl, hydroxyalkyl, and alkoxyalkylenyl.

For certain embodiments, $R_2$ is selected from the group consisting of hydrogen, methyl, ethyl, n-propyl, isopropyl, isopropenyl, n-butyl, sec-butyl, tert-butyl, methoxymethyl, ethoxymethyl, 2-methoxyethyl, hydroxymethyl, 1-hydroxyethyl, 2-hydroxyethyl, 2-hydroxy-1-methylethyl, 3-hydroxypropyl, cyclohexyl, cyclopentyl, tetrahydropyran-4-yl, tetrahydrofuran-3-yl, and phenyl. For certain embodiments, $R_2$ is selected from the group consisting of hydrogen, methyl, ethyl, n-propyl, n-butyl, methoxymethyl, ethoxymethyl, 2-methoxyethyl, hydroxymethyl, 2-hydroxyethyl, and 3-hydroxypropyl. For certain embodiments, $R_2$ is selected from the group consisting of hydrogen, methyl, ethyl, n-propyl, isopropyl, n-butyl, ethoxymethyl, hydroxymethyl, and phenyl.

For certain embodiments, $R_2$ is hydrogen, methyl, ethyl, n-propyl, n-butyl, methoxymethyl, ethoxymethyl, 2-methoxyethyl, hydroxymethyl, 2-hydroxyethyl, 3-hydroxypropyl, isopropyl, sec-butyl, tert-butyl, isopropenyl, cyclopentyl, cyclohexyl, 1-hydroxyethyl, 2-hydroxy-1-methylethyl, tetrahydrofuran-3-yl, or tetrahydropyran-4-yl.

For certain embodiments, $R_3$ is selected from the group consisting of: -Z'-$R_4$', -Z'-X'—$R_4$', -Z'-X'—Y'—$R_4$', and -Z'-X'—$R_5$'. For certain embodiments, $R_3$ is -Z'-$R_4$', or -Z'-X'—Y'—$R_4$'. For certain embodiments, $R_3$ is -Z'-$R_4$'. For certain embodiments, $R_3$ is phenyl or pyridin-3-yl.

For certain embodiments, $R_4$ is selected from the group consisting of hydrogen, alkyl, alkenyl, alkynyl, aryl, arylalkylenyl, heteroaryl, and heterocyclyl wherein the alkyl, alkenyl, alkynyl, aryl, arylalkylenyl, heteroaryl, and heterocyclyl groups can be unsubstituted or substituted by one or more substituents independently selected from the group consisting of alkyl, alkoxy, halo alkyl, halo alkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when $R_4$ is a substituted alkyl group and the substituent contains a hetero atom which bonds directly to the alkyl group then the alkyl group contains at least two carbons between the substituent and the oxygen atom to which $R_1$ is bonded.

For certain embodiments, $R_4$ is selected from the group consisting of hydrogen, alkyl, alkenyl, alkynyl, aryl, heteroaryl, and heterocyclyl wherein the alkyl, alkenyl, alkynyl, aryl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when $R_4$ is a substituted alkyl group and the substituent contains a hetero atom which bonds directly to the alkyl group then the alkyl group contains at least two carbons between the substituent and the oxygen atom to which $R_1$ is bonded.

For certain embodiments, $R_4$ is alkyl, aryl, or arylalkylenyl. For certain of these embodiments, $R_4$ is methyl.

For certain embodiments, $R_4$' is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo.

For certain embodiments, $R_5$ is selected from the group consisting of:

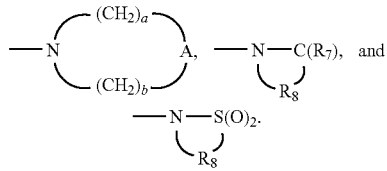

For certain embodiments, $R_5'$ is selected from the group consisting of:

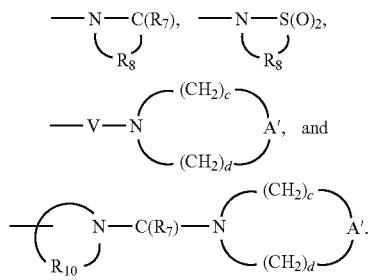

For certain embodiments, $R_6$ is selected from the group consisting of hydrogen, alkyl, and arylalkylenyl. For certain embodiments, $R_6$ is hydrogen.

For certain embodiments, $R_7$ is selected from the group consisting of =O and =S. For certain embodiments, $R_7$ is =O.

For certain embodiments, $R_8$ is $C_{2-7}$ alkylene.

For certain embodiments, $R_9$ is selected from the group consisting of hydrogen, alkyl, and arylalkylenyl. For certain embodiments, $R_9$ is hydrogen.

For certain embodiments, $R_9$ and $R_4$ together with the nitrogen atom to which $R_9$ is bonded can join to form the group

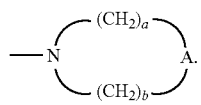

For certain embodiments, A is —O— and a and b are each the integer 2.

For certain embodiments, $R_{10}$ is $C_{3-8}$ alkylene.

For certain embodiments, $R_{11}$ is selected from the group consisting of hydrogen, $C_{1-10}$ alkyl, $C_{2-10}$ alkenyl, $C_{1-10}$ alkoxyC$_{2-10}$ alkylenyl, and arylC$_{1-10}$ alkylenyl.

For certain embodiments, $R_{12}$ is selected from the group consisting of hydrogen and alkyl.

For certain embodiments, A is selected from the group consisting of: —CH($R_6$)—, —O—, —N($R_6$)—, —N(Y—$R_4$)—, and —N(X—N($R_6$)—Y—$R_4$)—. For certain embodiments, A is —O—, —N($R_6$)—, —N(Y—$R_4$)—, or —N(X—N($R_6$)—Y—$R_4$)—.

For certain embodiments, A' is selected from the group consisting of —CH$_2$—, —O—, —C(O)—, —S(O)$_{0-2}$—, and —N($R_4'$)—. For certain embodiments, A' is —O— or —N($R_4'$)—.

For certain embodiments, Q is selected from the group consisting of a bond, —C($R_7$)—, —C($R_7$)—C($R_7$)—, —S(O)$_2$—, —C($R_7$)—N($R_{11}$)—W—, —S(O)$_2$—N($R_{11}$)—, —C($R_7$)—O—, and —C($R_7$)—N(O$R_{12}$)—.

For certain embodiments, V is selected from the group consisting of —C($R_7$)—, —O—C($R_7$)—, —N($R_{11}$)—C($R_7$)—, and —S(O)$_2$—.

For certain embodiments, W is selected from the group consisting of a bond, —C(O)—, and —S(O)$_2$—.

For certain embodiments, X is $C_{2-20}$ alkylene. For certain embodiments, X is $C_{2-4}$ alkylene.

For certain embodiments, X' is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene, or heterocyclylene and optionally interrupted by one or more —O— groups.

For certain embodiments, X" is $C_{1-20}$ alkylene. For certain embodiments, X" is $C_{1-4}$ alkylene.

For certain embodiments, Y is selected from the group consisting of —C($R_7$)—, —C($R_7$)—O—, —S(O)$_2$—, —S(O)$_2$—N($R_6$)—, and —C($R_7$)—N($R_9$)—. For certain embodiments, Y is —C($R_7$)—, —S(O)$_2$—, or —C($R_7$)—N($R_9$)—. For certain of these embodiments, $R_7$ is =O. For certain of these embodiments, $R_9$ is hydrogen.

For certain embodiments, Y' is selected from the group consisting of: —S(O)$_{0-2}$—, —S(O)$_2$—N($R_{11}$)—, —C($R_7$)—, —C($R_7$)—O—, —O—C($R_7$)—, —O—C(O)—O—, —N($R_{11}$)-Q-, —C($R_7$)—N($R_{11}$)—, —O—C($R_7$)—N($R_{11}$)—, —C($R_7$)—N(O$R_{12}$)—,

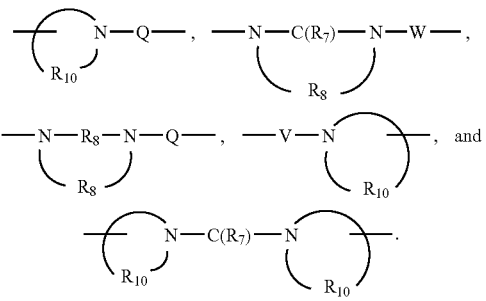

For certain embodiments, Z is selected from the group consisting of —O— and —S(O)$_{0-2}$—.

For certain embodiments, Z' is a bond or —O—. For certain embodiments, Z' is a bond.

For certain embodiments, a and b are independently integers from 1 to 4. For certain embodiments, when A is —O—, —N($R_6$)—, —N(Y—$R_4$)—, or —N(X—N($R_6$)—Y—$R_4$)— then a and b are independently integers from 2 to 4.

For certain embodiments, c and d are independently integers from 1 to 6. For certain embodiments, c+d is ≦7. For certain embodiments, A' is —O— and c and d are independently integers from 2 to 4. For certain embodiments, A' is —N($R_4'$)— and c and d are independently integers from 2 to 4.

For certain embodiments, m is 0 or 1. For certain embodiments, m is 0. For certain embodiments, m is 1. For certain embodiments, when m is 1, n is 0, 1, or 2. For certain embodiments, when m is 1, p is 0, 1, or 2.

For certain embodiments, m is 1 and n is 0.
For certain embodiments, m is 1 and n is 1.
For certain embodiments, m is 1 and n is 2.
For certain embodiments, m is 1 and p is 0.

For certain embodiments, m is 1 and p is 1.

For certain embodiments, m is 1 and p is 2.

For certain embodiments, n is an integer from 0 to 4. For certain embodiments, n is 0. For certain embodiments, n is 0, 1, or 2.

For certain embodiments, p is an integer from 0 to 3. For certain embodiments, p is 0. For certain embodiments, p is 0, 1, or 2.

For certain embodiments, m is 0 and n is 0.

For certain embodiments, m is 0 and p is 0.

For certain embodiments of the compounds of Formulas I through XIII, the —$NH_2$ group can be replaced by an —NH-G group, as shown in the compound of Formula XIV, to form prodrugs. In such embodiments, G is selected from the group consisting of: —C(O)—R', α-aminoacyl, α-aminoacyl-α-aminoacyl, —C(O)—O—R', —C(O)—N(R"")—R', —C(=$NY_2$)—R', —CH(OH)—C(O)—$OY_2$, —CH($OC_{1-4}$ alkyl)$Y_0$, —$CH_2Y_1$, and —CH($CH_3$)$Y_1$. For certain of these embodiments, R' and R"" are each independently $C_{1-10}$ alkyl, $C_{3-7}$ cycloalkyl, phenyl, or benzyl, each of which may be unsubstituted or substituted by one or more substitutents selected from the group consisting of halogen, hydroxy, nitro, cyano, carboxy, $C_{1-6}$ alkyl, $C_{1-4}$ alkoxy, aryl, heteroaryl, aryl$C_{1-4}$ alkylenyl, heteroaryl$C_{1-4}$ alkylenyl, halo$C_{1-4}$ alkyl, halo$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —S(O)$_2$—$NH_2$. For certain embodiments, α-aminoacyl is an acyl group derived from an amino acid selected from the group consisting of racemic, D-, and L-amino acids. For certain embodiments, $Y_2$ is selected from the group consisting of hydrogen, $C_{1-6}$ alkyl, and benzyl. For certain embodiments, $Y_0$ is selected from the group consisting of $C_{1-6}$ alkyl, carboxy$C_{1-6}$ alkyl, amino$C_{1-4}$ alkyl, mono-N—$C_{1-6}$ alkylamino$C_{1-4}$ alkyl, and di-N,N—$C_{1-6}$ alkylamino$C_{1-4}$ alkyl. For certain embodiments, $Y_1$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl.

As used herein, the terms "alkyl", "alkenyl", "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene," "-alkylene-", "alkenylene", "-alkenylene-", "alkynylene", and "-alkynylene-" are the divalent forms of the "alkyl", "alkenyl", and "alkynyl" groups defined above. The terms "alkylenyl", "alkenylenyl", and "alkynylenyl" are used when "alkylene", "alkenylene", and "alkynylene", respectively, are substituted. For example, an arylalkylenyl group comprises an "alkylene" moiety to which an aryl group is attached.

The term "haloalkyl" is inclusive of alkyl groups that are substituted by one or more halogen atoms, including perfluorinated groups. This is also true of other groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

The term "heteroatom" refers to the atoms O, S, or N.

The term "heteroaryl" includes aromatic rings or ring systems that contain at least one ring heteroatom (e.g., O, S, N).

In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2 to 12 carbon atoms, 1 to 3 rings, 1 to 4 heteroatoms, and O, S, and N as the heteroatoms. Exemplary heterocyclic groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicyclic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene", "heteroarylene", and "heterocyclylene" are the divalent forms of the "aryl", "heteroaryl", and "heterocyclyl" groups defined above. The terms "arylenyl," "heteroarylenyl," and "heterocyclylenyl" are used when "arylene", "heteroarylene", and "heterocyclylene", respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula —N($R_{12}$)$_2$ each $R_{12}$ group is independently selected. In another example, when an $R_1$ and an $R_2$ group both contain an $R_6$ group, each $R_6$ group is independently selected. In a further example, when more than one

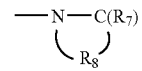

group is present (i.e., $R_5$ and $R_5$' both contain a

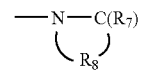

group) each $R_8$ group is independently selected and each $R_7$ group is independently selected.

The invention is inclusive of the compounds described herein (including intermediates) in any of their pharmaceutically acceptable forms, including isomers (e.g., diastereomers and enantiomers), salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

The term "prodrug" means a compound that can be transformed in vivo to yield an immune response modifying compound in any of the salt, solvated, polymorphic, or isomeric forms described above. The prodrug, itself, may be an immune response modifying compound in any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

Conventional methods and techniques of separation and purification can be used to isolate compounds of the invention, as well as various, pharmaceutically acceptable salts thereof and intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

Compounds of the invention can be prepared according to Reaction Scheme I wherein R, $R_1$, $R_2$, and n are as defined above.

In step (1) of Reaction Scheme I, a 4-chloro-3-nitroquinoline of Formula XX is reduced to provide a 3-amino-4-chloroquinoline of Formula XXI. The reduction can be carried out using a conventional heterogeneous hydrogenation catalyst such as platinum on carbon or palladium on carbon. For some compounds of Formula XX, for example, compounds in which R is halogen, a platinum catalyst is preferred. The reaction can be conveniently carried out on a Parr apparatus in a suitable solvent such as toluene and/or isopropanol. Many compounds of Formula XX are known or can be prepared using known synthetic methods, see for example, U.S. Pat. Nos. 4,689,338; 5,175,296; 5,367,076; and 5,389,640; and the documents cited therein. Some compounds of Formula XXI are known. For example, 3-amino-4-chloroquinoline, 3-amino-4,5-dichloroquinoline, and 3-amino-4,7-dichloroquinoline have been prepared by Surrey et al., *Journal of the American Chemical Society*, 73, pp. 2413-2416 (1951).

Other reduction processes may be used for the reduction in step (1). For example, an aqueous solution of sodium dithionite can be added to a solution or suspension of the compound of Formula XX in a suitable solvent such as ethanol or isopropanol. The reaction can be carried out at an elevated temperature, for example, at reflux, or at ambient temperature.

In step (2) of Reaction Scheme I, a 3-amino-4-chloroquinoline of Formula XXI is reacted with an acyl halide of Formula $R_2C(O)Cl$ or $R_2C(O)Br$ to provide an N-(4-chloroquinolin-3-yl) amide of Formula XXII. The acyl halide is added to a solution of a compound of Formula XXI in a suitable solvent such as anhydrous dichloromethane optionally in the presence of a base such as triethylamine. The reaction can be run at a reduced temperature, for example, 0° C., or at ambient temperature. For compounds wherein $R_2$ is hydrogen, the compound of Formula XXI can be reacted with a formylating agent such as, for example, diethoxymethyl acetate. Alternatively, compounds wherein $R_2$ is hydrogen can be prepared utilizing amidines such as N'-(4-chloroquinolin-3-yl)-N,N-dimethylimidoformamide.

In step (3) of Reaction Scheme I, an N-(4-chloroquinolin-3-yl)amide of Formula XXII is reacted with a hydroxylamine hydrochloride of Formula $R_1ONH_2.HCl$ and cyclized to provide a 1H-imidazo[4,5-c]quinoline of Formula XXIII. The hydroxylamine hydrochloride is added to a solution of a compound of Formula XXII in an alcoholic solvent. The reaction can be carried out at an elevated temperature, for example, at reflux. For example, the compound of Formula XXII and the hydroxylamine are refluxed in ethanol. Some hydroxylamine hydrochlorides of Formula $R_1ONH_2.HCl$ are commercially available, others can be prepared using known synthetic methods.

In step (4) of Reaction Scheme I, a 1H-imidazo[4,5-c] quinoline of Formula XXIII is oxidized to provide an N-oxide of Formula XXIV using a conventional oxidizing agent that is capable of forming N-oxides. The reaction is carried out by treating a solution of a compound of Formula XXIII in a suitable solvent such as chloroform or dichloromethane with 3-chloroperoxybenzoic acid at ambient temperature.

In step (5) of Reaction Scheme I, an N-oxide of Formula XXIV is aminated to provide a 1H-imidazo[4,5-c]quinolin-4-amine of the Formula XXV, which is a subgenus of compounds of Formulas I, II, and IV. Step (5) can be carried out by the activation of an N-oxide of Formula XXIV by conversion to an ester and then reacting the ester with an aminating agent. Suitable activating agents include alkyl- or arylsulfonyl chlorides (e.g., benzenesulfonyl chloride, methanesulfonyl chloride, and p-toluenesulfonyl chloride). Suitable aminating agents include ammonia (e.g. in the form of ammonium hydroxide) and ammonium salts (e.g., ammonium carbonate, ammonium bicarbonate, ammonium phosphate). The reaction can be carried out by dissolving a compound of Formula XXIV in a suitable solvent such as chloroform, adding ammonium hydroxide to the solution, and then adding benzenesulfonyl chloride. The product or a pharmaceutically acceptable salt thereof can be isolated using conventional methods.

Alternatively, the oxidation of step (4) and the amination of step (5) can be carried out sequentially without isolating the product of the oxidation to provide a 1H-imidazo[4,5-c]quinolin-4-amine of the Formula XXV. In step (4), after the 1H-imidazo[4,5-c]quinoline of Formula XXIII is consumed by reaction with 3-chloroperoxybenzoic acid as described in step (4), the aminating and acylating agents are added to the reaction mixture as in step (5). The product or a pharmaceutically acceptable salt thereof can be isolated using conventional methods.

Alternatively, step (5) can be carried out by the reaction of an N-oxide of Formula XXIV with trichloroacetyl isocyanate followed by hydrolysis of the resulting intermediate to provide a 1H-imidazo[4,5-c]quinolin-4-amine of the Formula XXV. The reaction is conveniently carried out in two steps by (i) adding trichloroacetyl isocyanate to a solution of the N-oxide of Formula XXIV in a solvent such as dichloromethane and stirring at ambient temperature to provide an isolable amide intermediate. In step (ii), a solution of the intermediate in methanol is treated with a base such as sodium methoxide at ambient temperature. The product or a pharmaceutically acceptable salt thereof can be isolated using conventional methods.

Compounds of the invention can be prepared according to Reaction Scheme II where R, $R_1$, $R_2$, and m are as defined above; E is carbon (imidazoquinoline ring) or nitrogen (imidazonaphthyridine ring); n is an integer from 0 to 4 (imidazoquinoline ring) or 0 to 3 (imidazonaphthyridine ring) with the proviso that when m is 1, n is 0 or 1; and D is —Br, —I, or —OCH$_2$Ph; wherein Ph is phenyl. In step (1) of Reaction Scheme II, an aniline or aminopyridine of Formula XXVI is treated with the condensation product generated from 2,2-dimethyl-1,3-dioxane-4,6-dione (Meldrum's acid) and triethyl orthoformate to provide an imine of Formula XXVII. The reaction is conveniently carried out by adding a solution of an aniline or aminopyridine of Formula XXVI to a heated mixture of Meldrum's acid and triethyl orthoformate and heating the reaction at an elevated temperature. Many anilines and aminopyridines of Formula XXVI are commercially available; others can be prepared by known synthetic methods. For example, benzyloxypyridines of Formula XXVI can be prepared using the method of Holladay et al., *Biorg. Med. Chem. Lett.*, 8, pp. 2797-2802, (1998).

In step (2) of Reaction Scheme II, an imine of Formula XXVII undergoes thermolysis and cyclization to provide a [1,5]naphthyridin-4-ol or a quinolin-4-ol of Formula XXVIII. The reaction is conveniently carried out in a medium such as DOWTHERM A heat transfer fluid at a temperature between 200 and 250° C.

In step (3) of Reaction Scheme II, a [1,5]naphthyridin-4-ol or a quinolin-4-ol of Formula XXVIII is nitrated under conventional nitration conditions to provide a 3-nitro[1,5]naphthyridin-4-ol or 3-nitroquinolin-4-ol of Formula XXIX. The reaction is conveniently carried out by adding nitric acid to a compound of Formula XXVIII in a suitable solvent such as propionic acid and heating the mixture at an elevated temperature.

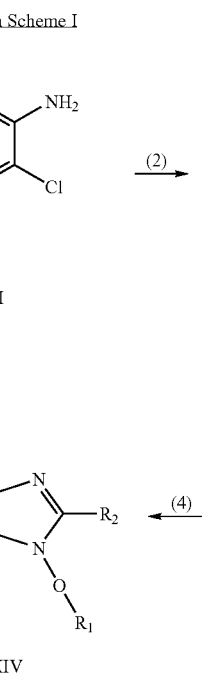

Reaction Scheme I

In step (4) of Reaction Scheme II, a 3-nitro[1,5]naphthyridin-4-ol or 3-nitroquinolin-4-ol of Formula XXIX is reduced to provide a 3-amino[1,5]naphthyridin-4-ol or 3-aminoquinolin-4-ol of Formula XXX. The reduction can be carried out using the methods described in step (1) of Reaction Scheme I.

In step (5) of Reaction Scheme II, a 3-amino[1,5]naphthyridin-4-ol or 3-aminoquinolin-4-ol of Formula XXX is chlorinated using conventional chlorination chemistry to provide a 3-amino-4-chloro[1,5]naphthyridine or 3-amino-4-chloroquinoline of Formula XXXI. The reaction is conveniently carried out by treating a compound of Formula XXX with phosphorous oxychloride in a suitable solvent such as N,N-dimethylformamide (DMF). The reaction can be carried out at ambient temperature or at an elevated temperature such as 100° C.

In step (6) of Reaction Scheme II, a 3-amino-4-chloro[1,5]naphthyridine or 3-amino-4-chloroquinoline of Formula XXXI is reacted with an acyl halide of Formula $R_2C(O)Cl$ or $R_2C(O)Br$ to provide an N-(4-chloro[1,5]naphthyridin-3-yl)amide or N-(4-chloroquinolin-3-yl)amide of Formula XXXII. The reaction can be carried out using the method described in step (2) of Reaction Scheme I.

In step (7) of Reaction Scheme II, an N-(4-chloro[1,5]naphthyridin-3-yl)amide or N-(4-chloroquinolin-3-yl)amide of Formula XXXII is reacted with a hydroxylamine hydrochloride of Formula $R_1ONH_2 \cdot HCl$ and cyclized to provide a 1H-imidazo[4,5-c][1,5]naphthyridine or a 1H-imidazo[4,5-c]quinoline of Formula XXXIII. The reaction can be carried out using the method described in step (3) of Reaction Scheme I.

In steps (8) and (9) of Reaction Scheme II, a 1H-imidazo[4,5-c][1,5]naphthyridine or a 1H-imidazo[4,5-c]quinoline of Formula XXXIII is oxidized to provide an N-oxide of Formula XXXIV and then aminated to provide a 1H-imidazo[4,5-c][1,5]naphthyridin-4-amine or a 1H-imidazo[4,5-c]quinolin-4-amine of the Formula XXXV, which is a subgenus of compounds of Formulas I and II. The reactions can be carried out using the methods described in steps (4) and (5) of Reaction Scheme I, and the product or a pharmaceutically acceptable salt thereof can be isolated using conventional methods.

For some embodiments, compounds in Reaction Scheme II can be further elaborated using known synthetic methods. For example, the acid chloride used in step (6) of Reaction Scheme II may contain a protected hydroxy or amino group. Some acid chlorides of this type, for example acetoxyacetyl chloride, are commercially available. Others can be prepared by known synthetic methods. The protected hydroxy or amino group may be deprotected and further functionalized before step (8) of Reaction Scheme II. For examples of this type of functionalization of an $R_2$ group, see U.S. Pat. No. 5,389,640 (Gerster et al.).

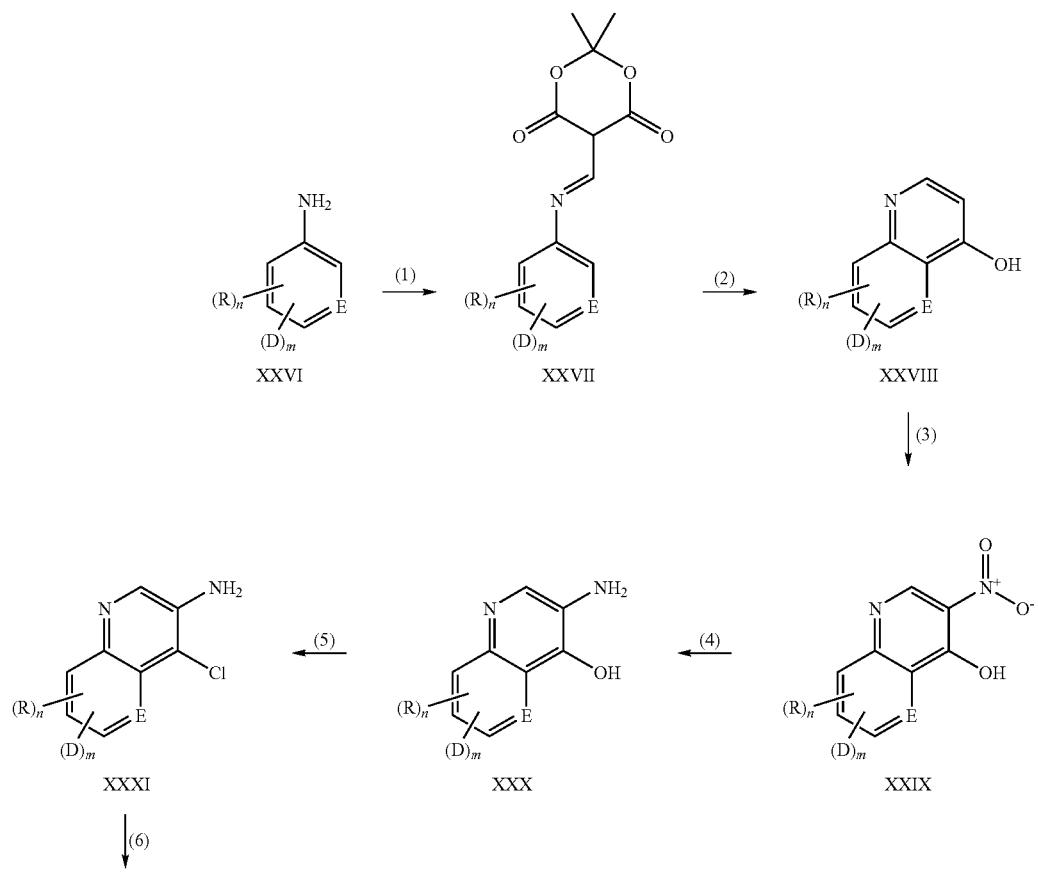

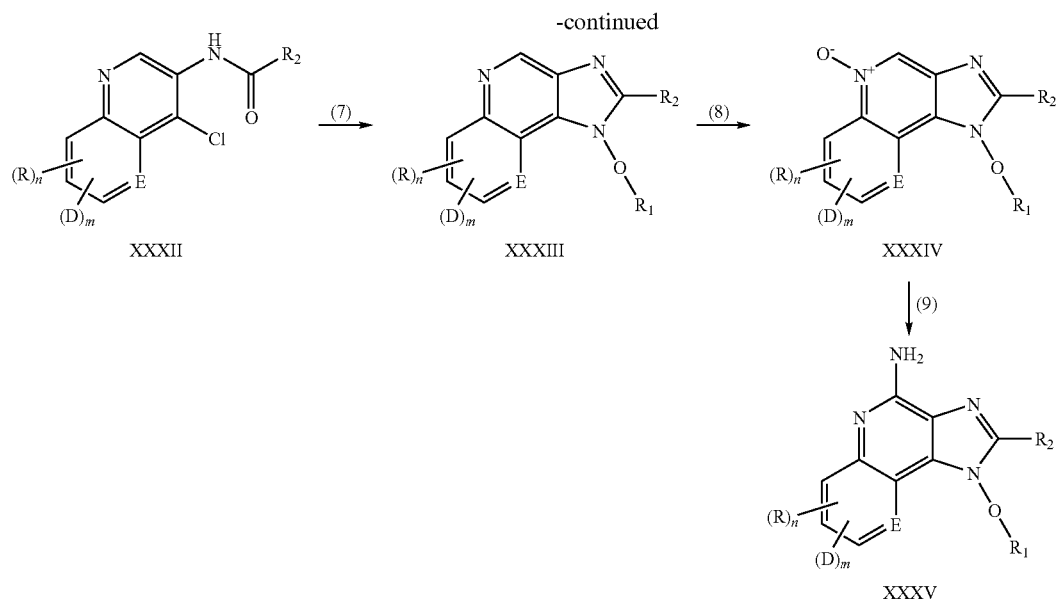

Compounds of the invention can be prepared according to Reaction Scheme III, where R, $R_1$, $R_2$, and n are as defined above, Hal is Br or I, and $R_{3a}$ is as defined below. Formula XXXVa is a subset of Formula XXXV where D is Br or I. Compounds of Formula XXXVa can be prepared according to the method of Reaction Scheme II. Reaction Scheme III can be carried out using known palladium-catalyzed coupling reactions such as Suzuki coupling, Stille coupling, Sonogashira coupling, and the Heck reaction. For example, a 1H-imidazo[4,5-c][1,5]naphthyridin-4-amine or a 1H-imidazo[4,5-c]quinolin-4-amine of Formula XXXVa undergoes Suzuki coupling with a boronic acid of Formula $R_{3a}$—$B(OH)_2$, an anhydride thereof, or a boronic acid ester of Formula $R_{3a}$—$B(O\text{-alkyl})_2$ to provide a 1H-imidazo[4,5-c][1,5]naphthyridin-4-amine or a 1H-imidazo[4,5-c]quinolin-4-amine of Formula XXXVI, a subgenus of Formula II, wherein $R_{3a}$ is -Z'-$R_4$', -Z'-X'—$R_4$', -Z'-X'—Y'—$R_4$', or -Z'-X'—$R_5$'; -Z' is a bond; —X'— is alkenylene, arylene, heteroarylene or alkenylene optionally terminated by arylene or heteroarylene; and $R_4$', Y', and $R_5$' are as defined above. The coupling is carried out by combining a compound of Formula XXXVa with a boronic acid or an ester or anhydride thereof in the presence of palladium (II) acetate, triphenylphosphine, and a base such as sodium carbonate in a suitable solvent such as n-propanol. The reaction can be carried out at an elevated temperature (e.g., 80-100° C.). Numerous boronic acids of Formula $R_{3a}$—$B(OH)_2$, anhydrides thereof, and boronic acid esters of Formula $R_{3a}$—$B(O\text{-alkyl})_2$ are commercially available; others can be readily prepared using known synthetic methods. See, for example, Li, W. et al, *J. Org. Chem.*, 67, 5394-5397 (2002). The product of Formula XXXVI or a pharmaceutically acceptable salt thereof can be isolated by conventional methods.

The Heck reaction can also be used in Reaction Scheme III to provide compounds of Formula XXXVI, wherein $R_{3a}$ is -Z'-X'—$R_4$' or -Z'-X'—Y'—$R_4$'; -Z' is a bond; —X'— is alkenylene optionally terminated by arylene or heteroarylene; and $R_4$' and Y' are as defined above. The Heck reaction is carried out by coupling a 1H-imidazo[4,5-c][1,5]naphthyridine-4-amine or a 1H-imidazo[4,5-c]quinolin-4-amine of Formula XXXVa with a vinyl-substituted arylene or heteroarylene compound. Several vinyl-substituted arylene or heteroarylene compounds, such as 2-vinylpyridine, 3-vinylpyridine, and 4-vinylpyridine, are commercially available; others can be prepared by known methods. The reaction is conveniently carried out by combining the 1H-imidazo[4,5-c][1,5]naphthyridine-4-amine or 1H-imidazo[4,5-c]quinolin-4-amine of Formula XXXVa and the vinyl-substituted compound in the presence of palladium (II) acetate, triphenylphosphine or tri-ortho-tolylphosphine, and a base such as triethylamine in a suitable solvent such as acetonitrile or toluene. The reaction can be carried out at an elevated temperature such as 100-120° C. under an inert atmosphere. The product or pharmaceutically acceptable salt thereof can be isolated using conventional methods.

Reaction Scheme III

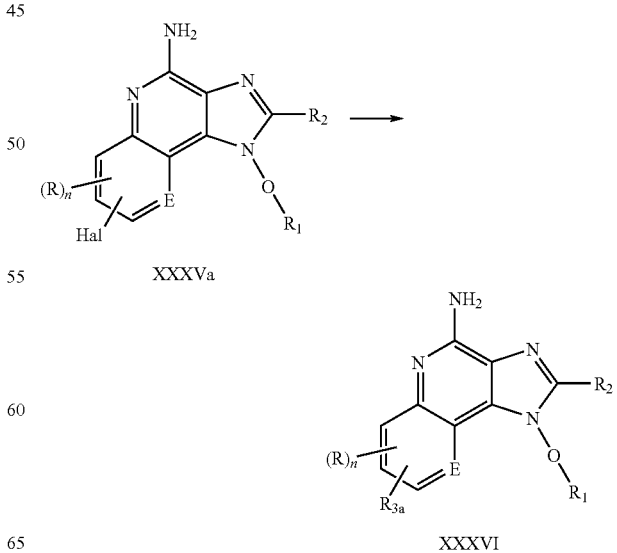

Compounds of the invention can be prepared according to Reaction Scheme IV, where $R_{A1}$, $R_{B1}$, $R_1$, and $R_2$ are as defined above and PMB is para-methoxybenzyl. In step (1) of Reaction Scheme IV, a 2,4-dichloro-3-nitropyridine of Formula XXXVII is reacted with a hydroxylamine hydrochloride of Formula $R_1ONH_2 \cdot HCl$ to provide an N-(2-chloro-3-nitropyridin-4-yl)hydroxylamine of Formula XXXVIII. The reaction can be carried out by combining the hydroxylamine with a compound of Formula XXXVII in the presence of a base such as triethylamine in an inert solvent such as DMF. The reaction can be carried out at an elevated temperature (about 80° C.). Many 2,4-dichloro-3-nitropyridines of the Formula XXXVII are known and can be readily prepared using known synthetic methods. (See, for example, Dellaria et al, U.S. Pat. No. 6,525,064 and the references cited therein).

In step (2) of Reaction Scheme IV, an N-(2-chloro-3-nitropyridin-4-yl)hydroxylamine of Formula XXXVIII is reacted with bis-(4-methoxybenzyl)amine to provide an N-{2-[bis-(4-methoxybenzyl)amino]-3-nitropyridin-4-yl}hydroxylamine of Formula XXXIX. The reaction can be carried out by adding the bis-(4-methoxybenzyl)amine to a solution of a compound of Formula XXXVIII in a suitable solvent such as toluene in the presence of a base such as triethylamine. The reaction can be carried out at an elevated temperature (about 90° C.).

In step (3) of Reaction Scheme IV, an N-{2-[bis-(4-methoxybenzyl)amino]-3-nitropyridin-4-yl}hydroxylamine of Formula XXXIX is reduced to provide an N-{3-amino-2-[bis-(4-methoxybenzyl)amino]pyridin-4-yl}hydroxylamine of Formula XL. The reduction can be carried out by treating a compound of Formula XXXIX with $NiBH_4$. The $NiBH_4$ is generated in situ by adding sodium borohydride to a mixture of nickel (II) chloride heptahydrate and methanol. A solution of a compound of Formula XXXIX in a suitable solvent such as 9:2 methanol:dichloromethane is then added to the catalyst. The reaction can be run at ambient temperature.

In step (4) of Reaction Scheme IV, an N-{3-amino-2-[bis-(4-methoxybenzyl)amino]pyridin-4-yl}hydroxylamine of Formula XL is reacted with an acyl halide of Formula $R_2C(O)Cl$ or $R_2C(O)Br$ to provide an N-(pyridin-3-yl)amide of Formula XLI. The reaction can be carried out using the method described in step (2) of Reaction Scheme I.

In step (5) of Reaction Scheme IV, an N-(pyridin-3-yl)amide of Formula XLI is cyclized to provide a 1H-imidazo[4,5-c]pyridine of Formula XLII. The reaction can be carried out by heating an amide of Formula XLI in toluene in the presence of pyridine hydrochloride. The reaction can be carried out at an elevated temperature, for example, at reflux.

In step (6) of Reaction Scheme IV, the 4-methoxybenzyl groups on a 1H-imidazo[4,5-c]pyridine of Formula XLII are removed by acid hydrolysis to provide a 1H-imidazo[4,5-c]pyridin-4-amine of Formula III. The reaction can be carried out by treating a compound of Formula XLII with trifluoroacetic acid. The reaction can be carried out at ambient temperature. The product or a pharmaceutically acceptable salt thereof can be isolated using conventional methods.

Reaction Scheme IV

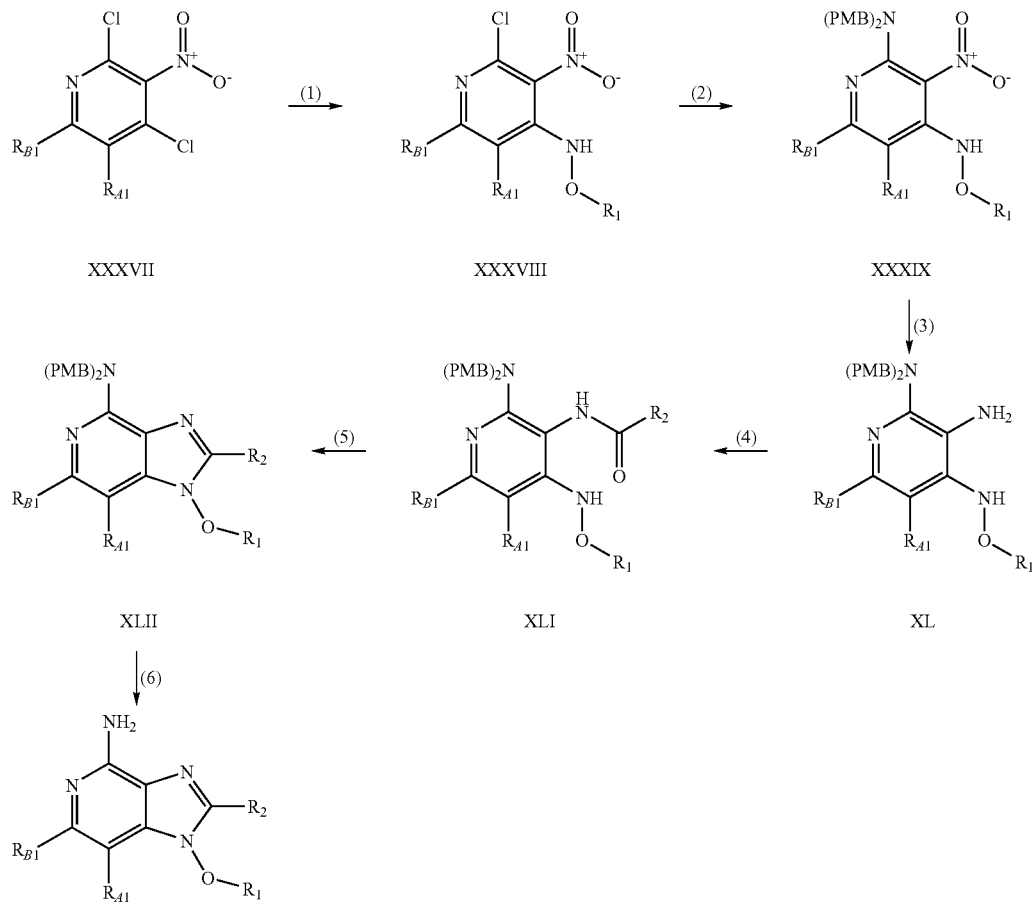

Compounds of the invention can be prepared according to Reaction Scheme V where R, $R_1$, $R_2$, and n are as defined above; and each $R_a$ is independently alkyl. Steps (1) through (4) can be carried out as described in U.S. Pat. No. 5,352,784 and documents cited therein. In step (1) the amino group of a compound of Formula XLIII can be acylated to provide a compound of Formula XLIV. The reaction can be conveniently carried out by reacting a compound of Formula XLIII with an alkyl malonyl chloride in the presence of a base such as triethylamine in a suitable solvent such as dichloromethane. Certain compounds of Formula XLIII are commercially available and others can be prepared as described in U.S. Pat. No. 5,352,784 and documents cited therein. Alkyl malonyl chlorides are known, some of which are commercially available, and others can be made by known methods.

In step (2) of Reaction Scheme V, a compound of Formula XLIV can be cyclized to provide a compound of Formula XLV. The reaction can be conveniently carried out by adding a solution of a compound of Formula XLIV in a suitable solvent such as tetrahydrofuran (THF) to a suspension of sodium hydride (or other base capable of removing a malonyl methylene proton) in a suitable solvent such as THF. The reaction can be run at an elevated temperature, for example, the reflux temperature.

In step (3) of Reaction Scheme V, a compound of Formula XLV can be hydrolyzed and decarboxylated to provide a compound of Formula XLVI. The reaction can be carried out by conventional methods, for example, by combining a compound of Formula XLV with an acid, such as hydrochloric acid, with heating.

In step (4) of Reaction Scheme V, a compound of Formula XLVI can be nitrated to provide a compound of Formula XLVII. The reaction can be carried out under conventional nitration conditions, such as by heating a compound of Formula XLVI in the presence of nitric acid, preferably in a solvent such acetic acid.

In step (5) of Reaction Scheme V, a compound of Formula XLVII can be chlorinated to provide a 2,4-dichloro-3-nitro-5,6,7,8-tetrahydroquinoline of Formula XLVIII. The reaction can be carried out by combining a compound of Formula XLVII with a conventional chlorinating agent (e.g., phosphorus oxychloride, thionyl chloride, phosgene, oxalyl chloride, or phosphorus pentachloride), optionally in a solvent such as N,N-dimethylformamide (DMF) or dichloromethane, with heating (e.g., at the reflux temperature).

In step (6) of Reaction Scheme V, 2,4-dichloro-3-nitro-5,6,7,8-tetrahydroquinoline of Formula XLVIII is reduced to provide a 3-amino-2,4-dichloro-5,6,7,8-tetrahydroquinoline of Formula XLIX. The reduction can be carried out using the methods described in step (1) of Reaction Scheme I.

In step (7) of Reaction Scheme V, a 3-amino-2,4-dichloro-5,6,7,8-tetrahydroquinoline of Formula XLIX is reacted with an acyl halide of Formula $R_2C(O)Cl$ or $R_2C(O)Br$ to provide an N-(4-chloro-5,6,7,8-tetrahydroquinolin-3-yl)amide of Formula L. The reaction can be carried out using the method described in step (2) of Reaction Scheme I.

In step (8) of Reaction Scheme V, an N-(4-chloro-5,6,7,8-tetrahydroquinolin-3-yl) amide of Formula L is reacted with a hydroxylamine hydrochloride of Formula $R_1ONH_2 \cdot HCl$ and cyclized to provide a 4-chloro-6,7,8,9-tetrahydro-1H-imidazo[4,5-c]quinoline of Formula LI. The reaction can be carried out using the method described in step (3) of Reaction Scheme I.

In step (9) of Reaction Scheme V, 4-chloro-6,7,8,9-tetrahydro-1H-imidazo[4,5-c]quinoline of Formula LI is aminated to provide a 6,7,8,9-tetrahydro-1H-imidazo[4,5-c]quinolin-4-amine of Formula V. The reaction can be carried out by heating (e.g., 125-175° C.) a compound of Formula LI under pressure in a sealed reactor in the presence of a solution of ammonia in an alkanol. The product or a pharmaceutically acceptable salt thereof can be isolated using conventional methods.

Reaction Scheme V

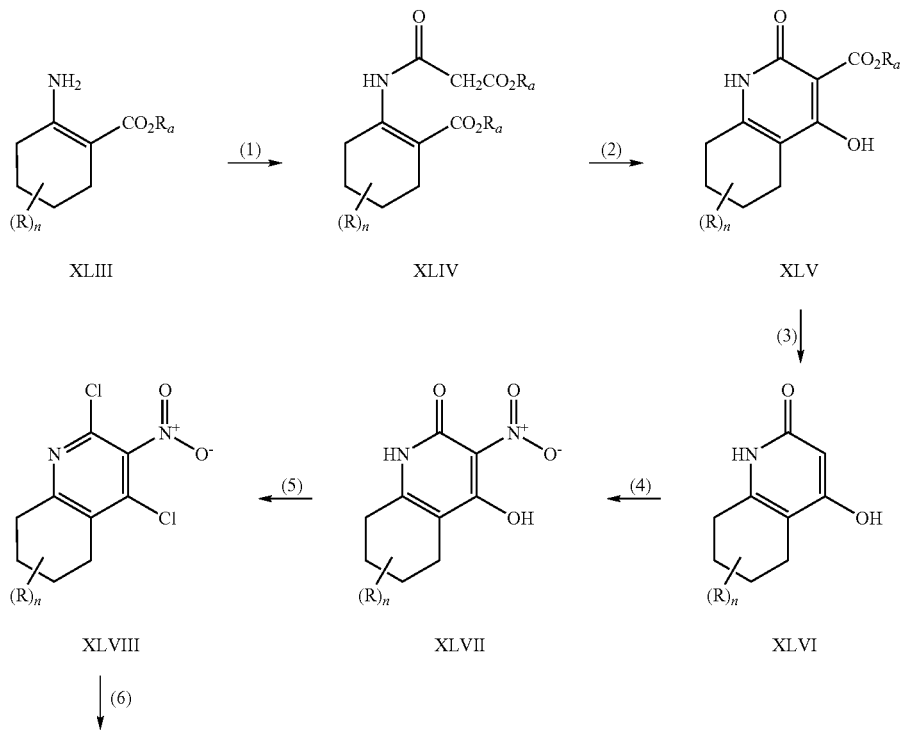

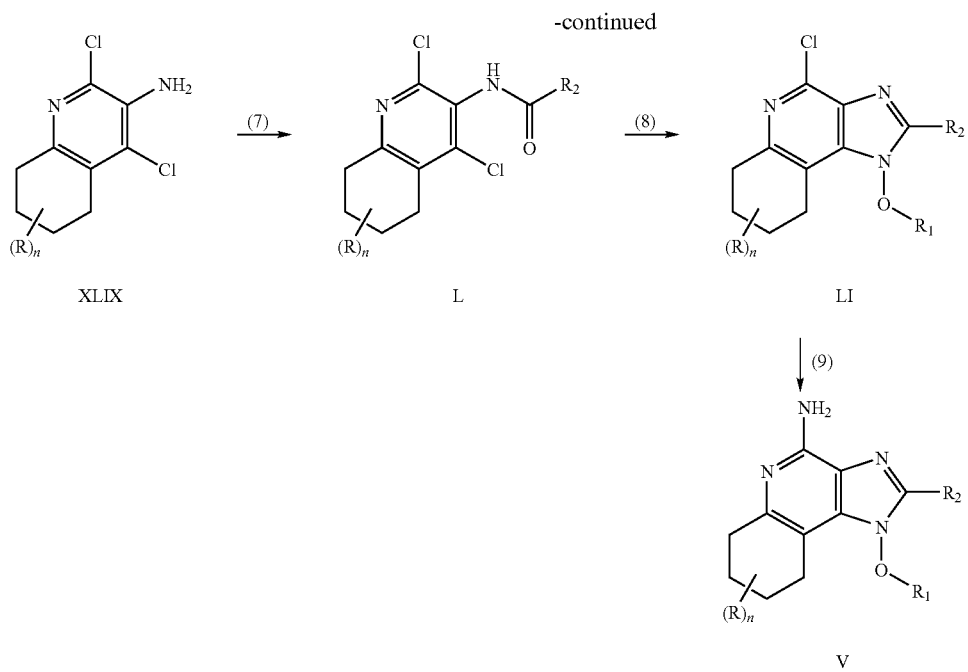

Compounds of the invention can be prepared according to Reaction Scheme VI where R, $R_1$, $R_2$, D, E, m, and n are as defined above.

In step (1) of Reaction Scheme VI, a 3-amino[1,5]naphthyridin-4-ol or 3-aminoquinolin-4-ol of Formula XXX is reacted with an acyl halide of Formula $R_2C(O)Cl$ or $R_2C(O)Br$ to provide an N-(4-hydroxy[1,5]naphthyridin-3-yl)amide or N-(4-hydroxyquinolin-3-yl)amide of Formula LVIII. The reaction can be carried out using the method described in step (2) of Reaction Scheme I.

In step (2) of Reaction Scheme VI, an N-(4-hydroxy[1,5]naphthyridin-3-yl)amide or N-(4-hydroxyquinolin-3-yl)amide of Formula LVIII is reacted with a triflating reagent such as N-phenyl-bis(trifluoromethanesulfonamide) to provide a [1,5]naphthyridin-3-yl trifluoromethanesulfonate or quinolin-3-yl trifluoromethanesulfonate of Formula LIX. A mixture of a compound of Formula LVIII, the triflating agent, a base, such as triethylamine, and an inert solvent, such as DMF, is heated at an elevated temperature, such as 75° C.

In step (3) of Reaction Scheme VI, a [1,5]naphthyridin-3-yl trifluoromethanesulfonate or quinolin-3-yl trifluoromethanesulfonate of Formula LIX is reacted with a hydroxylamine hydrochloride of Formula $R_1ONH_2 \cdot HCl$ and cyclized to provide a 1H-imidazo[4,5-c][1,5]naphthyridine or a 1H-imidazo[4,5-c]quinoline of Formula XXXIII. The reaction can be carried out using the method described in step (3) of Reaction Scheme I.

In steps (4) and (5) of Reaction Scheme VI, a 1H-imidazo[4,5-c][1,5]naphthyridine or a 1H-imidazo[4,5-c]quinoline of Formula XXXIII is oxidized to provide an N-oxide of Formula XXXIV and then aminated to provide a 1H-imidazo[4,5-c][1,5]naphthyridin-4-amine or a 1H-imidazo[4,5-c]quinolin-4-amine of the Formula XXXV, which is a subgenus of compounds of Formulas I and II. The reactions can be carried out using the methods described in steps (4) and (5) of Reaction Scheme I, and the product or a pharmaceutically acceptable salt thereof can be isolated using conventional methods.

Reaction Scheme VI

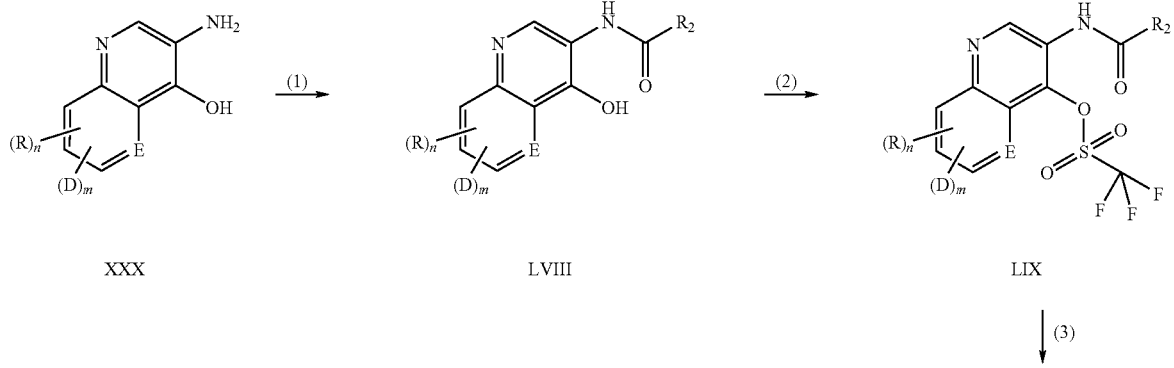

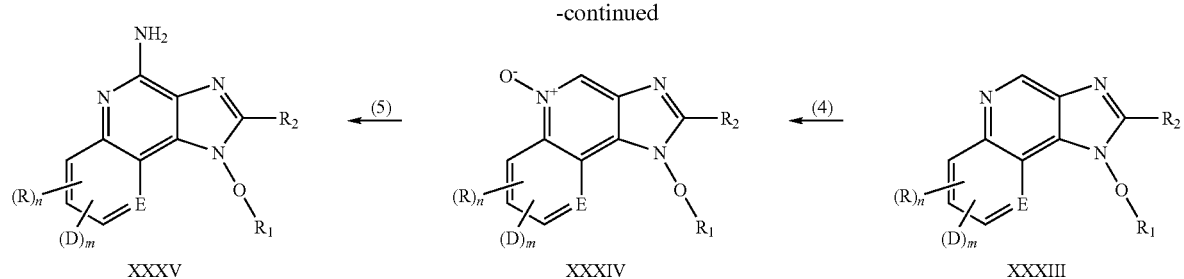

Compounds of the invention can be prepared according to Reaction Scheme VII where R, $R_2$, $R_4$, D, E, X, Y, m, and n are as defined above and Boc is tert-butoxycarbonyl.

In step (1) of Reaction Scheme VII, an N-(4-chloro[1,5]naphthyridin-3-yl)amide or N-(4-chloroquinolin-3-yl)amide of Formula XXXII is reacted with a hydroxylamine of the Formula Boc-$CH_2$—X—$CH_2$—$ONH_2$ and cyclized to provide a 1H-imidazo[4,5-c][1,5]naphthyridine or a 1H-imidazo[4,5-c]quinoline of Formula LX. The reaction can be carried out using the method described in step (3) of Reaction Scheme I. Hydroxylamines of the Formula Boc-$CH_2$—X—$CH_2$—$ONH_2$ can be prepared by conventional methods.

In step (2) of Reaction Scheme VII, the tert-butoxycarbonyl protecting group is removed under acidic conditions to provide an amino substituted 1H-imidazo[4,5-c][1,5]naphthyridine or 1H-imidazo[4,5-c]quinoline of Formula LXI. For example, a compound of Formula LX can be combined with a solution of hydrogen chloride in ethanol and heated.

In step (3) of Reaction Scheme VII, an amino substituted 1H-imidazo[4,5-c][1,5]naphthyridine or 1H-imidazo[4,5-c]quinoline of Formula LXI is converted to a substituted 1H-imidazo[4,5-c][1,5]naphthyridine or 1H-imidazo[4,5-c]quinoline of Formula LXII using conventional methods. For example, a 1H-imidazo[4,5-c][1,5]naphthyridine or a 1H-imidazo[4,5-c]quinoline of the Formula LXI can react with an acid chloride of Formula $R_4C(O)Cl$ to provide a compound of Formula LXII in which Y is —C(O)—. In addition, a compound of the Formula LXI can react with sulfonyl chloride of Formula $R_4S(O)_2Cl$ or a sulfonic anhydride of Formula $(R_4S(O)_2)_2O$ to provide a compound of Formula LXII in which Y is —$S(O)_2$—. A compound of the Formula LXI can also react with a chloroformate of Formula $R_4CO(O)Cl$ to provide a compound of Formula LXII in which Y is —C(O)—O—. Numerous acid chlorides of Formula $R_4C(O)Cl$, sulfonyl chlorides of Formula $R_4S(O)_2Cl$, sulfonic anhydrides of Formula $(R_4S(O)_2)_2O$, and chloroformates of Formula $R_4CO(O)Cl$ are commercially available; others can be readily prepared using known synthetic methods. The reaction can be conveniently carried out by adding the acid chloride of Formula $R_4C(O)Cl$, chloroformate of Formula $R_4CO(O)Cl$, sulfonyl chloride of Formula $R_4S(O)_2Cl$, or sulfonic anhydride of Formula $(R_4S(O)_2)_2O$ to a solution of a compound of Formula LXI and a base such as triethylamine in a suitable solvent such as chloroform, dichloromethane, or acetonitrile. The reaction can be carried out at ambient temperature or at a sub-ambient temperature such as 0° C.

Ureas of Formula LXII, where Y is —$C(R_7)$—$N(R_9)$—, in which $R_7$ is =O, and $R_9$ is as defined above, can be prepared by reacting a compound of Formula LXI with isocyanates of Formula $R_4N$=C=O. Numerous isocyanates of Formula $R_4N$=C=O are commercially available; others can be readily prepared using known synthetic methods. The reaction can be conveniently carried out by adding the isocyanate of Formula $R_4N$=C=O to a cooled solution of a compound of Formula LXI in a suitable solvent such as dichloromethane or chloroform. Optionally, a base such as triethylamine can be added. The reaction can be carried out at ambient temperature or at a sub-ambient temperature such as 0° C. Alternatively, a compound of Formula LXI can be treated with carbamoyl chlorides of Formula $R_4N$—$(R_9)$—C(O)Cl or Formula

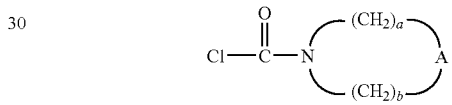

where A, a, and b are as defined above.

Thioureas of the Formula LXII, where Y is —$C(R_7)$—$N(R_9)$—, in which $R_7$ is =S, and $R_9$ is H, can be prepared by reacting a compound of Formula LXI with thioisocyanates of Formula $R_4N$=C=S using the conditions described above for the reaction of a compound of Formula LXI with isocyanates.

Sulfamides of Formula LXII, where Y is —$S(O)_2$—$N(R_6)$— wherein $R_6$ is as defined above, can be prepared by reacting a compound of Formula LXI with sulfuryl chloride to generate a sulfamoyl chloride in situ, and then reacting the sulfamoyl chloride with an amine of formula $HN(R_6)R_4$. Alternatively, sulfamides of Formula LXII can be prepared by reacting a compound of Formula LXI with a sulfamoyl chloride of Formula $R_4(R_6)N$—$S(O)_2Cl$ under the reaction conditions described above for reaction of compounds of Formula LXI with sulfonyl chlorides. Many amines of Formula $HN(R_6)R_4$, and some sulfamoyl chlorides of Formula $R_4(R_6)N$—$S(O)_2Cl$ are commercially available; others can be prepared using known synthetic methods.

In steps (4) and (5) of Reaction Scheme VII, a 1H-imidazo[4,5-c][1,5]naphthyridine or a 1H-imidazo[4,5-c]quinoline of Formula LXII is oxidized to provide an N-oxide of Formula LXIII and then aminated to provide a 1H-imidazo[4,5-c][1,5]naphthyridin-4-amine or a 1H-imidazo[4,5-c]quinolin-4-amine of the Formula LXIV. The reactions can be carried out using the methods described in steps (4) and (5) of Reaction Scheme I, and the product or a pharmaceutically acceptable salt thereof can be isolated using conventional methods.

Reaction Scheme VII

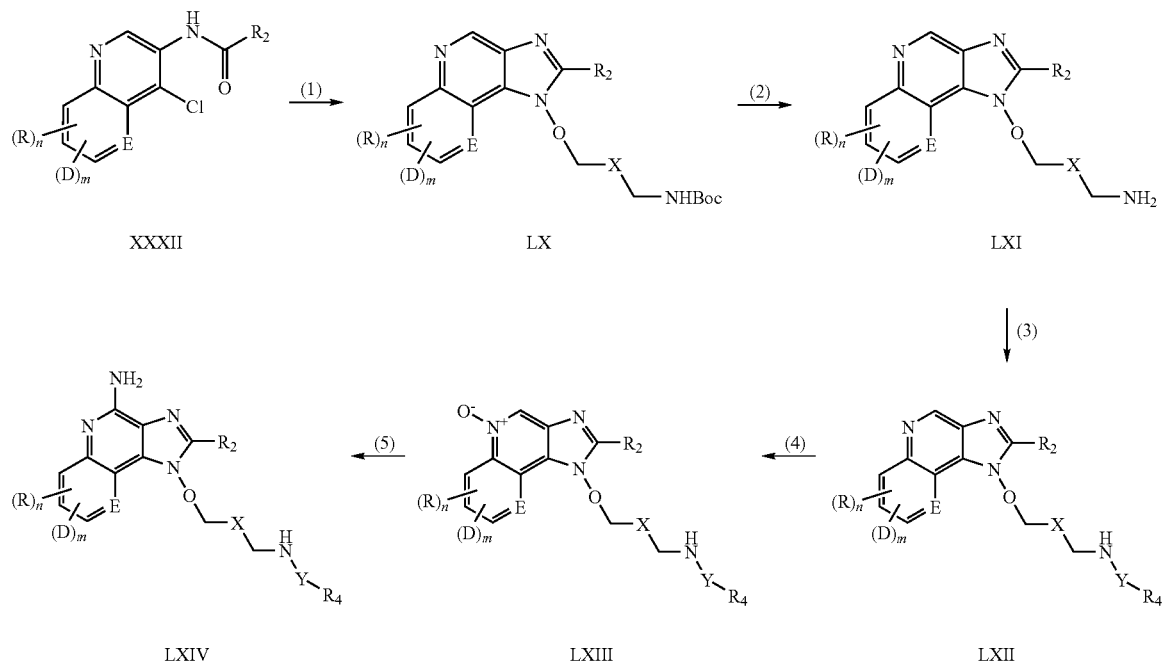

Compounds of the invention can also be prepared using the synthetic routes described in the EXAMPLES below.

Prodrugs can be prepared in a variety of ways. For example, a compound wherein $R_2$ is hydroxyalkyl can be converted into a prodrug wherein $R_2$ is, for example, -alkylenyl-O—C($R_7$)—$R_4$, -alkylenyl-O—C($R_7$)—O—$R_4$, or -alkylenyl-O—C($R_7$)—N($R_6$)—$R_4$, wherein $R_4$, $R_6$, and $R_7$ are as defined above, using methods known to one skilled in the art. In addition, a compound wherein R is hydroxy may also be converted to an ester, an ether, a carbonate, or a carbamate. For any of these compounds containing an alcohol functional group, a prodrug can be formed by the replacement of the hydrogen atom of the alcohol group with a group such as $C_{1-6}$ alkanoyloxymethyl, 1-($C_{1-6}$ alkanoyloxy)ethyl, 1-methyl-1-($C_{1-6}$ alkanoyloxy)ethyl, $C_{1-6}$ alkoxycarbonyloxymethyl, N—($C_{1-6}$ alkoxycarbonyl)aminomethyl, succinoyl, $C_{1-6}$ alkanoyl, α-amino$C_{1-4}$ alkanoyl, arylacyl, —P(O)(OH)$_2$, —P(O)(O—$C_{1-6}$ alkyl)$_2$, $C_{1-6}$ alkoxycarbonyl, $C_{1-6}$ alkylcarbamoyl, and α-aminoacyl or α-aminoacyl-α-aminoacyl, where each α-aminoacyl group is independently selected from the naturally occurring racemic, D-, and L-amino acids. For compounds containing an alcohol functional group, particularly useful prodrugs are esters made from carboxylic acids containing one to six carbon atoms, unsubstituted or substituted benzoic acid esters, or esters made from naturally occurring L-amino acids.

Prodrugs can also be made from a compound containing an amino group by conversion of the amino group to a functional group such as an amide, carbamate, urea, amidine, or another hydroylizable group using conventional methods. A prodrug of this type can be made by the replacement of a hydrogen atom in an amino group, particularly the amino group at the 4-position, with a group such as —C(O)—R', α-aminoacyl, α-aminoacyl-α-aminoacyl, —C(O)—O—R', —C(O)—N(R'''')—R', —C(=N$Y_2$)—R', —CH(OH)—C(O)—O$Y_2$, —CH(O$C_{1-4}$ alkyl)$Y_0$, —$CH_2Y_1$, or —CH($CH_3$)$Y_1$; wherein R' and R'''' are each independently $C_{1-10}$ alkyl, $C_{3-7}$ cycloalkyl, phenyl, or benzyl, each of which may be unsubstituted or substituted by one or more substitutents selected from the group consisting of halogen, hydroxy, nitro, cyano, carboxy, $C_{1-6}$ alkyl, $C_{1-4}$ alkoxy, aryl, heteroaryl, aryl$C_{1-4}$ alkylenyl, heteroaryl$C_{1-4}$ alkylenyl, halo$C_{1-4}$ alkyl, halo$C_{1-4}$ alkoxy, —O—C(O)—$CH_3$, —C(O)—O—$CH_3$, —C(O)—$NH_2$, —O—$CH_2$—C(O)—$NH_2$, —$NH2$, and —S(O)$_2$—$NH_2$; each α-aminoacyl group is independently selected from the naturally occurring racemic, D-, and L-amino acids; $Y_2$ is hydrogen, $C_{1-6}$ alkyl, or benzyl; $Y_0$ is $C_{1-6}$ alkyl, carboxy$C_{1-6}$ alkyl, amino$C_{1-4}$ alkyl, mono-N—$C_{1-6}$ alkylamino$C_{1-4}$ alkyl, or di-N,N—$C_{1-6}$ alkylamino$C_{1-4}$ alkyl; and $Y_1$ is mono-N—$C_{1-6}$ alkylamino, di-N,N—$C_{1-6}$ alkylamino, morpholin-4-yl, piperidin-1-yl, pyrrolidin-1-yl, or 4-$C_{1-4}$ alkylpiperazin-1-yl.

Pharmaceutical Compositions and Biological Activity

Pharmaceutical compositions of the invention contain a therapeutically effective amount of a compound or salt of the invention as described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. Although the exact amount of active compound or salt used in a pharmaceutical composition of the invention will vary according to factors known to those of skill in the art, such as the physical and chemical nature of the compound or salt, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject. A variety of dosage forms may be used, such as tablets, lozenges, capsules, parenteral formulations, syrups, creams, ointments, aerosol formulations, transdermal patches, transmucosal patches and the like.

The compounds or salts of the invention can be administered as the single therapeutic agent in the treatment regimen, or the compounds or salts of the invention may be administered in combination with one another or with other active agents, including additional immune response modifiers, antivirals, antibiotics, antibodies, proteins, peptides, oligonucleotides, etc.

Compounds or salts of the invention have been shown to induce, and certain compounds or salts of the invention may inhibit, the production of certain cytokines in experiments performed according to the tests set forth below. These results indicate that the compounds or salts are useful as immune response modifiers that can modulate the immune response in a number of different ways, rendering them useful in the treatment of a variety of disorders.

Cytokines whose production may be induced by the administration of compounds or salts of the invention generally include interferon-α (IFN-α) and/or tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt or composition of the invention to the animal. The animal to which the compound or salt or composition is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts of the invention can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Other cytokines whose production may be inhibited by the administration of compounds or salts of the invention include tumor necrosis factors (TNF-α). Among other effects, inhibition of TNF-α production can provide prophylaxis or therapeutic treatment of TNF-α mediated diseases in animals, making the compounds or salt useful in the treatment of, for example, autoimmune diseases. Accordingly, the invention provides a method of inhibiting TNF-α biosynthesis in an animal comprising administering an effective amount of a compound or salt or composition of the invention to the animal. The animal to which the compound or salt or composition is administered for inhibition of TNF-α biosynthesis may have a disease as described infra, for example an autoimmune disease, and administration of the compound or salt may provide therapeutic treatment. Alternatively, the compound or salt may be administered to the animal prior to the animal acquiring the disease so that administration of the compound or salt may provide a prophylactic treatment.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt and other component or components may be administered separately; together but independently such as in a solution; or together and associated with one another such as (a) covalently linked or (b) non-covalently associated, e.g., in a colloidal suspension.

Conditions for which compounds or salts identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such chlamydia, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, a compound or salt of the present invention may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens, toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, *hemophilus influenza* b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts of the present invention may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An amount of a compound or salt effective to induce or inhibit cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) or decreased (inhibited) over a background level of such cytokines. The precise amount will vary according to factors known in the art but is expected to be a dose of about 100 ng/kg to about 50 mg/kg, preferably about 10 μg/kg to about 5 mg/kg. The invention also provides a method of treating a viral infection in an animal and a method of treating a neoplastic disease in an animal comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 μg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

Objects and advantages of this invention are further illustrated by the following examples, but the particular materials and amounts thereof recited in these examples, as well as other conditions and details, should not be construed to unduly limit this invention.

EXAMPLES

Example 1

1-Methoxy-2-propyl-1H-imidazo[4,5-c]quinolin-4-amine

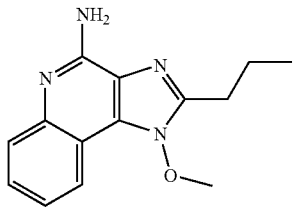

Part A

Butyryl chloride (0.72 mL, 6.94 mmol, 1.2 eq.) and triethylamine (1.13 mL, 8.09 mmol, 1.4 eq) were added to a solution of 3-amino-4-chloroquinoline (1.03 g, 5.78 mmol, 1.0 eq) in anhydrous dichloromethane (25 mL). The reaction mixture was stirred at ambient temperature for 3 hours and then washed sequentially with saturated aqueous sodium bicarbonate and brine, dried over magnesium sulfate, and concentrated under reduced pressure. The crude product was purified by column chromatography (silica gel eluting with 3% methanol in dichloromethane) to provide 0.70 g of N-(4-chloroquinolin-3-yl)butyramide.

Part B

A solution of the material from Part A (0.70 g, 2.9 mmol, 1.0 eq) and O-methylhydroxylamine hydrochloride (0.336 g, 4.0 mmol, 1.4 eq) in ethanol (50 mL) was heated at reflux for 2 hours and then concentrated under reduced pressure. Analysis of the residue by NMR and mass spectroscopy indicated that the reaction was about 30-35% complete. The residue was dissolved in ethanol (35 mL). Triethylamine (0.47 mL) and O-methylhydroxylamine hydrochloride (0.24 g) were added. The reaction mixture was heated at reflux for 2 hours at which time analysis by high performance liquid chromatography (HPLC) indicated that the reaction had not progressed. Additional O-methylhydroxylamine hydrochloride (0.500 g) was added and the reaction was heated at reflux for 1 hour at which time analysis by HPLC indicated that the reaction was complete. The reaction mixture was concentrated under reduced pressure. The residue was dissolved in dichloromethane, washed sequentially with saturated aqueous sodium bicarbonate, 10% sodium hydroxide, and brine, dried over magnesium sulfate, and concentrated under reduced pressure to provide 0.300 g of 1-methoxy-2-propyl-1H-imidazo[4,5-c]quinoline as a brown solid.

Part C

3-Chloroperbenzoic acid (0.373 g of 75%, 2.16 mmol, 1.75 eq) was added to a solution of the material from Part B (0.300 g, 1.24 mmol, 1.0 eq) in chloroform (50 mL). The reaction mixture was stirred for 2 hours at which time analysis by HPLC indicated that the reaction was complete. The reaction mixture was cooled to 0° C.; ammonium hydroxide (30 mL) was added and the reaction mixture was stirred for 15 minutes. Benzenesulfonyl chloride (0.308 mL, 2.15 mmol, 1.95 eq) was added dropwise over a period of 2 minutes. The reaction mixture was warmed to ambient temperature and then stirred for 2 hours. The reaction mixture was diluted with 10% sodium hydroxide and the layers were separated. The organic layer was washed sequentially with saturated aqueous sodium bicarbonate and brine, dried over magnesium sulfate, and concentrated under reduced pressure. The residue was purified by column chromatography (silica gel eluting with 4% methanol in dichloromethane) followed by recrystallization from 1% dichloromethane and methanol/water to provide 0.151 g of 1-methoxy-2-propyl-1H-imidazo[4,5-c]quinolin-4-amine as off-white needles, mp 210-211° C. MS (APCI) m/z 257.09 (M+H$^+$); Anal. calcd for $C_{14}H_{16}N_4O_1$: C, 65.61; H, 6.29; N, 21.86. Found: C, 65.32; H, 6.33; N, 22.1.

Example 2

1-Benzyloxy-2-propyl-1H-imidazo[4,5-c]quinolin-4-amine

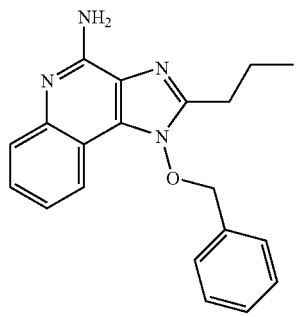

Part A

A solution of N-(4-chloroquinolin-3-yl)butyramide (3.3 g, 13 mmol, 1.0 eq) and O-benzylhydroxylamine hydrochloride (4.23 g, 26.5 mmol, 2.0 eq) in ethanol (150 mL) was heated at reflux for 3 hours. The reaction mixture was concentrated under reduced pressure. The residue was diluted with dichloromethane, washed with saturated aqueous sodium bicarbonate, dried over magnesium sulfate, and then concentrated under reduced pressure. The residue was purified by column chromatography (silica gel eluting with 3% methanol in dichloromethane) to provide 1.20 g of 1-benzyloxy-2-propyl-1H-imidazo[4,5-c]quinoline.

Part B

A solution of 1-(benzyloxy)-2-propyl-1H-imidazo[4,5-c]quinoline (2.6 g, 8.2 mmol) in dichloromethane (100 mL) was cooled to approximately 0° C., and 3-chloroperoxybenzoic acid (3.6 g of approximately 77% pure material, 16 mmol) was added over a period of several minutes. The reaction was stirred for ten minutes at 0° C., stirred for 90 minutes at room temperature, washed with saturated aqueous sodium bicarbonate (2×35 mL, containing 1 mL of 25% w/w aqueous sodium hydroxide), dried over potassium carbonate, and filtered. The resulting solution was cooled to 0° C., and trichloroacetyl isocyanate (1.22 mL, 10.3 mmol) was added with stirring. The reaction was stirred for 15 minutes at 0° C., stirred for 75 minutes at room temperature, and concentrated under reduced pressure. The residue was dissolved in methanol (60 mL), and sodium methoxide (6.3 mL of a 25% w/w solution in methanol, 29 mmol) was added with stirring. The mixture was stirred at room temperature overnight. A precipitate formed, and the reaction mixture was cooled to approximately 0° C. The precipitate was collected by filtration, recrystallized from methanol/water, and dried overnight in a vacuum oven at 70° C. to provide 1.11 g of 1-(benzyloxy)-2-propyl-1H-imidazo[4,5-c]quinolin-4-amine as white crystals, mp 164-166° C.

MS (APCI) m/z 333 (M+H$^+$);
Anal. calcd for $C_{20}H_{20}N_4O$: C, 72.27; H, 6.06; N, 16.85. Found: C, 71.94; H, 6.11; N, 16.93.

Example 3

1-Ethoxy-2-propyl-1H-imidazo[4,5-c]quinolin-4-amine

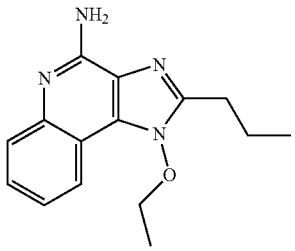

Part A

Butyryl chloride (3.77 mL, 1.3 eq) and triethylamine (5.85 mL, 1.3 eq) were added sequentially to a chilled (0° C.) solution of 3-amino-4-chloroquinoline (5.0 g, 1.0 eq) in dichloromethane (100 mL). The reaction mixture was warmed to ambient temperature and then allowed to stir overnight. The reaction mixture was quenched with aqueous saturated sodium bicarbonate. The organic layer was separated and concentrated under reduced pressure to provide 6.5 g of N-(4-chloroquinolin-3-yl)butyramide.

Part B

Ethoxyamine hydrochloride (2.34 g, 2.0 eq) was added to a solution of N-(4-chloroquinolin-3-yl)butyramide (3.0 g, 1.0 eq) in ethanol (75 mL). The reaction mixture was heated at reflux for 3 hours, cooled to ambient temperature, and then concentrated under reduced pressure. The residue was partitioned between dichloromethane and aqueous saturated sodium bicarbonate. The organic layer was separated and concentrated under reduced pressure to provide 2.89 g of 1-ethoxy-2-propyl-1H-imidazo[4,5-c]quinoline.

Part C

The material from Part B was oxidized and then aminated using the method of Example 1 Part C. The crude product was purified by column chromatography (silica gel eluting with 4% methanol in chloroform) followed by recrystallization from a mixture of water and 2% dichloromethane in methanol to provide 0.185 g of 1-ethoxy-2-propyl-1H-imidazo[4,5-c]quinolin-4-amine as brownish needles, mp 198-199° C. MS (APCI) m/z 271.16 (M+H$^+$); Anal. calcd for $C_{15}H_{18}N_4O.0.06H_2O.0.25$; $C_1H_4O$: C, 65.61; H, 6.81; N, 20.06. Found: C, 65.33; H, 6.5; N, 20.07.

Example 4

2-Ethyl-1-methoxy-1H-imidazo[4,5-c]quinolin-4-amine

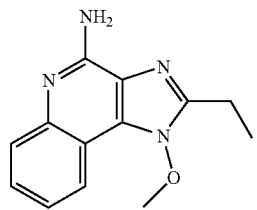

Part A

Propionyl chloride (6.32 mL, 1.3 eq) and triethylamine (11.69 mL, 1.5 eq) were added sequentially to a solution of 3-amino-4-chloroquinoline (10.0 g, 1.0 eq) in dichloromethane (200 mL). The reaction mixture was stirred overnight and then quenched with aqueous saturated sodium bicarbonate. The organic layer was separated, dried over magnesium sulfate, and then concentrated under reduced pressure. The residue was purified by column chromatography (silica gel eluting with 2% methanol in dichloromethane) to provide 5.8 g of N-(4-chloroquinolin-3-yl)propionamide.

Part B

O-methylhydroxylamine hydrochloride (1.51 g, 1.7 eq) was added to a solution of N-(4-chloroquinolin-3-yl)propionamide (2.5 g, 1.0 eq) in ethanol (75 mL). The reaction mixture was heated at reflux for 3 hours, cooled to ambient temperature, and then concentrated under reduced pressure. The residue was partitioned between dichloromethane and aqueous saturated sodium bicarbonate. The organic layer was separated and concentrated under reduced pressure to provide 2.10 g of 2-ethyl-1-methoxy-1H-imidazo[4,5-c]quinoline as a brown solid.

Part C

The material from Part B was oxidized and then aminated using the method of Example 1 Part C. The crude product was purified by column chromatography (silica gel eluting with 4-5% methanol in chloroform) followed by recrystallization from a mixture of methanol and water to provide 80 mg of 2-ethyl-1-methoxy-1H-imidazo[4,5-c]quinolin-4-amine as a tan powder, mp 216-217° C. MS (APCI) m/z 243.05 (M+H$^+$); Anal. calcd for $C_{13}H_{14}N_4O \cdot 0.05H_2O$: C, 64.22; H, 5.84; N, 23.04. Found: C, 63.83; H, 5.79; N, 22.61.

Example 5

2-Ethyl-1-isopropoxy-1H-imidazo[4,5-c]quinolin-4-amine

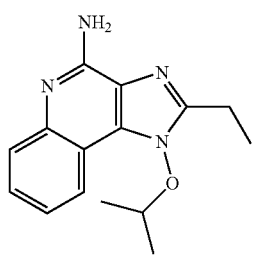

Part A

O-isopropylhydroxylamine hydrochloride (2.5 g, 1.7 eq) was added to a solution of N-(4-chloroquinolin-3-yl)propionamide (3.1 g, 1.0 eq) in ethanol (150 mL). The reaction mixture was heated at reflux for 3 hours, cooled to ambient temperature, and then concentrated under reduced pressure. The residue was partitioned between dichloromethane and aqueous saturated sodium bicarbonate. The organic layer was separated and concentrated under reduced pressure to provide 3.2 g of 2-ethyl-1-isopropoxy-1H-imidazo[4,5-c]quinoline.

Part B

The material from Part A was oxidized and then aminated using the method of Example 1 Part C. The crude product was recrystallized 3 times from a mixture of methanol and water to provide 0.244 g of 2-ethyl-1-isopropoxy-1H-imidazo[4,5-c]quinolin-4-amine as a tan powder, mp 242-243° C. MS (APCI) m/z 271.40 (M+H$^+$);

Anal. calcd for $C_{15}H_{18}N_4O$: C, 66.65; H, 6.71; N, 20.73. Found: C, 66.39; H, 6.51; N, 20.4.

Example 6

1-Isopropoxy-2-methyl-1H-imidazo[4,5-c]quinolin-4-amine

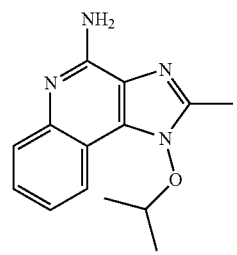

Part A

Acetyl chloride (3.41 mL, 1.25 eq) and triethylamine (6.79 mL, 1.4 eq) were added sequentially to a solution of 3-amino-4-chloroquinoline (6.22 g, 1.0 eq) in dichloromethane (100 mL). The reaction mixture was stirred overnight and then washed sequentially with aqueous saturated sodium bicarbonate and brine, dried over magnesium sulfate, and then concentrated under reduced pressure to provide 6.68 g of N-(4-chloroquinolin-3-yl)acetamide.

Part B

O-isopropylhydroxylamine hydrochloride (2.14 g, 1.7 eq) was added to a solution of N-(4-chloroquinolin-3-yl)acetamide (2.51 g, 1.0 eq) in ethanol (75 mL). The reaction mixture was heated at reflux for 2 hours and then concentrated under reduced pressure. The residue was partitioned between dichloromethane and aqueous saturated sodium bicarbonate. The organic layer was separated and concentrated under reduced pressure to provide 2.60 g of 1-isopropoxy-2-methyl-1H-imidazo[4,5-c]quinoline.

Part C

The material from Part B was oxidized and then aminated using the method of Example 1 Part C. The crude product was sonicated with 25% sodium hydroxide. The resulting powder was isolated by filtration and then washed with water to provide 151 mg of 1-isopropoxy-2-methyl-1H-imidazo[4,5-c]quinolin-4-amine as a brown powder, mp 243° C. MS (APCI) m/z 257.14 (M+H$^+$); Anal. calcd for $C_{14}H_{16}N_4O \cdot 0.41H_2O$: C, 63.76; H, 6.42; N, 21.25. Found: C, 63.39; H, 6.30; N, 20.97.

Example 7

1-Methoxy-2-methyl-1H-imidazo[4,5-c]quinolin-4-amine

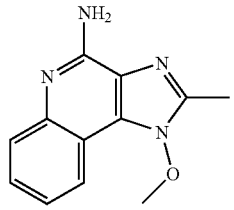

1-Methoxy-2-methyl-1H-imidazo[4,5-c]quinolin-4-amine was prepared according to the method of Example 6 using O-methylhydroxylamine hydrochloride in lieu of O-isopropylhydroxylamine hydrochloride in Part B. The crude product was purified by column chromatography (silica gel eluting with 3% methanol in chloroform) followed by recrystallization from a mixture of water and 10% dichloromethane in methanol to provide 299 mg of 1-methoxy-2-methyl-1H-imidazo[4,5-c]quinolin-4-amine as a brown powder, mp 237-238° C. MS (APCI) m/z 229.12 (M+H$^+$); Anal. calcd for $C_{12}H_{12}N_4O \cdot 0.14 CH_2Cl_2$: C, 60.72; H, 5.29; N, 24.55. Found: C, 60.82; H, 5.23; N, 23.31.

Example 8

1-Isobutoxy-2-methyl-1H-imidazo[4,5-c]quinolin-4-amine

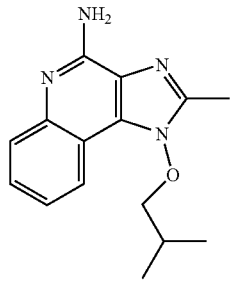

1-Isobutoxy-2-methyl-1H-imidazo[4,5-c]quinolin-4-amine was prepared according to the method of Example 6 using O-isobutyllhydroxylamine hydrochloride in lieu of O-isopropylhydroxylamine hydrochloride in Part B. The crude product was slurried 4 times with 25% sodium hydroxide and then recrystallized from a mixture of water and 5% dichloromethane in methanol to provide 370 mg of 1-isobutoxy-2-methyl-1H-imidazo[4,5-c]quinolin-4-amine as brown crystals, mp 215-216° C. MS (APCI) m/z 271.13 (M+H$^+$);

Anal. calcd for $C_{15}H_{18}N_4O$: C, 66.65; H, 6.71; N, 20.73. Found: C, 66.53; H, 6.95; N, 20.68.

Example 9

1-Ethoxy-2-methyl-1H-imidazo[4,5-c]quinolin-4-amine

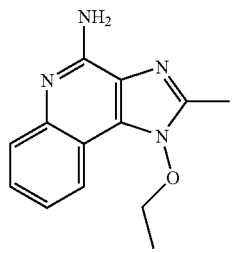

1-Ethoxy-2-methyl-1H-imidazo[4,5-c]quinolin-4-amine was prepared according to the method of Example 6 using ethoxyamine hydrochloride in lieu of O-isopropylhydroxylamine hydrochloride in Part B. The crude product was recrystallized from a mixture of water and 2% dichloromethane in methanol and then from a mixture of water and methanol to provide 1-ethoxy-2-methyl-1H-imidazo[4,5-c]quinolin-4-amine as brown crystals, mp 219-221° C. MS (APCI) m/z 243.13 (M+H$^+$); Anal. calcd for $C_{13}H_{14}N_4O \cdot 0.15 H_2O$: C, 63.76; H, 5.88; N, 22.88. Found: C, 63.36; H, 5.99; N, 22.93.

Example 10

1-Methoxy-2-phenyl-1H-imidazo[4,5-c]quinolin-4-amine

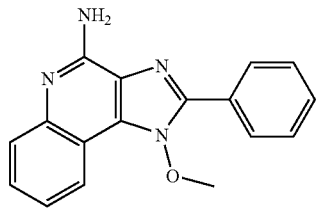

Part A

Under a nitrogen atmosphere, a mixture of 3-amino-4-chloroquinoline (2.50 g, 1 eq), benzoyl chloride (3.0 g, 1.5 eq), and anhydrous dichloromethane (100 mL) was heated at 40° C. After 23 hours additional benzoyl chloride (3.0 g, 1.5 eq) was added and heating was continued for a total of 48 hours. The reaction mixture was diluted with ethyl acetate, washed sequentially with aqueous potassium carbonate (×2), water, and brine, dried over sodium sulfate, filtered, and then concentrated under reduced pressure. The crude product was purified by column chromatography (230 g of silica gel eluted initially with a gradient of 20-50% ethyl acetate in hexanes and then with 4/3/3 dichloromethane/ethyl acetate/hexanes) to provide 1.01 g of N-(4-chloroquinolin-3-yl)benzamide as a white solid.

Part B

A mixture of N-(4-chloroquinolin-3-yl)benzamide (0.020 g, 1 eq), O-methylhydroxylamine hydrochloride (3 eq), and isopropanol was heated at 80° C. for 17 hours. The reaction was also run using ethanol in lieu of isopropanol. The two reaction mixtures were combined, diluted with ethyl acetate, washed sequentially with aqueous potassium carbonate (×2), water, and brine, dried over potassium carbonate, filtered, and then concentrated under reduced pressure. The resulting solid was dried at 80° C. for 3 days to provide 12.1 mg of 1-methoxy-2-phenyl-1H-imidazo[4,5-c]quinoline as a tan powder, mp 194.0-195° C. MS (APCI) m/z 276 (M+H)$^+$; Anal. calcd for $C_{17}H_{13}N_3O \cdot 0.2 H_2O$: C, 73.21; H, 4.84; N, 15.07. Found: C, 73.27; H, 4.61; N, 14.84.

Part C

1-Methoxy-2-phenyl-1H-imidazo[4,5-c]quinoline (3.295 g, 1 eq), 3-chloroperbenzoic acid (4.3 g of 77%, 1.6 eq), and dichloromethane (400 mL) were combined and stirred at ambient temperature. More 3-chloroperbenozic acid (0.9 g) was added after 30 minutes and again after 1.5 hours. After 3 hours total the reaction mixture was diluted with dichloromethane, washed sequentially with saturated aqueous potassium carbonate, water, and brine, dried over sodium sulfate, filtered, and then concentrated under reduced pressure until solids began to form. The heterogeneous mixture was filtered and then triturated with hexanes to provide 2.82 g of 1-methoxy-2-phenyl-1H-imidazo[4,5-c]quinoline 5N-oxide as a light tan solid.

Part D

Ammonium hydroxide (48 mL of 15M) was added to a solution of the material from Part C (1 eq) in dichloromethane (100 mL) and stirred vigorously at 0° C. Solid tosyl chloride (2.7 g, 1.5 eq) was added over a period of 1 minute. After 15 minutes the ice bath was removed. After 30 minutes the reaction mixture was diluted with dichloromethane and washed with saturated aqueous potassium carbonate. A solid formed in the aqueous layer. This material was isolated by filtration and dried to provide 1.16 g of 1-methoxy-2-phenyl-1H-imidazo[4,5-c]quinolin-4-amine as a white powder, mp 241.0-243.0° C. MS (APCI) m/z 291 (M+H)$^+$; Anal. calcd for $C_{17}H_{14}N_4O \cdot 0.3H_2O$: C, 69.05; H, 4.98; N, 18.95. Found: C, 69.17; H, 4.86; N, 19.07.

Example 11

1-Isopropoxy-2-phenyl-1H-imidazo[4,5-c]quinolin-4-amine

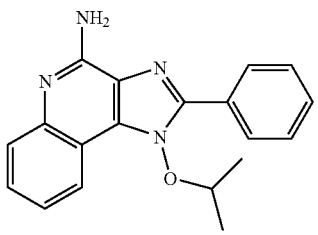

Part A

O-isopropylhydroxylamine hydrochloride (5.9 g, 3 eq), N-(4-chloroquinolin-3-yl)benzamide (5.0 g, 1 eq), and anhydrous isopropanol (60 mL) were combined and then heated at 80° C. under a nitrogen atmosphere. After 18 hours the reaction mixture was concentrated under reduced pressure. The residue was dissolved in ethyl acetate, washed sequentially with saturated aqueous potassium carbonate, water, and brine, dried over sodium sulfate, filtered, and then concentrated under reduced pressure to provide 6.15 g of dark oil. This material was purified by column chromatography (320 g of silica gel eluted with a gradient of 30-50% ethyl acetate in dichloromethane) to provide an oil. The oil was triturated with hexanes to provide a solid which was isolated by filtration and then dried to provide 3.756 g of 1-isopropoxy-2-phenyl-1H-imidazo[4,5-c]quinoline.

Part B

The material from Part A (1 eq) was combined with 3-chloroperbenzoic acid (4.1 g of 77%, 1.5 eq) and dichloromethane (50 mL) and stirred at ambient temperature for 30 minutes. The reaction mixture was diluted with dichloromethane, washed sequentially with saturated aqueous potassium carbonate, water, and brine, dried over sodium sulfate, filtered, and then concentrated under reduced pressure. The residue was triturated with a mixture of ether and hexane. The resulting solid was isolated by filtration, rinsed with hexanes, and dried to provide 3.4 g of 1-isopropoxy-2-phenyl-1H-imidazo[4,5-c]quinoline 5N-oxide as a light orange solid.

Part C

Ammonium hydroxide (49 mL of 15M) was added to a solution of material from Part B (3.126 g, 1 eq) in dichloromethane (100 mL) and stirred vigorously at 0° C. Solid tosyl chloride (2.8 g, 1.5 eq) was added over a period of 1 minute. After 15 minutes the ice bath was removed. After 30 minutes the reaction mixture was diluted with dichloromethane, washed sequentially with saturated aqueous potassium carbonate, water, and brine, dried over sodium sulfate, filtered, and then concentrated under reduced pressure. The residue was triturated with hexanes/ether to provide 2.3 g of a tan solid. This material was purified by column chromatography (200 g of silica gel eluted with a gradient of 5-10% CMA in chloroform; CMA is a 80/12/2 v/v/v chloroform/methanol/concentrated ammonium hydroxide) to provide 1.15 g of a tan solid. This material was dissolved in hot acetonitrile (20 mL). After 17 hours a solid was isolated by filtration and then dried at 100° C. under high vacuum for 17 hours to provide 0.88 g of 1-isopropoxy-2-phenyl-1H-imidazo[4,5-c]quinolin-4-amine as a tan powder, mp 188.0-191° C. MS (APCI) m/z 319 (M+H)$^+$; Anal. calcd for $C_{19}H_{18}N_4O \cdot 0.3H_2O$: C, 70.48; H, 5.79; N, 17.30. Found: C, 70.51; H, 5.74; N, 17.41.

Example 12

2-Cyclohexyl-1-isopropoxy-1H-imidazo[4,5-c]quinolin-4-amine

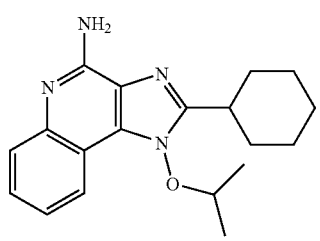

Part A

Under a nitrogen atmosphere, a mixture of 3-amino-4-chloroquinoline (8.00 g, 1 eq), cyclohexanecarbonyl chloride (18.2 mL, 3 eq) and anhydrous dichloroethane (150 mL) was heated at 90° C. for 23 hours. The reaction mixture was diluted with dichloromethane, washed sequentially with saturated aqueous potassium carbonate, water, and brine, dried over sodium sulfate, filtered, and then concentrated under reduced pressure. The residue was triturated with hexanes to provide a solid. The solid was combined with hexanes, stirred for 30 minutes, isolated by filtration, rinsed with hexanes, and then dried to provide 11.9 g of N-(4-chloroquinolin-3-yl)cyclohexanecarboxamide.

Part B

Under a nitrogen atmosphere, a mixture of N-(4-chloroquinolin-3-yl)cyclohexanecarboxamide (5.0 g, 1 eq), O-isopropylhydroxylamine hydrochloride (5.8 g, 3 eq), and anhydrous isopropanol (60 mL) was heated at 80° C. for 20 hours. The reaction mixture was concentrated under reduced pressure. The residue was dissolved in dichloromethane, washed sequentially with saturated aqueous potassium carbonate, water, and brine, dried over sodium sulfate, filtered, and then concentrated under reduced pressure. The residue was triturated with hexane to provide a solid. This material was purified by column chromatography (250 g of silica gel eluted with 2% CMA in chloroform) to provide 4 g of a brown solid. This material was purified by column chromatography (300 g of silica gel eluted with a gradient of 50-65% ethyl acetate in hexanes) to provide 2.85 g of 2-cyclohexyl-1-isopropoxy-1H-imidazo[4,5-c]quinoline as a tan solid.

Part C

The material from Part B (2.85 g, 1 eq) was combined with 3-chloroperbenzoic acid (3.6 g of 77%, 2 eq) and dichloromethane (150 mL) and stirred at ambient temperature. After 30 minutes more 3-chloroperbenzoic acid (0.8 g) was added and the reaction mixture was stirred for an additional 30 minutes. The reaction mixture was diluted with dichloromethane, washed sequentially with aqueous potassium carbonate, water, and brine, dried over sodium sulfate, filtered, and then concentrated under reduced pressure. The residue was triturated with hexanes. The resulting solid was isolated by filtration to provide 3.6 g of 2-cyclohexyl-1-isopropoxy-1H-imidazo[4,5-c]quinoline 5N-oxide as a tan solid.

Part D

Ammonium hydroxide (50 mL of 15M) was added to a solution of material from Part C (3.371 g, 1 eq) in dichloromethane (200 mL) and stirred vigorously at 0° C. Solid tosyl chloride (2.9 g, 1.5 eq) was added over a period of 1 minute. After 15 minutes the ice bath was removed. After 30 minutes the reaction mixture was diluted with dichloromethane, washed sequentially with saturated aqueous potassium carbonate, water, and brine, dried over sodium sulfate, filtered, and then concentrated under reduced pressure. The residue was triturated with hexanes/ether to provide a solid. This material was purified by column chromatography (150 g of silica gel eluted with a gradient of 5-15% CMA in chloroform) to provide 1.3 g of a white solid. This material was triturated with ether, isolated by filtration, rinsed with ether, and then dried at 70° C. under high vacuum to provide 0.53 g of 2-cyclohexyl-1-isopropoxy-1H-imidazo[4,5-c]quinolin-4-amine as a white powder, mp 175.0-178.0° C. MS (APCI) m/z 325 (M+H)$^+$; Anal. calcd for $C_{19}H_{24}N_4O$: C, 70.34; H, 7.46; N, 17.27. Found: C, 70.07; H, 7.51; N, 16.98.

Example 13

2-Cyclohexyl-1-methoxy-1H-imidazo[4,5-c]quinolin-4-amine

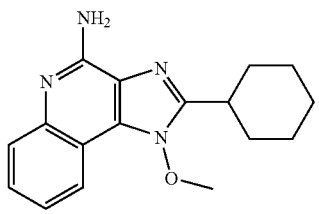

Part A

A mixture of N-(4-chloroquinolin-3-yl)cyclohexanecarboxamide (4.00 g, 1 eq), O-methylhydroxylamine hydrochloride (3.5 g, 3 eq), and ethanol (150 mL) was heated at 80° C. for 17 hours. The reaction mixture was concentrated under reduced pressure. The residue was dissolved in dichloromethane, washed sequentially with saturated aqueous potassium carbonate, water, and brine, dried over sodium sulfate, filtered, and then concentrated under reduced pressure to provide 3.1 g of dark brown oil. This material was purified by column chromatography (300 g of silica gel eluted with a gradient of 30-40% ethyl acetate in hexanes) to provide 1.8 g of 2-cyclohexyl-1-methoxy-1H-imidazo[4,5-c]quinoline as a light brown solid.

Part B

The material from Part A (1.8 g, 1 eq) was combined with 3-chloroperbenzoic acid (2.9 g of 77%, 2 eq) and dichloromethane (100 mL) and stirred at ambient temperature for 40 minutes. The reaction mixture was diluted with dichloromethane, washed sequentially with saturated aqueous potassium carbonate, water, and brine, dried over sodium sulfate, filtered, and then concentrated under reduced pressure to provide 2.82 g of a tan solid. This material was triturated with ether to provide 1.37 g of 2-cyclohexyl-1-methoxy-1H-imidazo[4,5-c]quinoline 5N-oxide as an off white solid.

Part C

Ammonium hydroxide (23 mL of 15M) was added to a solution of material from Part B (1.37 g, 1 eq) in dichloromethane (50 mL) and stirred vigorously at 0° C. Solid tosyl chloride (1.0 g, 1.2 eq) was added over a period of 1 minute. After 15 minutes the ice bath was removed. After 1 hour the reaction mixture was diluted with dichloromethane, washed sequentially with saturated aqueous potassium carbonate, water, and brine, dried over sodium sulfate, filtered, and then concentrated under reduced pressure. The residue was triturated with hexanes to provide a solid. This material was purified by column chromatography (80 g of silica gel eluted with a gradient of 5-15% CMA in chloroform) to provide 1.13 g of a white solid. This material was triturated with ether and then dried at 70° C. under high vacuum to provide 1.0 g of 2-cyclohexyl-1-methoxy-1H-imidazo[4,5-c]quinolin-4-amine as a white powder, mp 220.0-222.0° C. MS (APCI) m/z 297 (M+H)$^+$; Anal. calcd for $C_{17}H_{20}N_4O \cdot 0.1CH_2Cl_2$: C, 67.37; H, 6.68; N, 18.38. Found: C, 67.52; H, 6.85; N, 18.50.

Example 14

2-Tert-butyl-1-isopropoxy-1H-imidazo[4,5-c]quinolin-4-amine

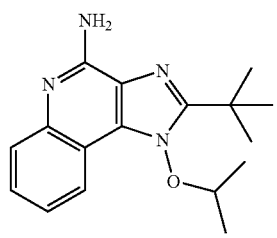

Part A

A mixture of 3-amino-4-chloroquinoline (8.00 g, 1 eq), trimethylacetyl chloride (11 mL g, 2 eq), and anhydrous dichloroethane (150 mL) was heated at 70° C. After 6 hours more trimethylacetyl chloride (2 eq) was added and heating was continued for a total of 23 hours. The reaction mixture was diluted with dichloromethane, washed sequentially with saturated aqueous potassium carbonate, water, and brine, dried over sodium sulfate, filtered, and then concentrated under reduced pressure. The residue was triturated with hexanes and then filtered to provide 7.16 g of N-(4-chloroquinolin-3-yl)trimethylacetamide as a solid. The filtrate was concentrated under reduced pressure to provide 5 g of crude N-(4-chloroquinolin-3-yl)trimethylacetamide.

Part B

Under a nitrogen atmosphere, a mixture of N-(4-chloroquinolin-3-yl)trimethylacetamide (6.00 g, 1 eq), O-isopropylhydroxylamine hydrochloride (7.6 g, 3 eq), and anhydrous isopropanol (80 mL) was heated at 80° C. for 19 hours. The reaction mixture was concentrated under reduced pressure. The residue was dissolved in dichloromethane, washed sequentially with saturated aqueous potassium carbonate, water, and brine, dried over sodium sulfate, filtered, and then concentrated under reduced pressure. The residue was purified by column chromatography (150 g of silica gel eluted with a gradient of 20-55% ethyl acetate in dichloromethane) to provide 2.8 g of 2-tert-butyl-1-isopropoxy-1H-imidazo[4,5-c]quinoline as a brown oil.

Part C

The material from Part B (2.8 g, 1 eq) was combined with 3-chloroperbenzoic acid (4.5 g of 77%, 2 eq) and dichloromethane (50 mL) and stirred at ambient temperature for 40 minutes. The reaction mixture was diluted with dichloromethane, washed sequentially with saturated aqueous potassium carbonate, water, and brine, dried over sodium sulfate, and filtered. The filtrate was washed with water and then combined with sufficient dichloromethane to bring the volume to 200 mL. Concentrated ammonium hydroxide (50 mL of 15M) was added and the mixture was stirred vigorously in an ice bath. Tosyl chloride (2.3 g, 1.2 eq) was added. After 15 minutes the ice bath was removed. After 30 minutes the reaction mixture was concentrated under reduced pressure. The residue was combined with 6 N hydrochloric acid and isopropanol. The resulting solution was made basic (pH 14) with 50% sodium hydroxide and then stirred for 30 minutes. A precipitate was isolated by filtration, triturated with toluene, isolated by filtration, rinsed with ether, and then dried at 100° C. under high vacuum for 18 hours to provide 1.2 g of 2-tert-butyl-1-isopropoxy-1H-imidazo[4,5-c]quinolin-4-amine as a light yellow powder, mp 187.0-189.0° C. MS (APCI) m/z 299 (M+H)$^+$; Anal. calcd for $C_{17}H_{22}N_4O \cdot 0.3H_2O$: C, 67.21; H, 7.50; N, 18.44. Found: C, 67.22; H, 7.14; N, 18.38.

Example 15

2-Tert-butyl-1-methoxy-1H-imidazo[4,5-c]quinolin-4-amine

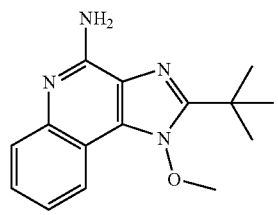

Part A

Under a nitrogen atmosphere, a mixture of N-(4-chloroquinolin-3-yl)trimethylacetamide (6.00 g, 1 eq), O-methylhydroxylamine hydrochloride (5.7 g, 3 eq), and anhydrous isopropanol (80 mL) was heated at 80° C. for 19 hours. The reaction mixture was concentrated under reduced pressure. The residue was dissolved in dichloromethane, washed sequentially with saturated aqueous potassium carbonate, water, and brine, dried over sodium sulfate, filtered, and then concentrated under reduced pressure. The residue was triturated with hexane and the resulting solid was isolated by filtration. This material was purified by column chromatography (300 g of silica gel eluted with a gradient of 20-50% ethyl acetate in dichloromethane) to provide 4.6 g of a brown solid. This solid was recrystallized from hexane to provide 3.1 g of 2-tert-butyl-1-methoxy-1H-imidazo[4,5-c]quinoline as a golden brown crystalline solid.

Part B

The material from Part A (3.1 g, 1 eq) was combined with 3-chloroperbenzoic acid (5.4 g of 77%, 2 eq) and dichloromethane (50 mL) and stirred at ambient temperature for 30 minutes. The reaction mixture was diluted with dichloromethane and washed sequentially with saturated aqueous potassium carbonate, water, and brine. The organic layer was combined with sufficient dichloromethane to bring the volume to 250 mL. Concentrated ammonium hydroxide (60 mL of 15M) was added and the mixture was stirred vigorously in an ice bath. Tosyl chloride (2.5 g, 1.1 eq) was added. After 15 minutes the ice bath was removed. After 30 minutes the reaction mixture was diluted with dichloromethane, washed sequentially with saturated aqueous potassium carbonate, water, and brine, dried over potassium carbonate, filtered, and then concentrated under reduced pressure. The residue was triturated with a mixture of toluene and ether and the resulting solid was isolated by filtration. This material was purified by column chromatography (80 g of silica gel eluted with a gradient of 7-10% CMA in chloroform) to provide 0.67 g of 2-tert-butyl-1-methoxy-1H-imidazo[4,5-c]quinolin-4-amine as a light yellow powder, mp 195.0-197.0° C. MS (APCI) m/z 271 (M+H)$^+$; Anal. calcd for $C_{15}H_{18}N_4O$: C, 66.65; H, 6.71; N, 20.73. Found: C, 66.58; H, 6.75; N, 20.75.

Example 16

1-(Benzyloxy)-2-phenyl-1H-imidazo[4,5-c]quinolin-4-amine

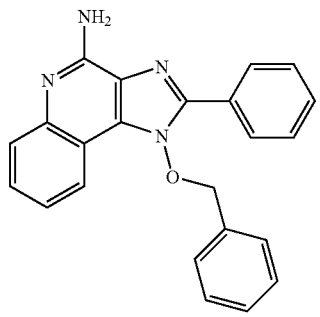

Part A

O-Benzylhydroxylamine hydrochloride (10.2 g, 63.7 mmol), N-(4-chloroquinolin-3-yl)benzamide (6.00 g, 21.2 mmol), and isopropanol (200 mL) were combined and heated at 80° C. After 18 hours the reaction mixture was concentrated under reduced pressure. The residue was dissolved in dichloromethane, and the solution was washed sequentially with saturated aqueous potassium carbonate and water and then concentrated under reduced pressure. This material was purified by column chromatography (320 g of silica gel, eluting with a gradient of 1-2% methanol in dichloromethane). The resulting solid was triturated with hexanes to provide a tan solid that was isolated by filtration. The solid was mixed with chloroform and isolated by filtration to provide 0.951 g of 1-(benzyloxy)-2-phenyl-1H-imidazo[4,5-c]quinoline as a reddish-brown solid. 2-Phenyl-1H-imidazo[4,5-c]quinolin-1-ol (2.39 g) was recovered from the aqueous washings.

Part B 1-(Benzyloxy)-2-phenyl-1H-imidazo[4,5-c]quinoline (0.951 g, 2.71 mmol) was combined with 3-chloroperoxybenzoic acid (1.2 g of 77% pure material, 5.4 mmol) in dichloromethane (10 mL) and stirred at room temperature for 30 minutes. An analysis by liquid chromatography/mass spectrometry (LC/MS) indicated the presence of starting material; additional 3-chloroperoxybenzoic acid (0.1 g) was added. The reaction mixture was stirred for 18 hours at room temperature and then diluted with dichloromethane, washed sequentially with saturated aqueous potassium carbonate, water, and brine, dried over sodium sulfate, filtered, and then concentrated under reduced pressure to provide 1.25 g of 1-(benzyloxy)-5-oxido-2-phenyl-1H-imidazo[4,5-c]quinoline as a black oil. Attempts to obtain a solid by trituration with hexane/diethyl ether and hexane were unsuccessful.

Part C

The method described in Part C of Example 11 was used to treat the material from Part B with ammonium hydroxide (13 mL of 15 M) and p-toluenesulfonyl chloride (0.57 g, 3.0 mmol) with the following modifications. Attempts to purify the crude product by trituration did not remove any impurities. Following chromatographic purification (90 g of silica gel, eluting with a gradient of 5-10% CMA in chloroform), the product was recrystallized from 40% ethyl acetate in hexane to provide 0.217 g of 1-(benzyloxy)-2-phenyl-1H-imidazo[4,5-c]quinolin-4-amine as a white powder, mp 177.0-179° C.

MS (APCI) m/z 367 (M+H)+;

Anal. calcd for $C_{23}H_{18}N_4O$: C, 75.39; H, 4.95; N, 15.29. Found: C, 75.18; H, 4.79; N, 15.05.

Example 17

4-Amino-2-phenyl-1H-imidazo[4,5-c]quinolin-1-ol

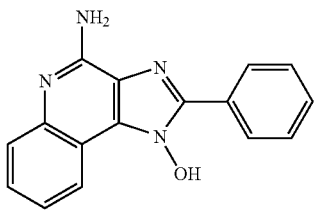

A mixture of 1-(benzyloxy)-2-phenyl-1H-imidazo[4,5-c]quinolin-4-amine (0.32 g, 0.87 mmol) and 10% palladium on carbon (0.015 g) in ethanol (10 mL) was placed in a pressure vessel, which was purged with hydrogen three times and then placed under hydrogen pressure (45 psi, $3.1 \times 10^5$ Pa) and shaken on a Parr apparatus for 18 hours. An analysis by LC/MS indicated the presence of starting material. Additional 10% palladium on carbon (0.05 g) was added, and the hydrogenation was continued for an additional five hours. The reaction mixture was filtered, and the filter cake was washed with ethanol. After several days, crystals formed in the filtrate. The filtrate was concentrated under reduced pressure until it became cloudy, and the mixture was allowed to stand for 18 hours. More crystals formed, and the crystals were collected by filtration, washed with diethyl ether, and dried to provide 0.068 g of 4-amino-2-phenyl-1H-imidazo[4,5-c]quinolin-1-ol as an off-white powder, decomp. 201-209° C.

MS (APCI) m/z 277 (M+H)+;

Anal. calcd for $C_{16}H_{12}N_4O \cdot 0.2H_2O$: C, 68.66; H, 4.47; N, 20.02. Found: C, 68.48; H, 4.66; N, 19.97.

Example 18

2-(Ethoxymethyl)-1-isopropoxy-1H-imidazo[4,5-c]quinolin-4-amine

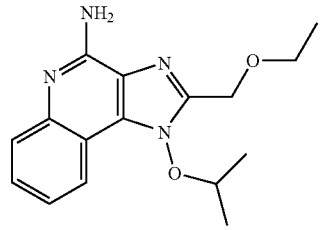

Part A

A solution of ethoxyacetyl chloride (4.2 g, 34 mmol) in dichloromethane was added dropwise to a stirred solution of 3-amino-4-chloroquinoline (5.1 g, 29 mmol) in dichloromethane (75 mL), and the reaction was stirred for one hour at room temperature. Additional ethoxyacetyl chloride (0.5 g, 4 mmol) was added, and the reaction was stirred for 30 minutes and diluted with dichloromethane (75 mL). The resulting mixture was washed with saturated aqueous sodium bicarbonate (50 mL), dried over potassium carbonate, and filtered. Methanol was added to facilitate the filtration. The filtrate was concentrated under reduced pressure to provide 7.3 g of N-(4-chloroquinolin-3-yl)-2-ethoxyacetamide as a dark solid.

Part B

A solution of N-(4-chloroquinolin-3-yl)-2-ethoxyacetamide (7.3 g, 28 mmol) and O-isopropylhydroxylamine hydrochloride (3.3 g, 0.030 mol) in ethanol (150 mL) was heated at reflux for two hours, allowed to cool to room temperature, and concentrated under reduced pressure. The residue was purified by column chromatography on silica gel (eluting with 4% methanol in dichloromethane containing 3 mL of aqueous ammonium hydroxide per liter of eluent) to provide 2.15 g of 2-(ethoxymethyl)-1-isopropoxy-1H-imidazo[4,5-c]quinoline as a dark oil that crystallized upon standing.

Part C

A solution of 2-(ethoxymethyl)-1-isopropoxy-1H-imidazo[4,5-c]quinoline (2.1 g, 7.4 mmol) in dichloromethane (75 mL) was cooled to approximately 0° C., and 3-chloroperoxybenzoic acid (3.2 g of approximately 77% pure material, 14 mmol) was added over a period of five minutes. The reaction was stirred for ten minutes at 0° C., stirred for two hours at room temperature, and then cooled to approximately 0° C. Concentrated ammonium hydroxide (35 mL) was added, and then a solution of benzenesulfonyl chloride (1.7 mL, 13 mmol) in dichloromethane (15 mL) was added dropwise. The reaction mixture was stirred for 15 minutes at 0° C. and stirred for 1.5 hours at room temperature. The aqueous layer was separated and extracted with dichloromethane (2×25 mL). The combined organic fractions were washed with saturated aqueous sodium bicarbonate (2×35 mL containing 2 mL of 25% w/w aqueous sodium hydroxide), dried over potassium carbonate, filtered, and concentrated under reduced pressure. The residue was purified by column chromatography on silica gel (eluting with 3% methanol in dichloromethane containing 3 mL of aqueous ammonium hydroxide per liter of eluent) to provide 1.3 g of a light brown solid. The solid was recrystallized three times from methanol/water and dried overnight in a vacuum oven at 80° C. to provide 0.55 g of 2-(ethoxymethyl)-1-isopropoxy-1H-imidazo[4,5-c]quinolin-4-amine as shiny brown needles, mp 179-181° C.

MS (APCI) m/z 301 (M+H$^+$);

Anal. calcd for $C_{16}H_{20}N_4O_2$: C, 63.98; H, 6.71; N, 18.65. Found: C, 63.81; H, 6.58; N, 18.73.

Example 19

4-Amino-1-isopropoxy-1H-imidazo[4,5-c]quinolin-2-yl)methanol

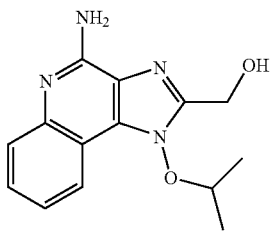

Part A

A solution of acetoxyacetyl chloride (13.8 g, 101 mmol) in dichloromethane (20 mL) was added dropwise to a stirred solution of 3-amino-4-chloroquinoline (15 g, 84 mmol) and triethylamine (27 mL, 190 mmol) in dichloromethane (150 mL), and the reaction was stirred overnight at room temperature. An analysis by LC/MS indicated the presence of starting material, and additional acetoxyacetyl chloride (11.2 g, 82.0 mmol) in dichloromethane (35 mL) was added dropwise. The reaction was stirred overnight at room temperature and then stirred for five minutes with saturated aqueous sodium bicarbonate (75 mL). The organic layer was separated and washed with saturated aqueous sodium bicarbonate (2×25 mL), dried over potassium carbonate, filtered, and concentrated under reduced pressure to provide 22.3 g of a mixture of 1:3 2-[(4-chloroquinolin-3-yl)amino]-2-oxoethyl acetate and N-(4-chloroquinolin-3-yl)-2-hydroxyacetamide as a brown, gummy solid.

Part B

A solution of 50% w/w aqueous sodium hydroxide (1 mL) and water (5 mL) was added to a solution of the mixture from Part A (10.1 g) in methanol (100 mL), and the reaction was stirred for three hours at room temperature. The volatiles were removed under reduced pressure to provide 8.7 g of N-(4-chloroquinolin-3-yl)-2-hydroxyacetamide as a brown solid.

Part C

A solution of N-(4-chloroquinolin-3-yl)-2-hydroxyacetamide (8.0 g, 34 mmol) and O-isopropylhydroxylamine hydrochloride (5.5 g, 49 mmol) in ethanol (100 mL) was heated at reflux overnight, allowed to cool to room temperature, and concentrated under reduced pressure. The residue was dissolved in dichloromethane (150 mL), and the resulting solution was washed with saturated aqueous sodium bicarbonate (2×50 mL), dried over potassium carbonate, filtered, and concentrated under reduced pressure. The crude product was purified by column chromatography on silica gel (eluting with 5% methanol in dichloromethane containing 2 mL of aqueous ammonium hydroxide per liter of eluent) to provide 3.1 g of 1-isopropoxy-1H-imidazo[4,5-c]quinolin-2-yl)methanol as a light brown solid.

Part D

The method described in Part C of Example 18 was used to oxidize and aminate 1-isopropoxy-1H-imidazo[4,5-c]quinolin-2-yl)methanol (3.0 g, 12 mmol) with the modification that chromatographic purification was carried out eluting with 5% methanol in dichloromethane containing 2 mL of aqueous ammonium hydroxide per liter of eluent. After recrystallization and drying, 4-amino-1-isopropoxy-1H-imidazo[4,5-c]quinolin-2-yl)methanol (1.23 g) was obtained as golden crystals, mp 204-206° C.

MS (APCI) m/z 273 (M+H$^+$);

Anal. calcd for $C_{14}H_{16}N_4O_2$: C, 61.75; H, 5.92; N, 20.57. Found: C, 61.57; H, 5.81; N, 20.81.

Example 20

1-Ethoxy-1H-imidazo[4,5-c]quinolin-4-amine

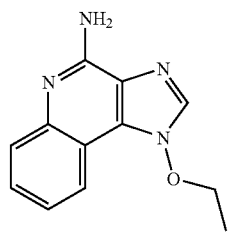

Part A

Acetic anhydride (16 mL, 170 mmol) was cooled to 0° C., and formic acid (7.2 mL of 97% pure material, 190 mmol) was added over a period of ten minutes. The solution was stirred for 2.5 hours at room temperature and then added to a stirred solution of 3-amino-4-chloroquinoline (10.0 g, 56.0 mmol) in tetrahydrofuran (THF) (100 mL). The reaction was stirred for one hour at room temperature and then concentrated under reduced pressure. Methanol (50 mL) was added to the residue, stirred for 30 minutes, and removed under reduced pressure. The residue was then stirred with dichloromethane (150 mL) and saturated aqueous sodium bicarbonate (50 mL) for three days. A solid was present and was isolated by filtration and dried under high vacuum. The filtrate was concentrated under reduced pressure, and the residue was dissolved in methanol (400 mL). The solution was dried over potassium carbonate, filtered, and concentrated under reduced pressure. The residue was combined with the solid isolated by filtration to provide 9.6 g of 4-chloroquinolin-3-ylformamide as a brown solid.

Part B

A solution of 4-chloroquinolin-3-ylformamide (5.0 g, 24 mmol), O-ethylhydroxylamine hydrochloride (2.95 g, 30.2 mmol), and isopropanol (75 mL) was heated at reflux overnight, allowed to cool to room temperature, and concentrated under reduced pressure. The residue was stirred with dichloromethane (150 mL) and saturated aqueous sodium carbonate (50 mL) for 15 minutes. The organic layer was separated and dried over potassium carbonate, filtered, and concentrated under reduced pressure. The crude product was purified by column chromatography on silica gel (eluting with 2% methanol in dichloromethane containing 5 mL of aqueous ammonium hydroxide per liter of eluent) to provide 2.45 g of 1-ethoxy-1H-imidazo[4,5-c]quinoline.

Part C

A solution of 1-ethoxy-1H-imidazo[4,5-c]quinoline (2.45 g, 11.5 mmol) in dichloromethane (100 mL) was cooled to approximately 0° C., and 3-chloroperoxybenzoic acid (3.85 g of approximately 77% pure material, 17 mmol) was added. The reaction was stirred for ten minutes at 0° C., stirred for three hours at room temperature, and then stirred with saturated aqueous sodium bicarbonate (35 mL) for 15 minutes. The aqueous layer was separated and extracted with dichloromethane (5×50 mL), and the combined organic fractions were dried over potassium carbonate, filtered, and concentrated under reduced pressure to provide 2.4 g of 1-ethoxy-5-oxido-1H-imidazo[4,5-c]quinoline as an orange solid.

Part D

A solution of 1-ethoxy-5-oxido-1H-imidazo[4,5-c]quinoline (2.4 g, 10.5 mmol) in dichloromethane (75 mL) was cooled to 0° C., and trichloroacetyl isocyanate (1.9 mL, 16 mmol) was added. The reaction was stirred for ten minutes at 0° C. and then stirred overnight at room temperature. Methanol (15 mL) was added, and the mixture was stirred for 15 minutes and concentrated under reduced pressure. The residue was dissolved in methanol (15 mL), and sodium methoxide (0.5 mL of a 25% w/w solution in methanol) was added. The mixture was stirred at room temperature for three hours and concentrated under reduced pressure. The residue was stirred with methanol (15 mL) and water (15 mL), and a solid formed. The solid was collected by filtration, recrystallized from methanol/water, and purified by column chromatography on silica gel (eluting with 5% methanol in dichloromethane containing 2 mL of aqueous ammonium hydroxide per liter of eluent). The resulting solid was recrystallized from methanol/water and dried overnight under vacuum to provide 0.54 g of 1-ethoxy-1H-imidazo[4,5-c]quinolin-4-amine as brown crystals, mp 179-181° C.

MS (APCI) m/z 229 (M+H$^+$);

Anal. calcd for $C_{12}H_{12}N_4O$: C, 63.14; H, 5.30; N, 24.55. Found: C, 62.92; H, 4.96; N, 24.72.

Example 21

1-tert-Butoxy-1H-imidazo[4,5-c]quinolin-4-amine

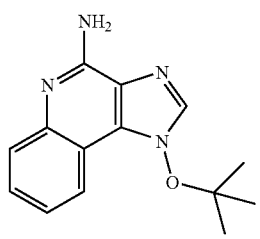

Part A

4-Chloroquinolin-3-ylformamide (4.1 g, 0.020 mol) was treated with O-(tert-butyl)hydroxylamine hydrochloride (2.8 g, 22 mmol) according to the method of Part B of Example 20 to provide 3.4 g of 1-tert-butoxy-1H-imidazo[4,5-c]quinoline, which was used without chromatographic purification.

Part B

The methods described in Parts C and D of Example 20 were used to oxidize and aminate 1-tert-butoxy-1H-imidazo[4,5-c]quinoline (3.4 g, 14 mmol) with the modification that after the final product was collected by filtration, it was purified only by column chromatography to provide 1-tert-butoxy-1H-imidazo[4,5-c]quinolin-4-amine.

HRMS (ESI) calcd for $C_{14}H_{16}N_4O_2$+H$^+$: 257.1402, found 257.1403.

Example 22

1-Methoxy-1H-imidazo[4,5-c]quinolin-4-amine

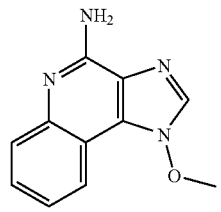

Part A

A solution of phosphorus(III) oxychloride (25.6 mL, 275 mmol) in dichloromethane (50 mL) was added dropwise to a stirred suspension of 3-aminoquinolin-4-ol hydrochloride (50.0 g, 254 mmol) in dichloromethane (500 mL) and N,N-dimethylformamide (DMF) (50 mL). After the addition was complete, the reaction was stirred at room temperature for two hours. An analysis by LC/MS indicated the presence of starting material, and additional phosphorus(III) oxychloride (25.6 mL) in dichloromethane (50 mL) was added. The reaction was stirred at room temperature overnight and was still incomplete. It was then heated at reflux for 3.5 hours and allowed to cool. Saturated aqueous sodium bicarbonate (200 mL) was added, and solid potassium carbonate was added until the mixture was basic. The organic layer was separated and washed with saturated aqueous sodium bicarbonate (2×50 mL), dried over potassium carbonate, filtered, and concentrated under reduced pressure to provide 55.1 g of N-(4-chloroquinolin-3-yl)-N,N-dimethylimidoformamide as a dark oil that solidified upon standing.

Part B

A solution of N'-(4-chloroquinolin-3-yl)-N,N-dimethylimidoformamide (10.9 g, 46.6 mmol) and O-methylhydroxylamine hydrochloride (3.9 g, 47 mmol) in ethanol (100 mL) was heated at reflux for 4.5 hours. An analysis by LC/MS indicated the reaction was incomplete, and additional O-methylhydroxylamine hydrochloride (2.0 g, 24 mmol) was added. The reaction was heated at reflux overnight, allowed to cool to room temperature, and concentrated under reduced pressure. The work-up and purification procedures described in Part C of Example 19 were followed with the modification that chromatographic purification was carried out eluting with 5% methanol in dichloromethane containing 3 mL of aqueous ammonium hydroxide per liter of eluent. 1-Methoxy-1H-imidazo[4,5-c]quinoline (approximately 3.7 g) was obtained as a red solid.

Part C

The method described in Part C of Example 18 was used to oxidize and aminate 1-methoxy-1H-imidazo[4,5-c]quinoline (2.6 g, 13 mmol) with the following modifications. The oxidation reaction mixture was stirred for three hours at room temperature and then stirred with saturated aqueous sodium bicarbonate (50 mL) for 15 minutes. The aqueous fraction was separated and extracted with dichloromethane (2×35 mL). The combined organic fractions were washed with saturated aqueous sodium bicarbonate (2×35 mL containing 2 mL of 25% w/w aqueous sodium hydroxide) and then subjected to the amination reaction. The crude amination product (2.8 g) was purified by column chromatography on silica gel (eluting with 5% methanol in dichloromethane containing 3 mL of aqueous ammonium hydroxide per liter of eluent) followed by recrystallization from methanol/water and then from isopropanol/water. The crystals were washed with 25% w/w aqueous sodium hydroxide (5×25 ml) and water (2×25 mL) and dried overnight in a vacuum oven at 70° C. to provide 0.338 g of 1-methoxy-1H-imidazo[4,5-c]quinolin-4-amine as a brown solid, mp 238-240° C.

MS (APCI) m/z 215 (M+H$^+$);

Anal. calcd for $C_{11}H_{10}N_4O$: C, 61.67; H, 4.70; N, 26.15. Found: C, 61.54; H, 4.70; N, 26.17.

Example 23

1-Isopropoxy-1H-imidazo[4,5-c]quinolin-4-amine

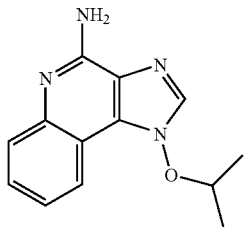

Part A

A solution of N'-(4-chloroquinolin-3-yl)-N,N-dimethylimidoformamide (9.3 g, 0.040 mol) and O-isopropylhydroxylamine hydrochloride (5.0 g, 45 mmol) in ethanol (150 mL) was heated at reflux overnight. An analysis by LC/MS indicated the reaction was incomplete, and triethylamine (2.0 mL) was added. The reaction was heated at reflux for three hours and found to be incomplete. The ethanol was removed under reduced pressure, and toluene (150 mL) was added. The reaction was heated at reflux overnight but was found again to be incomplete. The toluene was removed under reduced pressure, and ethanol (150 mL) and additional O-isopropylhydroxylamine hydrochloride (1.0 g, 9.0 mmol) were added. The reaction was heated at reflux over night with additional O-isopropylhydroxylamine hydrochloride (0.5 g) added after three hours and again (0.4 g) after five hours. The work-up and purification procedures described in Part C of Example 19 were followed with the modification that chromatographic purification was carried out eluting with 5% methanol in dichloromethane containing 3 mL of aqueous ammonium hydroxide per liter of eluent. 1-Isopropoxy-1H-imidazo[4,5-c]quinoline (7.1 g) was obtained as a light red solid.

Part B

The method described in Part C of Example 18 was used to oxidize and aminate 1-isopropoxy-1H-imidazo[4,5-c]quinoline in two batches (3.7 g, 16 mmol and 3.2 g, 14 mmol) with the following modifications. The crude amination product was purified by column chromatography on silica gel (eluting with 5% methanol in dichloromethane containing 2 mL of aqueous ammonium hydroxide per liter of eluent) followed by recrystallization twice from methanol/water and then twice from acetonitrile/water. The crystals were dried overnight in a vacuum oven at 70° C. to provide 0.926 g of 1-isopropoxy-1H-imidazo[4,5-c]quinolin-4-amine as a light brown solid, mp 224-225° C.

MS (APCI) m/z 243 (M+H$^+$);

Anal. calcd for $C_{13}H_{14}N_4O$: C, 64.45; H, 5.82; N, 23.12. Found: C, 64.39; H, 5.94; N, 23.34.

Example 24

4-Amino-2-propyl-1H-imidazo[4,5-c]quinolin-1-ol

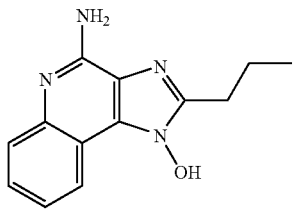

A mixture of 1-(benzyloxy)-2-propyl-1H-imidazo[4,5-c]quinolin-4-amine (3.2 g, 9.6 mmol) and 10% palladium on carbon (0.15 g) in ethanol (125 mL) was placed under hydrogen pressure (30 psi, $2.1 \times 10^5$ Pa) and shaken on a Parr apparatus for 80 minutes. After 40 minutes the hydrogen pressure had decreased to 20 psi, ($14 \times 10^5$ Pa). The reaction mixture was filtered through a layer of CELITE filter agent, and the filtrate was concentrated under reduced pressure. The residue (2.4 g) was recrystallized three times from methanol/water and dried overnight in a vacuum oven at 70° C. to provide 4-amino-2-propyl-1H-imidazo[4,5-c]quinolin-1-ol as white crystals, mp 232-235° C.

MS (APCI) m/z 243 (M+H$^+$);

Anal. calcd for $C_{13}H_{14}N_4O \cdot 0.54 H_2O$: C, 61.97; H, 6.03; N, 22.23. Found: C, 62.18; H, 6.40; N, 22.33.

Example 25

2-Isopropyl-1-methoxy-1H-imidazo[4,5-c]quinolin-4-amine

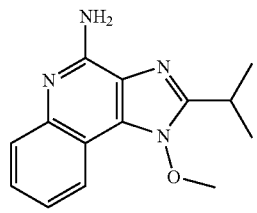

Part A

A solution of 3-amino-4-chloroquinoline (8.5 g, 48 mmol) in dichloromethane (100 mL) was cooled to 0° C. Triethylamine (42 mL, 0.30 mol) was added followed by a solution of isobutyryl chloride (9.6 mL, 0.10 mol) in dichloromethane (35 mL), which was added dropwise. The reaction was stirred overnight at room temperature. An analysis by LC/MS indicated the presence of starting material, and the reaction was heated at reflux for two hours. The reaction was still incomplete. The volatiles were removed under reduced pressure, and the residue was dissolved in dichloromethane (75 mL). Additional isobutyryl chloride (9.6 mL, 0.10 mol) was added, the reaction was stirred for three days at room temperature. The reaction was still incomplete, and additional isobutyryl chloride (3 mL) was added. The reaction was stirred overnight, diluted with methanol (10 mL), stirred for 30 minutes, and concentrated under reduced pressure. The residue was dissolved in dichloromethane (150 mL), and the solution was washed with saturated aqueous sodium bicarbonate (3×50 mL), dried over potassium carbonate, filtered, and concentrated under reduced pressure to provide 9.6 g of N-(4-chloroquinolin-3-yl)-2-methylpropanamide as a brown solid.

Part B

A solution of N-(4-chloroquinolin-3-yl)-2-methylpropanamide (6.0 g, 24 mmol), O-methylhydroxylamine hydrochloride (2.5 g, 0.030 mol), and ethanol (75 mL) was heated at reflux for five hours, allowed to cool to room temperature, stirred overnight, and concentrated under reduced pressure. The residue was dissolved in dichloromethane (100 mL), and the solution was washed with saturated aqueous sodium carbonate (2×50 mL) dried over potassium carbonate, filtered, and concentrated under reduced pressure to provide 4.9 g of 2-isopropyl-1-methoxy-1H-imidazo[4,5-c]quinoline as a dark oil.

Part C

The method described in Part C of Example 20 was used to oxidize 2-isopropyl-1-methoxy-1H-imidazo[4,5-c]quinoline (4.9 g, 0.020 mol) with the modification that the reaction was stirred at room temperature overnight and then stirred with aqueous sodium hydroxide solution (100 mL of 15% w/w) for 15 minutes.

Part D

Trichloroacetyl isocyanate (3.3 mL, 28 mmol) was added to a solution of 2-isopropyl-1-methoxy-5-oxido-1H-imidazo[4,5-c]quinoline (4.7 g, 118 mmol) in dichloromethane (100 mL), and the reaction was stirred three hours at room temperature. Methanol (20 mL) was added, and the mixture was stirred for 15 minutes and concentrated under reduced pressure. The residue was dissolved in methanol (25 mL), and sodium methoxide (0.5 mL of a 4.5 N solution in methanol) was added. The mixture was stirred at room temperature for three days and concentrated under reduced pressure. The residue was stirred with dichloromethane (25 mL). A solid was present and was collected by filtration, recrystallized from methanol/water, and dried overnight in a vacuum oven at 70° C. to provide 0.878 g of 2-isopropyl-1-methoxy-1H-imidazo[4,5-c]quinolin-4-amine as tan needles, mp 217-219° C.

MS (APCI) m/z 257 (M+H$^+$);

Anal. calcd for $C_{14}H_{16}N_4O \cdot 0.33H_2O$: C, 64.13; H, 6.40; N, 21.37. Found: C, 63.82; H, 6.47; N, 21.63.

Example 26

1-Isopropoxy-2-isopropyl-1H-imidazo[4,5-c]quinolin-4-amine

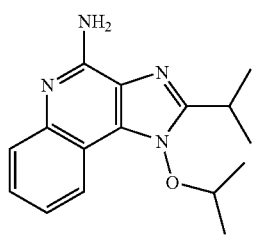

Part A

The method of Part B of Example 25 was followed using N-(4-chloroquinolin-3-yl)-2-methylpropanamide (3.6 g, 14.5 mmol), O-isopropylhydroxylamine hydrochloride (1.8 g, 16 mmol) in lieu of O-methylhydroxylamine hydrochloride, and ethanol (60 mL). 1-Isopropoxy-2-isopropyl-1H-imidazo[4,5-c]quinoline (2.2 g) was obtained as a dark oil.

Part B

The method described in Part C of Example 20 was used to oxidize 1-isopropoxy-2-isopropyl-1H-imidazo[4,5-c]quinoline (2.2 g, 8.2 mmol) with the modification that aqueous sodium hydroxide solution (35 mL of 15% w/w) was used in lieu of saturated aqueous sodium bicarbonate during the work-up procedure.

Part C

The method described in Part D of Example 25 was used to aminate 1-isopropoxy-2-isopropyl-5-oxido-1H-imidazo[4,5-c]quinoline (1.62 g, 5.7 mmol) with the modification that the reaction with sodium methoxide was stirred overnight at room temperature, and a precipitate formed. The precipitate was recrystallized three times from toluene/hexane and dried overnight in a vacuum oven at 70° C. to provide 0.428 g of 1-isopropoxy-2-isopropyl-1H-imidazo[4,5-c]quinolin-4-amine as off-white crystals, mp 177-179° C.

MS (APCI) m/z 285 (M+H$^+$);

Anal. calcd for $C_{16}H_{20}N_4O \cdot 0.24H_2O$: C, 66.58; H, 7.15; N, 19.41. Found: C, 66.54; H, 7.23; N, 19.46.

Example 27

2-Butyl-1-methoxy-1H-imidazo[4,5-c]quinolin-4-amine

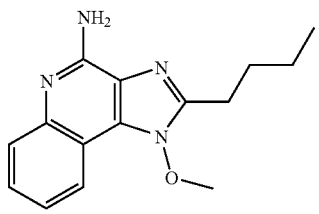

Part A

A solution of valeryl chloride (13.3 mL, 112 mmol) in dichloromethane (35 mL) was added dropwise to a stirred solution of 3-amino-4-chloroquinoline (10.0 g, 56 mmol) and triethylamine (2.1 mL, 15 mmol) in dichloromethane (100 mL), and the reaction was stirred overnight at room temperature and then stirred for one hour with saturated aqueous sodium bicarbonate (150 mL). The aqueous layer was separated and extracted with dichloromethane (2×50 mL). The combined organic fractions were washed with saturated aqueous sodium bicarbonate (50 mL), dried over potassium carbonate, filtered, and concentrated under reduced pressure. The residue was recrystallized from toluene/hexane to provide 11.1 g of N-(4-chloroquinolin-3-yl)pentanamide as a light brown solid.

Part B

The method described in Part B of Example 25 was used with the modification that the reaction was heated at reflux overnight. 2-Butyl-1-methoxy-1H-imidazo[4,5-c]quinoline (3.2 g) was obtained as a dark oil.

Part C

The methods described in Parts C and D of Example 20 were used to oxidize and aminate 2-butyl-1-methoxy-1H-imidazo[4,5-c]quinoline (3.2 g, 12.5 mmol) with the following modifications. The oxidation reaction was stirred for two hours at room temperature. The reaction with trichloroacetyl isocyanate (2.2 mL, 19 mmol) was carried out at room temperature overnight, and the reaction sodium methoxide was stirred overnight and then concentrated under reduced pressure. The residue was treated with methanol (5 mL) to form a solid, which was collected by filtration and recrystallized from methanol/water and dried overnight in a vacuum oven at 70° C. to provide 0.946 g of 2-butyl-1-methoxy-1H-imidazo[4,5-c]quinolin-4-amine as golden crystals, mp 197-199° C.

MS (APCI) m/z 271 (M+H$^+$);

Anal. calcd for $C_{15}H_{18}N_4O$: C, 66.64; H, 6.71; N, 20.72. Found: C, 66.52; H, 6.47; N, 20.86.

Example 28

2-Butyl-1-isopropoxy-1H-imidazo[4,5-c]quinolin-4-amine

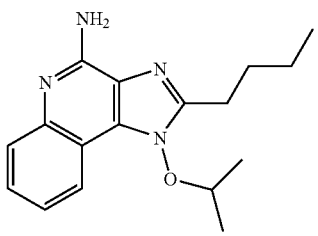

Part A

The method of Part B of Example 25 was followed using O-isopropylhydroxylamine hydrochloride (2.4 g, 21 mmol) in lieu of O-methylhydroxylamine hydrochloride to treat N-(4-chloroquinolin-3-yl)pentanamide (4.5 g, 17 mmol) with the modification that the reaction was heated at reflux overnight. 2-Butyl-1-isopropoxy-1H-imidazo[4,5-c]quinoline (3.5 g) was obtained as a dark oil.

Part B

The method of Part C of Example 20 was used to oxidize 2-butyl-1-isopropoxy-1H-imidazo[4,5-c]quinoline (3.5 g, 12 mmol) with the modification that aqueous sodium hydroxide (35 mL of 15% w/w) was used in lieu of saturated aqueous sodium bicarbonate during the work-up procedure.

Part C

The method of Part D of Example 20 was used to aminate the material from Part B with the following modifications. The reaction with trichloroacetyl isocyanate (2.2 mL, 19 mmol) was carried out at room temperature overnight. An analysis by LC/MS indicated the reaction was incomplete, and additional trichloroacetyl isocyanate (2.2 mL) was added. The reaction was stirred for three hours at room temperature, and then subjected to the reaction with sodium methoxide and stirred overnight. Chromatographic separation was carried out immediately after the sodium methoxide reaction mixture was concentrated under reduced pressure. The resulting dark oil was dissolved in dichloromethane (50 mL) and treated with excess 1 N hydrogen chloride in diethyl ether. The mixture was concentrated under reduced pressure, and the residue was stirred with dichloromethane. The resulting solid was dissolved in methanol (50 mL) and stirred with excess 0.5 N potassium hydroxide in methanol for two hours. The solid was collected by filtration, washed with water, recrystallized three times from methanol/water, and dried overnight in a vacuum oven at 70° C. to provide 0.498 g of 2-butyl-1-isopropoxy-1H-imidazo[4,5-c]quinolin-4-amine as off-white crystals, mp 118-119° C.

MS (APCI) m/z 299 (M+H$^+$);

Anal. calcd for $C_{17}H_{22}N_4O \cdot 0.08H_2O$: C, 68.09; H, 7.45; N, 18.68. Found: C, 67.75; H, 7.58; N, 18.64.

Example 29

2-Methyl-1-[(2-nitrobenzyl)oxy]-1H-imidazo[4,5-c]quinolin-4-amine

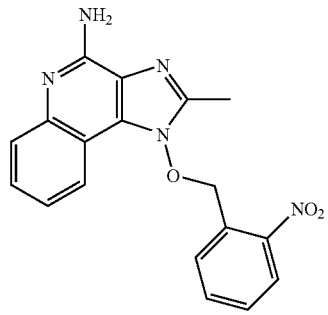

Part A

A mixture of benzohydroxamic acid (3.2 g, 23 mmol), aqueous sodium hydroxide (1.85 mL of 50% w/w, 23 mmol), and water (10 mL) was stirred and warmed. Ethanol (25 mL) was added, and the resulting solution was allowed to cool somewhat before the addition of 2-nitrobenzyl bromide (5.0 g, 23 mmol) and additional ethanol (approximately 50 mL). The solution was then heated at reflux for two hours and concentrated under reduced pressure. Dichloromethane (100 mL) and water (25 mL) were added to the residue. The aqueous layer was separated and extracted with dichloromethane (25 mL). The combined organic fractions were washed with saturated aqueous sodium bicarbonate (25 mL), dried over potassium carbonate, filtered, and concentrated under reduced pressure. The resulting yellow oil (4.0 g) was dissolved in ethanol (25 mL) and concentrated hydrochloric acid (5 mL), and the solution was heated at reflux for one hour. The volatiles were removed under reduced pressure, and the resulting white semi-solid was stirred with diethyl ether (50 mL) and water (35 mL) for 15 minutes. The aqueous fraction was separated and concentrated under reduced pressure to provide 1.6 g of O-(2-nitrobenzyl)hydroxylamine hydrochloride.

Part B

A solution of 3-amino-4-chloroquinoline (20.0 g, 112 mmol) in dichloromethane (125 mL) was cooled to 0° C. Triethylamine (47.0 mL, 0.336 mol) was added followed by a solution of acetyl chloride (16.0 mL, 0.224 mol) in dichloromethane (45 mL), which was added dropwise. The reaction was stirred overnight at room temperature. An analysis by LC/MS indicated the presence of starting material, and additional acetyl chloride (4 mL, 56 mmol) was added. The reaction was stirred for four hours at room temperature. Saturated aqueous sodium bicarbonate (100 mL) was added, and the mixture was stirred for three days. The organic layer was separated and washed with saturated aqueous sodium bicarbonate (2×50 mL), dried over potassium carbonate, filtered, and concentrated under reduced pressure to provide N-(4-chloroquinolin-3-yl)acetamide as a dark red solid.

Part C

The method of Part B of Example 20 was followed using N-(4-chloroquinolin-3-yl)acetamide (10.6 g, 48.0 mmol) in lieu of 4-chloroquinolin-3-ylformamide and O-(2-nitrobenzyl)hydroxylamine hydrochloride (10.8 g, 52.8 mmol) in lieu of O-ethylhydroxylamine hydrochloride in isopropanol (120 mL). Chromatographic purification was carried out eluting with 5% methanol in dichloromethane containing 2 mL of aqueous ammonium hydroxide per liter of eluent to provide 7.6 g of 2-methyl-1-[(2-nitrobenzyl)oxy]-1H-imidazo[4,5-c]quinoline.

Part D

The method of Part C of Example 20 was used to oxidize 2-methyl-1-[(2-nitrobenzyl)oxy]-1H-imidazo[4,5-c]quinoline (2.0 g, 6.0 mmol) with the following modifications. Aqueous sodium hydroxide (2 mL of 50% w/w) was added to the saturated aqueous sodium bicarbonate (35 mL) used during the work-up procedure, and methanol was added to the dichloromethane extractions to provide a homogeneous solution.

Part E

The method of Part D of Example 20 was used to aminate the material from Part D using the following modifications. The reaction with trichloroacetyl isocyante was stirred for four days. After the reaction with sodium methoxide, the solution was concentrated under reduced pressure, the residue was stirred with methanol (15 mL), collected by filtration, and recrystallized from methanol/water (75 mL). A second recrystallization was carried out after hot filtration of the product in methanol (150 mL). The filtrate was concentrated to 50 mL, and water (5 mL) was added. The resulting crystals were collected by filtration and dried overnight in a vacuum oven at 70° C. to provide 0.370 g of 2-methyl-1-[(2-nitrobenzyl)oxy]-1H-imidazo[4,5-c]quinolin-4-amine as yellow crystals, mp 215-217° C. MS (APCI) m/z 350 (M+H);

Anal. calcd for $C_{18}H_{15}N_5O_3$: C, 61.89; H, 4.33; N, 20.05. Found: C, 61.61; H, 4.08; N, 19.93.

Example 30

1-tert-Butoxy-2-methyl-1H-imidazo[4,5-c]quinolin-4-amine

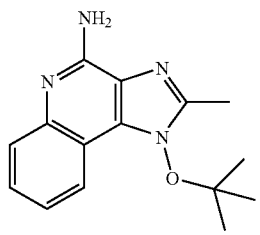

Part A

The method of Part B of Example 25 was followed using O-(tert-butyl)hydroxylamine hydrochloride (2.0 g, 16 mmol) in lieu of O-methylhydroxylamine hydrochloride to treat N-(4-chloroquinolin-3-yl)acetamide (3.2 g, 14.5 mmol) with the modification that the reaction was heated at reflux for three hours. Following the work-up procedure, the resulting blue oil was purified by column chromatography on silica gel (eluting with 5% methanol in dichloromethane containing 5 mL of aqueous ammonium hydroxide per liter of eluent) to provide 1.92 g of 1-tert-butoxy-2-methyl-1H-imidazo[4,5-c]quinoline as a blue oil.

Part B

The method described in Part C of Example 20 was used to oxidize 1-tert-butoxy-2-methyl-1H-imidazo[4,5-c]quinoline (1.67 g, 6.54 mmol) with the modification that the reaction was stirred at room temperature for 45 minutes and then stirred with dichloromethane (25 mL) and aqueous sodium hydroxide solution (10 mL of 15% w/w) for 15 minutes.

Part C

Trichloroacetyl isocyanate (1.2 mL, 0.010 mol) was added to a solution of the material from Part B in dichloromethane (75 mL), and the reaction was stirred 45 minutes at room temperature. An analysis by LC/MS indicated the reaction was incomplete, and addition trichloroacetyl isocyanate (0.50 mL) was added. The reaction was stirred for one hour, and methanol (20 mL) was added. The mixture was stirred for 15 minutes and concentrated under reduced pressure. The residue was dissolved in methanol (25 mL), and sodium methoxide (0.5 mL of a 4.5 N solution in methanol) was added. The mixture was stirred at room temperature overnight, and a solid was present. The mixture was cooled for one hour at 0° C., and the solid was collected by filtration, recrystallized from methanol/water, and dried overnight in a vacuum oven at 70° C. to provide 0.560 g of 1-tert-butoxy-2-methyl-1H-imidazo[4,5-c]quinolin-4-amine as white crystals, mp 255-257° C.

MS (APCI) m/z 271 (M+H$^+$);

Anal. calcd for $C_{15}H_{18}N_4O$: C, 66.64; H, 6.71; N, 20.72. Found: C, 66.46; H, 6.64; N, 20.94.

Example 31

2-Methyl-1-(2-phenoxyethoxy)-1H-imidazo[4,5-c]quinolin-4-amine

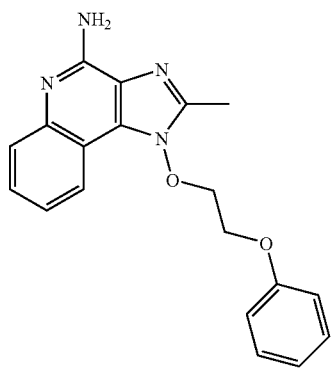

Part A

The method of Part B of Example 25 was used to treat N-(4-chloroquinolin-3-yl)acetamide (2.9 g, 13 mmol) with O-(2-phenoxyethyl)hydroxylamine hydrochloride (2.5 g, 13 mmol) in lieu of O-methylhydroxylamine hydrochloride with the modification that the reaction was heated at reflux overnight. 2-Methyl-1-(2-phenoxyethoxy)-1H-imidazo[4,5-c]quinoline (2.7 g) was obtained as a dark oil.

Part B

The method of Part C of Example 20 was used to oxidize 2-methyl-1-(2-phenoxyethoxy)-1H-imidazo[4,5-c]quinoline (2.7 g, 8.5 mmol) with the modification that aqueous sodium hydroxide (35 mL of 15% w/w) was used in lieu of saturated aqueous sodium bicarbonate during the work-up procedure.

Part C

The method of Part D of Example 20 was used to aminate 2-methyl-1-(2-phenoxyethoxy)-1H-imidazo[4,5-c]quinoline (2.6 g, 7.8 mmol) using the following modifications. The reaction with sodium methoxide was stirred overnight at room temperature and then concentrated under reduced pressure. Chromatographic purification was carried out, and the resulting yellow solid (1.7 g) was recrystallized twice from hot toluene (50 mL), methanol (25 mL), and water (4 mL). The crystals were dried overnight in a vacuum oven at 70° C. to provide 1.11 g of 2-methyl-1-(2-phenoxyethoxy)-1H-imidazo[4,5-c]quinolin-4-amine as a light tan solid, mp 237-239° C.

MS (APCI) m/z 335 (M+H$^+$);

Anal. calcd for $C_{19}H_{18}N_4O_2 \cdot 0.10H_2O$: C, 67.88; H, 5.46; N, 16.66. Found: C, 67.52; H, 5.34; N, 16.51.

Example 32

1-Phenoxy-2-propyl-1H-imidazo[4,5-c]quinolin-4-amine

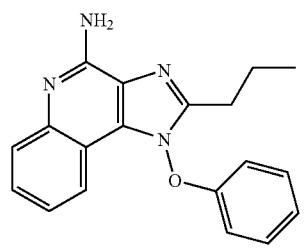

Part A

The method of Part B of Example 20 was followed using N-(4-chloroquinolin-3-yl)butyramide (3.5 g, 14 mmol) in lieu of 4-chloroquinolin-3-ylformamide and O-phenylhydroxylamine hydrochloride (2.3 g, 16 mmol) in lieu of O-ethylhydroxylamine hydrochloride in isopropanol (100 mL). Chromatographic purification was carried out eluting with 5% methanol in dichloromethane containing 2 mL of aqueous ammonium hydroxide per liter of eluent to provide 1.58 g of 1-phenoxy-2-propyl-1H-imidazo[4,5-c]quinoline as a brown, foamy solid.

Part B

The method described in Part C of Example 18 was used to oxidize and aminate 1-phenoxy-2-propyl-1H-imidazo[4,5-c]quinoline (1.58 g, 5.21 mmol) with the modification that chromatographic purification was carried out eluting with 5% methanol in dichloromethane containing 2 mL of aqueous ammonium hydroxide per liter of eluent. Without further purification, 1-phenoxy-2-propyl-1H-imidazo[4,5-c]quinolin-4-amine was obtained.

HRMS (ESI) calcd for $C_{19}H_{18}N_4O+H^+$: 319.1559. Found 319.1563.

Example 33

2-[(4-Amino-2-propyl-1H-imidazo[4,5-c]quinolin-1-yl)oxy]acetamide

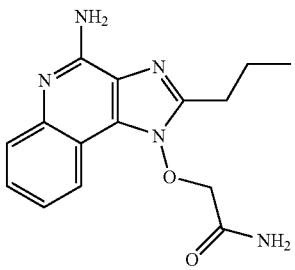

Part A

A solution of N-(4-chloroquinolin-3-yl)butyramide (20.0 g, 80.4 mmol) and O-benzylhydroxylamine hydrochloride (16.0 g, 0.100 mol) in ethanol (150 mL) was heated at reflux overnight and allowed to cool to room temperature. A precipitate was present, and the mixture was cooled to approximately 0° C. The precipitate was collected by filtration and purified by column chromatography on silica gel (eluting with 5% methanol in dichloromethane containing 3 mL of aqueous ammonium hydroxide per liter of eluent) to provide 1-(benzyloxy)-2-propyl-1H-imidazo[4,5-c]quinoline and 2-propyl-1H-imidazo[4,5-c]quinolin-1-ol.

Part B

A solution of 2-propyl-1H-imidazo[4,5-c]quinolin-1-ol (2.0 g, 8.8 mmol), bromoacetamide (1.9 g, 14 mmol), and triethylamine (2.8 mL, 0.020 mol) in THF (100 mL) was heated at reflux overnight. The solvent was removed under reduced pressure, and dichloromethane (75 mL) and saturated aqueous sodium bicarbonate (25 mL) were added to the residue. The resulting mixture was filtered to provide 2.1 g of 2-[(2-propyl-1H-imidazo[4,5-c]quinolin-1-yl)oxy]acetamide as a solid. The organic layer was separated, and methanol was added until all solids were dissolved. The solution was then dried over potassium carbonate, filtered, and concentrated under reduced pressure to provide an additional 0.13 g of material.

Part C

A solution of 2-[(2-propyl-1H-imidazo[4,5-c]quinolin-1-yl)oxy]acetamide (2.7 g, 9.5 mmol) in dichloromethane (100 mL) was cooled to approximately 0° C., and 3-chloroperoxybenzoic acid (3.2 g of approximately 77% pure material, 14 mmol) was added. The reaction was stirred for ten minutes at 0° C. and for one hour at room temperature. An analysis by LC/MS indicated that no reaction had occurred; the starting material was very insoluble. THF (40 mL) was added, and the reaction was stirred for 23 hours. An analysis by LC/MS indicated the presence of starting material, and dichloromethane (500 mL) was added. The reaction was stirred for seven hours, was allowed to stand for three days, and then was concentrated under reduced pressure to provide 2-[(5-oxido-2-propyl-1H-imidazo[4,5-c]quinolin-1-yl)oxy]acetamide.

Part D

A suspension of the material from Part C in dichloromethane (100 mL) was cooled to approximately 0° C. With stirring, concentrated ammonium hydroxide (35 mL) was added, and then a solution of benzenesulfonyl chloride (2.1 mL, 17 mmol) in dichloromethane (15 mL) was added dropwise. When the addition was complete, the reaction was stirred for three hours at room temperature and concentrated under reduced pressure. Saturated aqueous sodium bicarbonate (100 mL) was added to the residue, and the mixture was filtered to provide a tan solid. The solid was washed with saturated aqueous sodium bicarbonate (100 mL), recrystallized three times from methanol/water, dried overnight in a vacuum oven at 70° C., and recrystallized again from methanol/water to provide 2-[(4-amino-2-propyl-1H-imidazo[4,5-c]quinolin-1-yl)oxy]acetamide as tan needles, mp 192-194° C. MS (APCI) m/z 300 (M+H+); Anal. calcd for $C_{15}H_{17}N_5O_2$: C, 60.19; H, 5.72; N, 23.40. Found: C, 59.99; H, 5.46; N, 23.33.

HRMS (ESI) calcd for $C_{15}H_{17}N_5O_2+H^+$: 300.1461. Found 300.1455.

Example 34

2-Butyl-1-isopropoxy-1H-imidazo[4,5-c][1,5]naphthyridin-4-amine

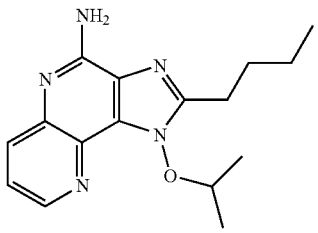

Part A

3-Nitro[1,5]naphthyridin-4-ol (40 g, 0.2 mol) was dissolved in water (80 mL) and triethylamine (60 mL), and the solution was added to a Parr vessel. Platinum on carbon (1.0 g of 5%) was added, and the mixture was shaken under hydrogen pressure (40 psi, $2.8\times10^5$ Pa) overnight. The vessel was pressurized again, and the mixture was shaken under hydrogen pressure for four hours. The vessel was purged with nitrogen, and the reaction mixture was filtered through a layer of CELITE filter agent. The filter cake was washed with water and methanol, and the filtrate was concentrated under reduced pressure to a volume of 150 mL. A precipitate formed and was isolated by filtration to provide 24.6 g of 3-amino[1,5]naphthyridin-4-ol as a yellow solid. The filter cake was washed again with water (500 mL at 80° C.), and the filtrate was concentrated to a volume of 100 mL. A precipitate formed and was isolated by filtration to provide an additional 10.7 g of 3-amino[1,5]naphthyridin-4-ol as a yellow solid.

Part B

A solution of valeryl chloride (4.4 mL, 37 mmol) in dichloromethane (25 mL) was added dropwise to a stirred suspension of 3-amino[1,5]naphthyridin-4-ol (5.0 g, 31 mmol) and triethylamine (6.6 mL, 47 mmol) in dichloromethane (100 mL), and the reaction was stirred for three days at room temperature. An analysis by LC/MS indicated the reaction was complete after 1.5 hours. The volatiles were removed under reduced pressure, and the residue was stirred with water (100 mL) for 15 minutes. The resulting solid was isolated by filtration and washed with water (100 mL) and diethyl ether (4×50 mL) to provide 5.35 g of N-(4-hydroxy[1,5]naphthyridin-3-yl)pentanamide.

Part C

A mixture of N-(4-hydroxy[1,5]naphthyridin-3-yl)pentanamide (2.5 g, 11 mmol), N-phenyl-bis(trifluoromethanesulfonimide) (4.6 g, 13 mmol), and triethylamine (2.2 mL, 16 mmol) in DMF (25 mL) was stirred at room temperature for one hour, heated at 75° C. for one hour, and stirred at room temperature for three days. An analysis by LC/MS indicated the presence of starting material, and the reaction was heated at 75° C. overnight and allowed to cool to room temperature. The mixture was poured onto ice (200 g) and stirred for one hour. A solid was present and was collected by filtration. The filtrate was concentrated under reduced pressure to provide 2.7 g of 3-(pentanoylamino)[1,5]naphthyridin-4-yl trifluoromethanesulfonate as a brown oil.

Part D

A solution of 3-(pentanoylamino)[1,5]naphthyridin-4-yl trifluoromethanesulfonate (2.7 g, 7.2 mmol), O-isopropylhydroxylamine hydrochloride (1.1 g, 9.9 mmol), and isopropanol (50 mL) was heated at reflux for six hours, allowed to cool to room temperature, stirred overnight, and concentrated under reduced pressure. The residue was stirred with dichloromethane (100 mL) and saturated aqueous sodium carbonate (50 mL) for 15 minutes. The organic layer was separated and dried over potassium carbonate, filtered, and concentrated under reduced pressure. The crude product (2.3 g) was purified by column chromatography on silica gel (eluting with 5% methanol in dichloromethane containing 2 mL of aqueous ammonium hydroxide per liter of eluent) to provide 0.40 g of 2-butyl-1-isopropoxy-1H-imidazo[4,5-c][1,5]naphthyridine as an oil.

Part E

A solution of 2-butyl-1-isopropoxy-1H-imidazo[4,5-c][1,5]naphthyridine (0.40 g, 1.4 mmol) in dichloromethane (25 mL) was cooled to approximately 0° C., and 3-chloroperoxybenzoic acid (0.42 g of approximately 77% pure material, 1.9 mmol) was added. The reaction was stirred for ten minutes at 0° C., stirred for 1.5 hours at room temperature, and then stirred with saturated aqueous sodium bicarbonate (25 mL) for 15 minutes. The organic layer was separated and dried over potassium carbonate, filtered, and concentrated under reduced pressure to provide 0.42 g of 2-butyl-1-isopropoxy-5-oxido-1H-imidazo[4,5-c][1,5]naphthyridine as a yellow oil.

Part F

Trichloroacetyl isocyanate (0.21 mL, 1.8 mmol) was added to a chilled (ice bath) solution of the N-oxide from Part E in dichloromethane (20 mL). After 15 minutes the ice bath was removed and the reaction mixture was stirred at ambient temperature. After 1 hour methanol (5 mL) was added. The reaction mixture was stirred for 5 minutes and then concentrated under reduced pressure. The residue was combined with methanol (10 mL) and sodium methoxide (0.5 mL of 25% in methanol). The reaction mixture was stirred over night and then concentrated under reduced pressure to provide 2-butyl-1-isopropoxy-1H-imidazo[4,5-c][1,5]naphthyridin-4-amine. HRMS (ESI) calcd for $C_{16}H_{21}N_5O+H^+$: 300.1824. Found 300.1824

Exemplary Compounds

Certain exemplary compounds, including some of those described above in the Examples, have the following Formulas (LII, LIII, LIV, LV, LVI, or LVII) and the following $R_1$ and $R_2$ substituents, wherein each line of the table is matched with Formula LII, LIII, LIV, LV, LVI, or LVII to represent a specific compound.

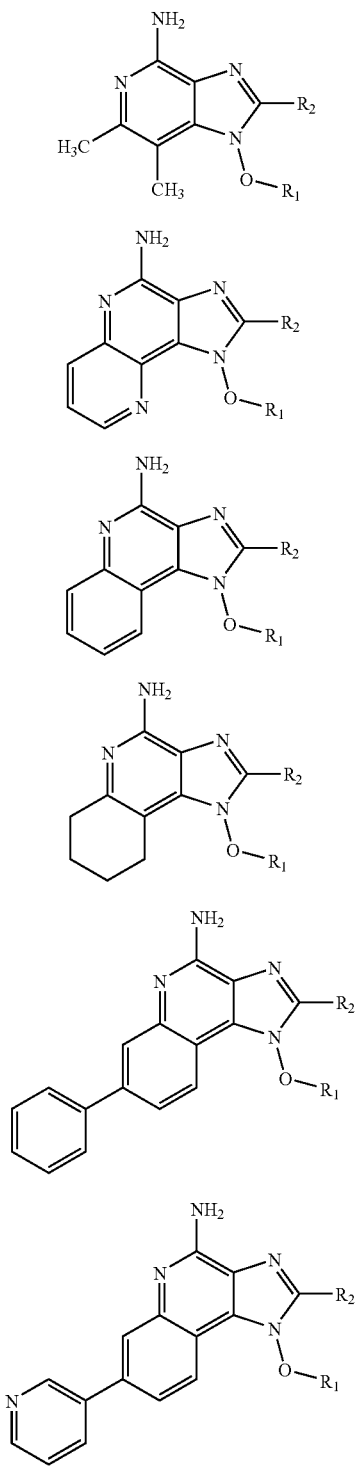

| R₁ | R₂ |
|---|---|
| methyl | hydrogen |
| methyl | methyl |
| methyl | ethyl |

-continued

| | R₁ | R₂ |
|---|---|---|
| | methyl | n-propyl |
| | methyl | n-butyl |
| | methyl | methoxymethyl |
| | methyl | ethoxymethyl |
| | methyl | 2-methoxyethyl |
| | methyl | hydroxymethyl |
| | methyl | 2-hydroxyethyl |
| | methyl | 3-hydroxypropyl |
| | methyl | isopropyl |
| | methyl | sec-butyl |
| | methyl | tert-butyl |
| | methyl | isopropenyl |
| | methyl | cyclopentyl |
| | methyl | cyclohexyl |
| | methyl | 1-hydroxyethyl |
| | methyl | 2-hydroxy-1-methylethyl |
| | methyl | tetrahydrofuran-3-yl |
| | methyl | tetrahydropyran-4-yl |
| | ethyl | hydrogen |
| | ethyl | methyl |
| | ethyl | ethyl |
| | ethyl | n-propyl |
| | ethyl | n-butyl |
| | ethyl | methoxymethyl |
| | ethyl | ethoxymethyl |
| | ethyl | 2-methoxyethyl |
| | ethyl | hydroxymethyl |
| | ethyl | 2-hydroxyethyl |
| | ethyl | 3-hydroxypropyl |
| | ethyl | isopropyl |
| | ethyl | sec-butyl |
| | ethyl | tert-butyl |
| | ethyl | isopropenyl |
| | ethyl | cyclopentyl |
| | ethyl | cyclohexyl |
| | ethyl | 1-hydroxyethyl |
| | ethyl | 2-hydroxy-1-methylethyl |
| | ethyl | tetrahydrofuran-3-yl |
| | ethyl | tetrahydropyran-4-yl |
| | n-propyl | hydrogen |
| | n-propyl | methyl |
| | n-propyl | ethyl |
| | n-propyl | n-propyl |
| | n-propyl | n-butyl |
| | n-propyl | methoxymethyl |
| | n-propyl | ethoxymethyl |
| | n-propyl | 2-methoxyethyl |
| | n-propyl | hydroxymethyl |
| | n-propyl | 2-hydroxyethyl |
| | n-propyl | 3-hydroxypropyl |
| | n-propyl | isopropyl |
| | n-propyl | sec-butyl |
| | n-propyl | tert-butyl |
| | n-propyl | isopropenyl |
| | n-propyl | cyclopentyl |
| | n-propyl | cyclohexyl |
| | n-propyl | 1-hydroxyethyl |
| | n-propyl | 2-hydroxy-1-methylethyl |
| | n-propyl | tetrahydrofuran-3-yl |
| | n-propyl | tetrahydropyran-4-yl |
| | isopropyl | hydrogen |
| | isopropyl | methyl |
| | isopropyl | ethyl |
| | isopropyl | n-propyl |
| | isopropyl | n-butyl |
| | isopropyl | methoxymethyl |
| | isopropyl | ethoxymethyl |
| | isopropyl | 2-methoxyethyl |
| | isopropyl | hydroxymethyl |
| | isopropyl | 2-hydroxyethyl |
| | isopropyl | 3-hydroxypropyl |
| | isopropyl | isopropyl |
| | isopropyl | sec-butyl |
| | isopropyl | tert-butyl |
| | isopropyl | isopropenyl |
| | isopropyl | cyclopentyl |
| | isopropyl | cyclohexyl |

-continued

| R₁ | R₂ |
|---|---|
| isopropyl | 1-hydroxyethyl |
| isopropyl | 2-hydroxy-1-methylethyl |
| isopropyl | tetrahydrofuran-3-yl |
| isopropyl | tetrahydropyran-4-yl |
| n-butyl | hydrogen |
| n-butyl | methyl |
| n-butyl | ethyl |
| n-butyl | n-propyl |
| n-butyl | n-butyl |
| n-butyl | methoxymethyl |
| n-butyl | ethoxymethyl |
| n-butyl | 2-methoxyethyl |
| n-butyl | hydroxymethyl |
| n-butyl | 2-hydroxyethyl |
| n-butyl | 3-hydroxypropyl |
| n-butyl | isopropyl |
| n-butyl | sec-butyl |
| n-butyl | tert-butyl |
| n-butyl | isopropenyl |
| n-butyl | cyclopentyl |
| n-butyl | cyclohexyl |
| n-butyl | 1-hydroxyethyl |
| n-butyl | 2-hydroxy-1-methylethyl |
| n-butyl | tetrahydrofuran-3-yl |
| n-butyl | tetrahydropyran-4-yl |
| isobutyl | hydrogen |
| isobutyl | methyl |
| isobutyl | ethyl |
| isobutyl | n-propyl |
| isobutyl | n-butyl |
| isobutyl | methoxymethyl |
| isobutyl | ethoxymethyl |
| isobutyl | 2-methoxyethyl |
| isobutyl | hydroxymethyl |
| isobutyl | 2-hydroxyethyl |
| isobutyl | 3-hydroxypropyl |
| isobutyl | isopropyl |
| isobutyl | sec-butyl |
| isobutyl | tert-butyl |
| isobutyl | isopropenyl |
| isobutyl | cyclopentyl |
| isobutyl | cyclohexyl |
| isobutyl | 1-hydroxyethyl |
| isobutyl | 2-hydroxy-1-methylethyl |
| isobutyl | tetrahydrofuran-3-yl |
| isobutyl | tetrahydropyran-4-yl |
| cyclohexyl | hydrogen |
| cyclohexyl | methyl |
| cyclohexyl | ethyl |
| cyclohexyl | n-propyl |
| cyclohexyl | n-butyl |
| cyclohexyl | methoxymethyl |
| cyclohexyl | ethoxymethyl |
| cyclohexyl | 2-methoxyethyl |
| cyclohexyl | hydroxymethyl |
| cyclohexyl | 2-hydroxyethyl |
| cyclohexyl | 3-hydroxypropyl |
| cyclohexyl | isopropyl |
| cyclohexyl | sec-butyl |
| cyclohexyl | tert-butyl |
| cyclohexyl | isopropenyl |
| cyclohexyl | cyclopentyl |
| cyclohexyl | cyclohexyl |
| cyclohexyl | 1-hydroxyethyl |
| cyclohexyl | 2-hydroxy-1-methylethyl |
| cyclohexyl | tetrahydrofuran-3-yl |
| cyclohexyl | tetrahydropyran-4-yl |
| benzyl | hydrogen |
| benzyl | methyl |
| benzyl | ethyl |
| benzyl | n-propyl |
| benzyl | n-butyl |
| benzyl | methoxymethyl |
| benzyl | ethoxymethyl |
| benzyl | 2-methoxyethyl |
| benzyl | hydroxymethyl |
| benzyl | 2-hydroxyethyl |

-continued

| R₁ | R₂ |
|---|---|
| benzyl | 3-hydroxypropyl |
| benzyl | isopropyl |
| benzyl | sec-butyl |
| benzyl | tert-butyl |
| benzyl | isopropenyl |
| benzyl | cyclopentyl |
| benzyl | cyclohexyl |
| benzyl | 1-hydroxyethyl |
| benzyl | 2-hydroxy-1-methylethyl |
| benzyl | tetrahydrofuran-3-yl |
| benzyl | tetrahydropyran-4-yl |
| phenyl | hydrogen |
| phenyl | methyl |
| phenyl | ethyl |
| phenyl | n-propyl |
| phenyl | n-butyl |
| phenyl | methoxymethyl |
| phenyl | ethoxymethyl |
| phenyl | 2-methoxyethyl |
| phenyl | hydroxymethyl |
| phenyl | 2-hydroxyethyl |
| phenyl | 3-hydroxypropyl |
| phenyl | isopropyl |
| phenyl | sec-butyl |
| phenyl | tert-butyl |
| phenyl | isopropenyl |
| phenyl | cyclopentyl |
| phenyl | cyclohexyl |
| phenyl | 1-hydroxyethyl |
| phenyl | 2-hydroxy-1-methylethyl |
| phenyl | tetrahydrofuran-3-yl |
| phenyl | tetrahydropyran-4-yl |
| 3-phenylpropyl | hydrogen |
| 3-phenylpropyl | methyl |
| 3-phenylpropyl | ethyl |
| 3-phenylpropyl | n-propyl |
| 3-phenylpropyl | n-butyl |
| 3-phenylpropyl | methoxymethyl |
| 3-phenylpropyl | ethoxymethyl |
| 3-phenylpropyl | 2-methoxyethyl |
| 3-phenylpropyl | hydroxymethyl |
| 3-phenylpropyl | 2-hydroxyethyl |
| 3-phenylpropyl | 3-hydroxypropyl |
| 3-phenylpropyl | isopropyl |
| 3-phenylpropyl | sec-butyl |
| 3-phenylpropyl | tert-butyl |
| 3-phenylpropyl | isopropenyl |
| 3-phenylpropyl | cyclopentyl |
| 3-phenylpropyl | cyclohexyl |
| 3-phenylpropyl | 1-hydroxyethyl |
| 3-phenylpropyl | 2-hydroxy-1-methylethyl |
| 3-phenylpropyl | tetrahydrofuran-3-yl |
| 3-phenylpropyl | tetrahydropyran-4-yl |
| (pyridin-3-yl)methyl | hydrogen |
| (pyridin-3-yl)methyl | methyl |
| (pyridin-3-yl)methyl | ethyl |
| (pyridin-3-yl)methyl | n-propyl |
| (pyridin-3-yl)methyl | n-butyl |
| (pyridin-3-yl)methyl | methoxymethyl |
| (pyridin-3-yl)methyl | ethoxymethyl |
| (pyridin-3-yl)methyl | 2-methoxyethyl |
| (pyridin-3-yl)methyl | hydroxymethyl |
| (pyridin-3-yl)methyl | 2-hydroxyethyl |
| (pyridin-3-yl)methyl | 3-hydroxypropyl |
| (pyridin-3-yl)methyl | isopropyl |
| (pyridin-3-yl)methyl | sec-butyl |
| (pyridin-3-yl)methyl | tert-butyl |
| (pyridin-3-yl)methyl | isopropenyl |
| (pyridin-3-yl)methyl | cyclopentyl |
| (pyridin-3-yl)methyl | cyclohexyl |
| (pyridin-3-yl)methyl | 1-hydroxyethyl |
| (pyridin-3-yl)methyl | 2-hydroxy-1-methylethyl |
| (pyridin-3-yl)methyl | tetrahydrofuran-3-yl |
| (pyridin-3-yl)methyl | tetrahydropyran-4-yl |
| 3-[(methanesulfonyl)amino]propyl | hydrogen |
| 3-[(methanesulfonyl)amino]propyl | methyl |
| 3-[(methanesulfonyl)amino]propyl | ethyl |

-continued

| R₁ | R₂ |
|---|---|
| 3-[(methanesulfonyl)amino]propyl | n-propyl |
| 3-[(methanesulfonyl)amino]propyl | n-butyl |
| 3-[(methanesulfonyl)amino]propyl | methoxymethyl |
| 3-[(methanesulfonyl)amino]propyl | ethoxymethyl |
| 3 [(methanesulfonyl)amino]propyl | 2-methoxyethyl |
| 3-[(methanesulfonyl)amino]propyl | hydroxymethyl |
| 3-[(methanesulfonyl)amino]propyl | 2-hydroxyethyl |
| 3-[(methanesulfonyl)amino]propyl | 3-hydroxypropyl |
| 3-[(methanesulfonyl)amino]propyl | isopropyl |
| 3-[(methanesulfonyl)amino]propyl | sec-butyl |
| 3-[(methanesulfonyl)amino]propyl | tert-butyl |
| 3-[(methanesulfonyl)amino]propyl | isopropenyl |
| 3-[(methanesulfonyl)amino]propyl | cyclopentyl |
| 3-[(methanesulfonyl)amino]propyl | cyclohexyl |
| 3-[(methanesulfonyl)amino]propyl | 1-hydroxyethyl |
| 3-[(methanesulfonyl)amino]propyl | 2-hydroxy-1-methylethyl |
| 3-[(methanesulfonyl)amino]propyl | tetrahydrofuran-3-yl |
| 3-[(methanesulfonyl)amino]propyl | tetrahydropyran-4-yl |
| 3-(acetylamino)propyl | hydrogen |
| 3-(acetylamino)propyl | methyl |
| 3-(acetylamino)propyl | ethyl |
| 3-(acetylamino)propyl | n-propyl |
| 3-(acetylamino)propyl | n-butyl |
| 3-(acetylamino)propyl | methoxymethyl |
| 3-(acetylamino)propyl | ethoxymethyl |
| 3-(acetylamino)propyl | 2-methoxyethyl |
| 3-(acetylamino)propyl | hydroxymethyl |
| 3-(acetylamino)propyl | 2-hydroxyethyl |
| 3-(acetylamino)propyl | 3-hydroxypropyl |
| 3-(acetylamino)propyl | isopropyl |
| 3-(acetylamino)propyl | sec-butyl |
| 3-(acetylamino)propyl | tert-butyl |
| 3-(acetylamino)propyl | isopropenyl |
| 3-(acetylamino)propyl | cyclopentyl |
| 3-(acetylamino)propyl | cyclohexyl |
| 3-(acetylamino)propyl | 1-hydroxyethyl |
| 3-(acetylamino)propyl | 2-hydroxy-1-methylethyl |
| 3-(acetylamino)propyl | tetrahydrofuran-3-yl |
| 3-(acetylamino)propyl | tetrahydropyran-4-yl |
| 3-[(isopropylcarbonyl)amino]propyl | hydrogen |
| 3-[(isopropylcarbonyl)amino]propyl | methyl |
| 3-[(isopropylcarbonyl)amino]propyl | ethyl |
| 3-[(isopropylcarbonyl)amino]propyl | n-propyl |
| 3-[(isopropylcarbonyl)amino]propyl | n-butyl |
| 3-[(isopropylcarbonyl)amino]propyl | methoxymethyl |
| 3-[(isopropylcarbonyl)amino]propyl | ethoxymethyl |
| 3-[(isopropylcarbonyl)amino]propyl | 2-methoxyethyl |
| 3-[(isopropylcarbonyl)amino]propyl | hydroxymethyl |
| 3-[(isopropylcarbonyl)amino]propyl | 2-hydroxyethyl |
| 3-[(isopropylcarbonyl)amino]propyl | 3-hydroxypropyl |
| 3-[(isopropylcarbonyl)amino]propyl | isopropyl |
| 3-[(isopropylcarbonyl)amino]propyl | sec-butyl |
| 3-[(isopropylcarbonyl)amino]propyl | tert-butyl |
| 3-[(isopropylcarbonyl)amino]propyl | isopropenyl |
| 3-[(isopropylcarbonyl)amino]propyl | cyclopentyl |
| 3-[(isopropylcarbonyl)amino]propyl | cyclohexyl |
| 3-[(isopropylcarbonyl)amino]propyl | 1-hydroxyethyl |
| 3-[(isopropylcarbonyl)amino]propyl | 2-hydroxy-1-methylethyl |
| 3-[(isopropylcarbonyl)amino]propyl | tetrahydrofuran-3-yl |
| 3-[(isopropylcarbonyl)amino]propyl | tetrahydropyran-4-yl |
| 3-[(cyclohexylcarbonyl)amino]propyl | hydrogen |
| 3-[(cyclohexylcarbonyl)amino]propyl | methyl |
| 3-[(cyclohexylcarbonyl)amino]propyl | ethyl |
| 3-[(cyclohexylcarbonyl)amino]propyl | n-propyl |
| 3-[(cyclohexylcarbonyl)amino]propyl | n-butyl |
| 3-[(cyclohexylcarbonyl)amino]propyl | methoxymethyl |
| 3-[(cyclohexylcarbonyl)amino]propyl | ethoxymethyl |
| 3-[(cyclohexylcarbonyl)amino]propyl | 2-methoxyethyl |
| 3-[(cyclohexylcarbonyl)amino]propyl | hydroxymethyl |
| 3-[(cyclohexylcarbonyl)amino]propyl | 2-hydroxyethyl |
| 3-[(cyclohexylcarbonyl)amino]propyl | 3-hydroxypropyl |
| 3-[(cyclohexylcarbonyl)amino]propyl | isopropyl |
| 3-[(cyclohexylcarbonyl)amino]propyl | sec-butyl |
| 3-[(cyclohexylcarbonyl)amino]propyl | tert-butyl |
| 3-[(cyclohexylcarbonyl)amino]propyl | isopropenyl |
| 3-[(cyclohexylcarbonyl)amino]propyl | cyclopentyl |
| 3-[(cyclohexylcarbonyl)amino]propyl | cyclohexyl |

-continued

| R₁ | R₂ |
|---|---|
| 3-[(cyclohexylcarbonyl)amino]propyl | 1-hydroxyethyl |
| 3-[(cyclohexylcarbonyl)amino]propyl | 2-hydroxy-1-methylethyl |
| 3-[(cyclohexylcarbonyl)amino]propyl | tetrahydrofuran-3-yl |
| 3-[(cyclohexylcarbonyl)amino]propyl | tetrahydropyran-4-yl |
| 3-[(morpholin-4-ylcarbonyl)amino]propyl | hydrogen |
| 3-[(morpholin-4-ylcarbonyl)amino]propyl | methyl |
| 3-[(morpholin-4-ylcarbonyl)amino]propyl | ethyl |
| 3-[(morpholin-4-ylcarbonyl)amino]propyl | n-propyl |
| 3-[(morpholin-4-ylcarbonyl)amino]propyl | n-butyl |
| 3-[(morpholin-4-ylcarbonyl)amino]propyl | methoxymethyl |
| 3-[(morpholin-4-ylcarbonyl)amino]propyl | ethoxymethyl |
| 3-[(morpholin-4-ylcarbonyl)amino]propyl | 2-methoxyethyl |
| 3-[(morpholin-4-ylcarbonyl)amino]propyl | hydroxymethyl |
| 3-[(morpholin-4-ylcarbonyl)amino]propyl | 2-hydroxyethyl |
| 3-[(morpholin-4-ylcarbonyl)amino]propyl | 3-hydroxypropyl |
| 3-[(morpholin-4-ylcarbonyl)amino]propyl | isopropyl |
| 3-[(morpholin-4-ylcarbonyl)amino]propyl | sec-butyl |
| 3-[(morpholin-4-ylcarbonyl)amino]propyl | tert-butyl |
| 3-[(morpholin-4-ylcarbonyl)amino]propyl | isopropenyl |
| 3-[(morpholin-4-ylcarbonyl)amino]propyl | cyclopentyl |
| 3-[(morpholin-4-ylcarbonyl)amino]propyl | cyclohexyl |
| 3-[(morpholin-4-ylcarbonyl)amino]propyl | 1-hydroxyethyl |
| 3-[(morpholin-4-ylcarbonyl)amino]propyl | 2-hydroxy-1-methylethyl |
| 3-[(morpholin-4-ylcarbonyl)amino]propyl | tetrahydrofuran-3-yl |
| 3-[(morpholin-4-ylcarbonyl)amino]propyl | tetrahydropyran-4-yl |
| 3-{[(isopropylamino)carbonyl]amino}propyl | hydrogen |
| 3-{[(isopropylamino)carbonyl]amino}propyl | methyl |
| 3-{[(isopropylamino)carbonyl]amino}propyl | ethyl |
| 3-{[(isopropylamino)carbonyl]amino}propyl | n-propyl |
| 3-{[(isopropylamino)carbonyl]amino}propyl | n-butyl |
| 3-{[(isopropylamino)carbonyl]amino}propyl | methoxymethyl |
| 3-{[(isopropylamino)carbonyl]amino}propyl | ethoxymethyl |
| 3-{[(isopropylamino)carbonyl]amino}propyl | 2-methoxyethyl |
| 3-{[(isopropylamino)carbonyl]amino}propyl | hydroxymethyl |
| 3-{[(isopropylamino)carbonyl]amino}propyl | 2-hydroxyethyl |
| 3-{[(isopropylamino)carbonyl]amino}propyl | 3-hydroxypropyl |
| 3-{[(isopropylamino)carbonyl]amino}propyl | isopropyl |
| 3-{[(isopropylamino)carbonyl]amino}propyl | sec-butyl |
| 3-{[(isopropylamino)carbonyl]amino}propyl | tert-butyl |
| 3-{[(isopropylamino)carbonyl]amino}propyl | isopropenyl |
| 3-{[(isopropylamino)carbonyl]amino}propyl | cyclopentyl |
| 3-{[(isopropylamino)carbonyl]amino}propyl | cyclohexyl |
| 3-{[(isopropylamino)carbonyl]amino}propyl | 1-hydroxyethyl |
| 3-{[(isopropylamino)carbonyl]amino}propyl | 2-hydroxy-1-methylethyl |
| 3-{[(isopropylamino)carbonyl]amino}propyl | tetrahydrofuran-3-yl |
| 3-{[(isopropylamino)carbonyl]amino}propyl | tetrahydropyran-4-yl |
| 2-(morpholin-4-yl)-2-oxoethyl | hydrogen |
| 2-(morpholin-4-yl)-2-oxoethyl | methyl |
| 2-(morpholin-4-yl)-2-oxoethyl | ethyl |
| 2-(morpholin-4-yl)-2-oxoethyl | n-propyl |
| 2-(morpholin-4-yl)-2-oxoethyl | n-butyl |
| 2-(morpholin-4-yl)-2-oxoethyl | methoxymethyl |
| 2-(morpholin-4-yl)-2-oxoethyl | ethoxymethyl |
| 2-(morpholin-4-yl)-2-oxoethyl | 2-methoxyethyl |
| 2-(morpholin-4-yl)-2-oxoethyl | hydroxymethyl |
| 2-(morpholin-4-yl)-2-oxoethyl | 2-hydroxyethyl |
| 2-(morpholin-4-yl)-2-oxoethyl | 3-hydroxypropyl |
| 2-(morpholin-4-yl)-2-oxoethyl | isopropyl |
| 2-(morpholin-4-yl)-2-oxoethyl | sec-butyl |
| 2-(morpholin-4-yl)-2-oxoethyl | tert-butyl |
| 2-(morpholin-4-yl)-2-oxoethyl | isopropenyl |
| 2-(morpholin-4-yl)-2-oxoethyl | cyclopentyl |
| 2-(morpholin-4-yl)-2-oxoethyl | cyclohexyl |
| 2-(morpholin-4-yl)-2-oxoethyl | 1-hydroxyethyl |
| 2-(morpholin-4-yl)-2-oxoethyl | 2-hydroxy-1-methylethyl |
| 2-(morpholin-4-yl)-2-oxoethyl | tetrahydrofuran-3-yl |
| 2-(morpholin-4-yl)-2-oxoethyl | tetrahydropyran-4-yl |

Compounds of the invention have been found to modulate cytokine biosynthesis by inducing the production of interferon α and/or tumor necrosis factor α in human cells when tested using the method described below.

Cytokine Induction in Human Cells

An in vitro human blood cell system is used to assess cytokine induction. Activity is based on the measurement of interferon (α) and tumor necrosis factor (α) (IFN-α and TNF-α, respectively) secreted into culture media as described by Testerman et al. in "Cytokine Induction by the Immunomodulators Imiquimod and S-27609," *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4\times10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 μM. Controls include cell samples with media only, cell samples with DMSO only (no compound), and cell samples with reference compound.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (usually 30-0.014 μM). The final concentration of PBMC suspension is $2\times10^6$ cells/mL. The plates are covered with sterile plastic lids, mixed gently and then incubated for 18 hours to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30° C. to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype colorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

Cytokine Induction in Human Cells

High Throughput Screen

The CYTOKINE INDUCTION IN HUMAN CELLS test method described above was modified as follows for high throughput screening.

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4\times10^6$ cells/mL in RPMI complete (2-fold the final cell density). The PBMC suspension is added to 96-well flat bottom sterile tissue culture plates.

Compound Preparation

The compounds are solubilized in dimethyl sulfoxide (DMSO). The compounds are generally tested at concentrations ranging from 30-0.014 μM. Controls include cell samples with media only, cell samples with DMSO only (no compound), and cell samples with a reference compound 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) on each plate. The solution of test compound is added at 7.5 mM to the first well of a dosing plate and serial 3 fold dilutions are made for the 7 subsequent concentrations in DMSO. RPMI Complete media is then added to the test compound dilutions in order to reach a final compound concentration of 2-fold higher (60-0.028 µM) than the final tested concentration range.

Incubation

Compound solution is then added to the wells containing the PBMC suspension bringing the test compound concentrations to the desired range (usually 30 µM-0.014 µM) and the DMSO concentration to 0.4%. The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200 g) at 4° C. 4-plex Human Panel MSD MULTI-SPOT 96-well plates are pre-coated with the appropriate capture antibodies by MesoScale Discovery, Inc. (MSD, Gaithersburg, Md.). The cell-free culture supernatants are removed and transferred to the MSD plates. Fresh samples are typically tested, although they may be maintained at −30° C. to −70° C. until analysis.

Interferon-α and Tumor Necrosis Factor-α Analysis

MSD MULTI-SPOT plates contain within each well capture antibodies for human TNF-α and human IFN-α that have been pre-coated on specific spots. Each well contains four spots: one human TNF-α capture antibody (MSD) spot, one human IFN-α capture antibody (PBL Biomedical Laboratories, Piscataway, N.J.) spot, and two inactive bovine serum albumin spots. The human TNF-α capture and detection antibody pair is from MesoScale Discovery. The human IFN-α multi-subtype antibody (PBL Biomedical Laboratories) captures all IFN-α subtypes except IFN-α F (IFNA21). Standards consist of recombinant human TNF-α (R&D Systems, Minneapolis, Minn.) and IFN-α (PBL Biomedical Laboratories). Samples and separate standards are added at the time of analysis to each MSD plate. Two human IFN-α detection antibodies (Cat. Nos. 21112 & 21100, PBL) are used in a two to one ratio (weight:weight) to each other to determine the IFN-α concentrations. The cytokine-specific detection antibodies are labeled with the SULFO-TAG reagent (MSD). After adding the SULFO-TAG labeled detection antibodies to the wells, each well's electrochemiluminescent levels are read using MSD's SECTOR HTS READER. Results are expressed in pg/mL upon calculation with known cytokine standards.

Assay Data and Analysis

In total, the data output of the assay consists of concentration values of TNF-α or IFN-α (y-axis) as a function of compound concentration (x-axis).

A plate-wise scaling is performed within a given experiment aimed at reducing plate-to-plate variability associated within the same experiment. First, the greater of the median DMSO (DMSO control wells) or the experimental background (usually 20 pg/mL for IFN-α and 40 pg/mL for TNF-α) is subtracted from each reading. Negative values that may result from background subtraction are set to zero. Each plate within a given experiment has a reference compound that serves as a control. This control is used to calculate a median expected area under the curve across all plates in the assay. A plate-wise scaling factor is calculated for each plate as a ratio of the area of the reference compound on the particular plate to the median expected area for the entire experiment. The data from each plate are then multiplied by the plate-wise scaling factor for all plates. Only data from plates bearing a scaling factor of between 0.5 and 2.0 (for both cytokines IFN-α, TNF-α) are reported. Data from plates with scaling factors outside the above-mentioned interval are retested until they bear scaling factors inside the above mentioned interval. The above method produces a scaling of the y-values without altering the shape of the curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91). The median expected area is the median area across all plates that are part of a given experiment.

A second scaling may also be performed to reduce inter-experiment variability (across multiple experiments). All background-subtracted values are multiplied by a single adjustment ratio to decrease experiment-to-experiment variability. The adjustment ratio is the area of the reference compound in the new experiment divided by the expected area of the reference compound based on an average of previous experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from an average of previous experiments.

The minimum effective concentration is calculated based on the background-subtracted, reference-adjusted results for a given experiment and compound. The minimum effective concentration (µmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

Certain compounds of the invention may modulate cytokine biosynthesis by inhibiting production of tumor necrosis factor α (TNF-α) when tested using the method described below.

TNF-α Inhibition in Mouse Cells

The mouse macrophage cell line Raw 264.7 is used to assess the ability of compounds to inhibit tumor necrosis factor-α (TNF-α) production upon stimulation by lipopolysaccharide (LPS).

Single Concentration Assay:

Blood Cell Preparation for Culture

Raw cells (ATCC) are harvested by gentle scraping and then counted. The cell suspension is brought to $3 \times 10^5$ cells/mL in RPMI with 10% fetal bovine serum (FBS). Cell suspension (100 µL) is added to 96-well flat bottom sterile tissues culture plates (Becton Dickinson Labware, Lincoln Park, N.J.). The final concentration of cells is $3 \times 10^4$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 5 µM. LPS (Lipopolysaccharide from *Salmonella typhimurium*, Sigma-Aldrich) is diluted with colorless RPMI to the $EC_{70}$ concentration as measured by a dose response assay.

Incubation

A solution of test compound (1 µl) is added to each well. The plates are mixed on a microtiter plate shaker for 1 minute and then placed in an incubator. Twenty minutes later the solution of LPS (1 µL, $EC_{70}$ concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

Dose Response Assay:

Blood Cell Preparation for Culture

Raw cells (ATCC) are harvested by gentle scraping and then counted. The cell suspension is brought to $4 \times 10^5$ cells/mL in RPMI with 10% FBS. Cell suspension (250 µL) is added to 48-well flat bottom sterile tissues culture plates (Costar, Cambridge, Mass.). The final concentration of cells is $1 \times 10^5$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 0.03, 0.1, 0.3, 1, 3, 5 and 10 µM. LPS (Lipopolysaccharide from *Salmonella typhimurium*, Sigma-Aldrich) is diluted with colorless RPMI to the $EC_{70}$ concentration as measured by dose response assay.

Incubation

A solution of test compound (200 µl) is added to each well. The plates are mixed on a microtiter plate shaker for 1 minute and then placed in an incubator. Twenty minutes later the solution of LPS (200 µL, $EC_{70}$ concentration approximately 10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-αconcentration is determined by ELISA using a mouse TNF-α kit (from Biosource International, Camarillo, Calif.). Results are expressed in pg/mL. TNF-α expression upon LPS stimulation alone is considered a 100% response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the following Formula II:

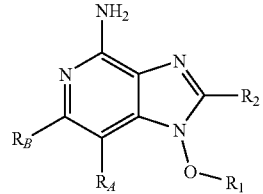

wherein:
$R_1$ is selected from the group consisting of:
—$R_4$,
—X—$R_5$,
—X—N($R_6$)—Y—$R_4$,
—X"—C($R_7$)—N($R_9$)—$R_4$,
—X—O—C($R_7$)—N($R_6$)—$R_4$,
—X—S(O)$_2$—N($R_6$)—$R_4$, and
—X—$R_4$;

$R_2$ is selected from the group consisting of:
hydrogen,
alkyl,
alkenyl,
aryl,
heteroaryl,
heterocyclyl,
alkyl-Z-alkylenyl,
aryl Z-alkylenyl,
alkenyl-Z-alkylenyl, and
alkyl or alkenyl substituted by one or more substituents selected from the group consisting of:
hydroxy,
halogen,
—N($R_6$)$_2$,
—C($R_7$)—N($R_6$)$_2$,
—S(O)$_2$—N($R_6$)$_2$,
—N($R_6$)—C($R_7$)—$C_{1-10}$ alkyl,
—N($R_6$)—S(O)$_2$—$C_{1-10}$ alkyl,
—C(O)—$C_{1-10}$ alkyl,
—C(O)—O—$C_{1-10}$ alkyl,
—$N_3$,
aryl,
heteroaryl,
heterocyclyl,
—C(O)-aryl,
—C(O)-heteroaryl,
—N($R_6$)—C($R_7$)-aryl,
—N($R_6$)—S(O)$_2$-aryl,
—O—C($R_7$)—$C_{1-10}$ alkyl,
—O—C($R_7$)-aryl,
—O—C($R_7$)—N($R_6$)—$C_{1-10}$ alkyl, and
—O—C($R_7$)—N($R_6$)-aryl;

$R_A$ and $R_B$ are each independently selected from the group consisting of:
hydrogen,
halogen,
alkyl,
alkenyl,
alkoxy,
alkylthio, and
—N($R_{12}$)$_2$;
or when taken together, $R_A$ and $R_B$ form a fused benzene or pyridine ring which is unsubstituted or substituted by one or more R groups, or substituted by one $R_3$ group, or substituted by one $R_3$ group and one R group, or substituted by one $R_3$ group and two R groups;

or when taken together, $R_A$ and $R_B$ form a fused cyclohexene or tetrahydropyridine ring which is unsubstituted or substituted by one or more R groups;

R is selected from the group consisting of:
halogen,
hydroxy,
alkyl,
alkenyl,
haloalkyl,
alkoxy,
alkylthio, and
—$N(R_{12})_2$;

$R_3$ is selected from the group consisting of:
-Z'$R_4$',
-Z'-X'—$R_4$',
-Z'-X'—Y'—$R_4$', and
-Z'-X'—$R_5$';

$R_4$ is selected from the group consisting of hydrogen, alkyl, alkenyl, alkynyl, aryl, arylalkylenyl, heteroaryl, and heterocyclyl wherein the alkyl, alkenyl, alkynyl, aryl, arylalkylenyl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when $R_4$ is a substituted alkyl group and the substituent contains a hetero atom which bonds directly to the alkyl group then the alkyl group contains at least two carbons between the substituent and the oxygen atom to which $R_1$ is bonded;

$R_5$ is selected from the group consisting of:

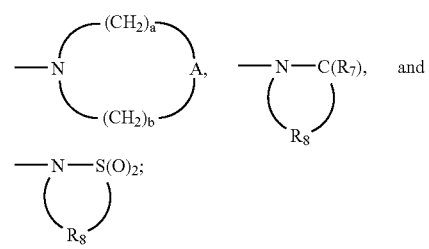

X is $C_{2-20}$ alkylene;
X" is $C_{1-20}$ alkylene;
Y is selected from the group consisting of —$C(R_7)$—, —$C(R_7)$—O—, —$S(O)_2$—, —$S(O)_2$—$N(R_6)$—, and —$C(R_7)$—$N(R_9)$—;
Z is selected from the group consisting of —O— and —$S(O)_{0-2}$—;
A is selected from the group consisting of —$CH(R_6)$—, —O—, —$N(R_6)$—, —$N(Y—R_4)$—, and —$N(X—N(R_6)—Y—R_4)$—;
a and b are independently integers from 1 to 4 with the proviso that when A is —O—, —$N(R_6)$—, —$N(Y—R_4)$—, or —$N(X—N(R_6)—Y—R_4)$— then a and b are independently integers from 2 to 4;
$R_4$' is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$' is selected from the group consisting of:

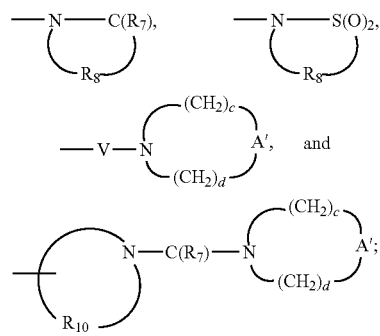

X' is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene, or heterocyclylene and optionally interrupted by one or more —O— groups;

Y' is selected from the group consisting of:

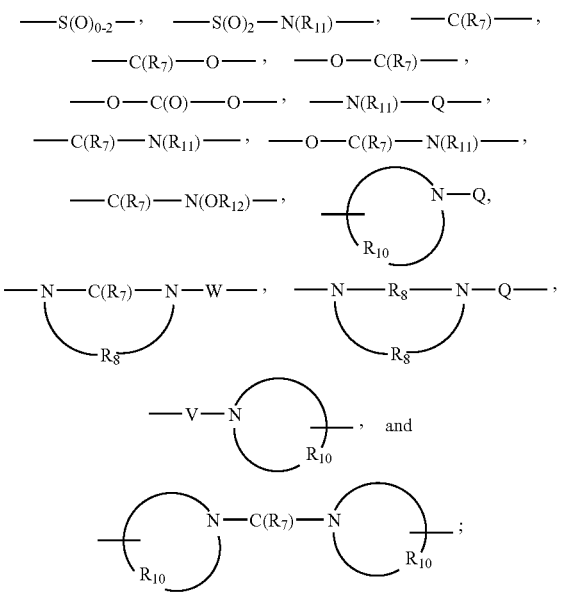

Z' is a bond or —O—;
A' is selected from the group consisting of —CH$_2$—, —O—, —C(O)—, —S(O)$_{0-2}$—, and —N(R$_4$')—;
Q is selected from the group consisting of a bond, —C(R$_7$)—, —C(R$_7$)—C(R$_7$)—, —S(O)$_2$—, —C(R$_7$)—N(R$_{11}$)—W—, —S(O)$_2$—N(R$_{11}$)—, —C(R$_7$)—O—, and —C(R$_7$)—N(OR$_{12}$)—;
V is selected from the group consisting of —C(R$_7$)—, —O—C(R$_7$)—, —N(R$_{11}$)—C(R$_7$)—, and —S(O)$_2$—;
W is selected from the group consisting of a bond, —C(O)—, and —S(O)$_2$—;
c and d are independently integers from 1 to 6 with the proviso that c+d is ≦7, and when A' is —O— or —N(R$_4$')— then c and d are independently integers from 2 to 4;
R$_6$ is selected from the group consisting of hydrogen, alkyl, and arylalkylenyl;
R$_7$ is selected from the group consisting of =O and =S;
R$_8$ is C$_{2-7}$ alkylene;
R$_9$ is selected from the group consisting of hydrogen, alkyl, and arylalkylenyl; or R$_9$ and R$_4$ together with the nitrogen atom to which R$_9$ is bonded can join to form the group

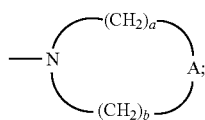

R$_{10}$ is C$_{3-8}$ alkylene;
R$_{11}$ is selected from the group consisting of hydrogen, C$_{1-10}$ alkyl, C$_{2-10}$ alkenyl, C$_{1-10}$ alkoxyC$_{2-10}$ alkylenyl, and arylC$_{1-10}$ alkylenyl; and
R$_{12}$ is selected from the group consisting of hydrogen and alkyl;
or a pharmaceutically acceptable salt thereof.

2. A compound of the following Formula IV:

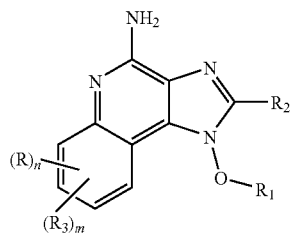

wherein:
R$_1$ is selected from the group consisting of:
—R$_4$,
—X—R$_5$,
—X—N(R$_6$)—Y—R$_4$,
—X"—C(R$_7$)—N(R$_9$)—R$_4$,
—X—O—C(R$_7$)—N(R$_6$)—R$_4$,
—X—S(O)$_2$—N(R$_6$)—R$_4$, and
—X—O—R$_4$;
R$_2$ is selected from the group consisting of:
hydrogen,
alkyl,
alkenyl,
aryl,
heteroaryl,
heterocyclyl,
alkyl-Z-alkylenyl,
aryl-Z-alkylenyl,
alkenyl-Z-alkylenyl, and
alkyl or alkenyl substituted by one or more substituents selected from the group consisting of:
hydroxy,
halogen,
—N(R$_6$)$_2$,
—C(R$_7$)—N(R$_6$)$_2$,
—S(O)$_2$—N(R$_6$)$_2$,
—N(R$_6$)—C(R$_7$)—C$_{1-10}$ alkyl,
—N(R$_6$)—S(O)$_2$—C$_{1-10}$ alkyl,
—C(O)—C$_{1-10}$ alkyl,
—C(O)—O—C$_{1-10}$ alkyl,
—N$_3$,
aryl,
heteroaryl,
heterocyclyl,
—C(O)-aryl,
—C(O)-heteroaryl,
—N(R$_6$)—C(R$_7$)-aryl,
—N(R$_6$)—S(O)$_2$-aryl,
—O—C(R$_7$)—C$_{1-10}$ alkyl,
—O—C(R$_7$)-aryl,
—O—C(R$_7$)—N(R$_6$)—C$_{1-10}$ alkyl, and
—O—C(R$_7$)—N(R$_6$)-aryl;
R is selected from the group consisting of:
halogen,
hydroxyl,
alkyl,
alkenyl,
haloalkyl,
alkoxy,
alkylthio, and
—N(R$_{12}$)$_2$;
R$_3$ is selected from the group consisting of:
-Z'R$_4$',
-Z'-X'—R$_4$',
-Z'-X'—Y'—R$_4$', and
-Z'-X'—R$_5$',
n is an integer from 0 to 4;
m is 0 or 1, with the proviso that when m is 1, n is 0, 1, or 2;
R$_4$ is selected from the group consisting of hydrogen, alkyl, alkenyl, alkynyl, aryl, arylalkylenyl, heteroaryl, and heterocyclyl wherein the alkyl, alkenyl, akynyl, aryl, arylalkylenyl, heteroaryl, and heterocyclyl groups can be unsubstituted or substituted by one or more substituents independently selected from the group consisting of alkyl, alkoxy, haloalkyl, haloalkoxy, halogen, nitro, hydroxy, mercapto, cyano, carboxy, formyl, aryl, aryloxy, arylalkoxy, heteroaryl, heteroaryloxy, heteroarylalkoxy, heterocyclyl, heterocyclylalkylenyl, amino, alkylamino, (arylalkylenyl)amino, dialkylamino, and in the case of alkyl, alkenyl, alkynyl, and heterocyclyl, oxo, with the proviso that when R$_4$ is a substituted alkyl group and the substituent contains a hetero atom which bonds directly to the alkyl group then the alkyl group contains at least two carbons between the substituent and the oxygen atom to which R$_1$ is bonded;

$R_5$ is selected from the group consisting of:

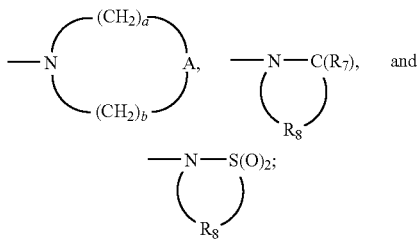

$X$ is $C_{2-20}$ alkylene;
$X''$ is $C_{1-20}$ alkylene,
$Y$ is selected from the group consisting of —$C(R_7)$—, —$C(R_7)$—$O$—, —$S(O)_2$—, —$S(O)_2$ $N(R_6)$—, and —$C(R_7)$—$N(R_9)$—;
$Z$ is selected from the group consisting of —$O$— and —$S(O)_{0-2}$—;
$A$ is selected from the group consisting of —$CH(R_6)$—, —$O$—, —$N(R_6)$—, —$N(Y—R_4)$—, and —$N(X—N(R_6)—Y—R_4)$—;
a and b are independently integers from 1 to 4 with the proviso that when $A$ is —$O$—, —$N(R_6)$—, —$N(Y—R_4)$—, or —$N(X—N(R_6)—Y—R_4)$— then a and b are independently integers from 2 to 4;
$R_4'$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
$R_5'$ is selected from the group consisting of:

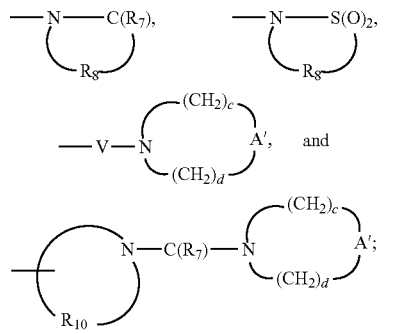

$X'$ is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene, or heterocyclylene and optionally interrupted by one or more —$O$— groups,
$Y'$ is selected from the group consisting of:

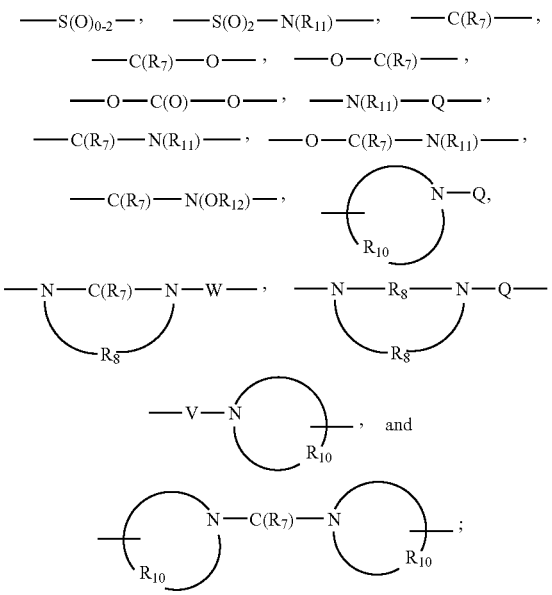

$Z'$ is a bond or —$O$—;
$A'$ is selected from the group consisting of —$CH_2$—, —$O$—, —$C(O)$—, —$S(O)_{0-2}$—, and —$N(R_4')$—;
$Q$ is selected from the group consisting of a bond, —$C(R_7)$—, —$C(R_7)$—$C(R_7)$—, —$S(O)_2$—, —$C(R_7)$—$N(R_{11})$—$W$—, —$S(O)_2$—$N(R_{11})$—, —$C(R_7)$—$O$—, and —$C(R_7)$—$N(OR_{12})$—;
$V$ is selected from the group consisting of —$C(R_7)$—, —$O$—$C(R_7)$—, —$N(R_{11})$—$C(R_7)$—, and $S(O)_2$—.
$W$ is selected from the group consisting of a bond, —$C(O)$—, and —$S(O)_2$—;
c and d are independently integers from 1 to 6 with the proviso that c+d is ≦7, and when $A'$ is —$O$— or —$N(R_4')$— then c and d are independently integers from 2 to 4;
$R_6$ is selected from the group consisting of hydrogen, alkyl, and arylalkylenyl;
$R_7$ is selected from the group consisting of =$O$ and =$S$;
$R_8$ is $C_{2-7}$ alkylene;
$R_9$ is selected from the group consisting of hydrogen, alkyl, and arylalkylenyl; or $R_9$ and $R_4$ together with the nitrogen atom to which $R_9$ is bonded can join to form the group

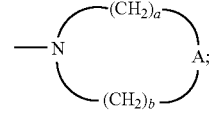

$R_{10}$ is $C_{3-8}$ alkylene;
$R_{11}$ is selected from the group consisting of hydrogen, $C_{1-10}$ alkyl, $C_{2-10}$ alkenyl, $C_{1-10}$ alkoxy$C_{2-10}$ alkylenyl, and aryl$C_{1-10}$ alkylenyl; and
$R_{12}$ is selected from the group consisting of hydrogen and alkyl;
or a pharmaceutically acceptable salt thereof.

3. The compound or salt of claim 2 wherein n is 0.

4. The compound or salt of claim 2 wherein m is 0.

5. The compound or salt of claim 1 wherein $R_2$ is selected from the group consisting of hydrogen, alkyl, hydroxyalkyl, and alkoxyalkylenyl.

6. The compound or salt of claim 1 wherein $R_2$ is selected from the group consisting of hydrogen, methyl, ethyl, n-propyl, n-butyl, methoxymethyl, ethoxymethyl, 2-methoxyethyl, hydroxymethyl, 2-hydroxyethyl, and 3-hydroxypropyl.

7. The compound or salt of claim 1 wherein $R_1$ is —$R_4$, —X—N($R_6$)—Y—$R_4$, or —X"—C($R_7$)—N($R_9$)—$R_4$.

8. The compound or salt of claim 7 wherein —$R_4$ is alkyl, aryl, or arylalkylenyl.

9. The compound or salt of claim 8 wherein $R_4$ is selected from the group consisting of hydrogen, methyl, ethyl, isopropyl, tert-butyl, isobutyl, benzyl, 2-nitrobenzyl, and 2-phenoxyethyl.

10. A pharmaceutical composition comprising a therapeutically effective amount of a compound or salt of claim 1 in combination with a pharmaceutically acceptable carrier.

11. The compound or salt of claim 2 wherein $R_2$ is selected from the group consisting of hydrogen, alkyl, hydroxyalkyl, and alkoxyalkylenyl.

12. The compound or salt of claim 2 wherein $R_2$ is selected from the group consisting of hydrogen, methyl, ethyl, n-propyl, n-butyl, methoxymethyl, ethoxymethyl, 2-methoxyethyl, hydroxymethyl, 2-hydroxyethyl, and 3-hydroxypropyl.

13. The compound or salt of claim 2 wherein $R_1$ is —$R_4$, —X—N($R_6$)—Y—$R_4$, or —X"—C($R_7$)—N($R_9$)—$R_4$.

14. The compound or salt of claim 13 wherein —$R_4$ is alkyl, aryl, or arylalkylenyl.

15. The compound or salt of claim 14 wherein $R_4$ is selected from the group consisting of hydrogen, methyl, ethyl, isopropyl, tert-butyl, isobutyl, benzyl, 2-nitrobenzyl, and 2-phenoxyethyl.

16. A pharmaceutical composition comprising a therapeutically effective amount of a compound or salt of claim 2 in combination with a pharmaceutically acceptable carrier.

* * * * *

UNITED STATES PATENT AND TRADEMARK OFFICE
CERTIFICATE OF CORRECTION

PATENT NO. : 7,579,359 B2
APPLICATION NO. : 11/574463
DATED : August 25, 2009
INVENTOR(S) : Larry R Krepski et al.

It is certified that error appears in the above-identified patent and that said Letters Patent is hereby corrected as shown below:

Page 2
Column 2 (Other Publications); Line 19, Delete "lzumi" and insert -- Izumi --, therefor.

Column 10
Line 52 (Approx.); After "—Q—" insert -- , --.

Column 11
Line 53; Delete "X $R_5$," and insert -- —X—$R_5$, --, therefor.

Column 15
Line 55 (Approx.); After "—Q—" insert -- , --.

Column 21
Line 38 (Approx.); After "—Q—" insert -- , --.

Column 30
Line 24; Delete "halo alkyl, halo alkoxy," and insert -- haloalkyl, haloalkoxy, --, therefor.

Column 51
Line 66; Delete "—C(—$NY_2$)—R'," and insert -- —C(=$NY_2$)—R', --, therefor.

Column 53
Line 58; Delete "factors" and insert -- factor-α --, therefor.

Column 58
Line 49; Delete "$C_{15}H_{18}N_4O.0.06H_2O.0.25$;" and insert -- $C_{15}H_{18}N_4O \cdot 0.06H_2O \cdot 0.25$; --, therefor.

Column 59
Line 35; Delete "$C_{13}H_{14}N_4O.0.05H_2O$:" and insert -- $C_{13}H_{14}N_4O \cdot 0.05H_2O$: --, therefor.

Signed and Sealed this
Eighth Day of February, 2011

David J. Kappos
*Director of the United States Patent and Trademark Office*

Column 60
Line 66; Delete "$C_{14}H_{16}N_4O.0.41H_2O$:" and insert -- $C_{14}H_{16}N_4O \cdot 0.41H_2O$: --, therefor.

Column 61
Line 23; Delete "$C_{12}H_{12}N_4O.0.14CH_2Cl_2$:" and insert -- $C_{12}H_{12}N_4O \cdot 0.14CH_2Cl_2$: --, therefor.
Line 43; Delete "O-isobutyllhydroxylamine" and insert -- O-isobutylhydroxylamine --, therefor.

Column 62
Line 10; Delete "$C_{13}H_{14}N_4O.0.15H_2O$:" and insert -- $C_{13}H_{14}N_4O \cdot 0.15H_2O$: --, therefor.
Line 57; Delete "$C_{17}H_{13}N_3O.0.2H_2O$:" and insert -- $C_{17}H_{13}N_3O \cdot 0.2H_2O$: --, therefor.

Column 63
Line 19; Delete "$C_{17}H_{14}N_4O.0.3H_2O$:" and insert -- $C_{17}H_{14}N_4O \cdot 0.3H_2O$: --, therefor.

Column 64
Line 22; Delete "$C_{19}H_{18}N_4O.0.3H_2O$:" and insert -- $C_{19}H_{18}N_4O \cdot 0.3H_2O$: --, therefor.

Column 66
Line 35; Delete "$C_{17}H_{20}N_4O.0.1CH_2Cl_2$:" and insert -- $C_{17}H_{20}N_4O \cdot 0.1CH_2Cl_2$: --, therefor.

Column 67
Line 41; Delete "$C_{17}H_{22}N_4O.0.3H_2O$:" and insert -- $C_{17}H_{22}N_4O \cdot 0.3H_2O$: --, therefor.

Column 70
Line 9; Delete "$C_{16}H_{12}N_4O.0.2H_2O$:" and insert -- $C_{16}H_{12}N_4O \cdot 0.2H_2O$: --, therefor.

Column 76
Line 37; Delete "$C_{13}H_{14}N_4O.0.54H_2O$:" and insert -- $C_{13}H_{14}N_4O \cdot 0.54H_2O$: --, therefor.

Column 77
Line 47; Delete "$C_{14}H_{16}N_4O.0.33H_2O$:" and insert -- $C_{14}H_{16}N_4O \cdot 0.33H_2O$: --, therefor.

Column 78
Line 27; Delete "$C_{16}H_{20}N_4O.0.24H_2O$:" and insert -- $C_{16}H_{20}N_4O \cdot 0.24H_2O$: --, therefor.

Column 80
Line 9; Delete "$C_{17}H_{22}N_4O.0.08H_2O$:" and insert -- $C_{17}H_{22}N_4O \cdot 0.08H_2O$: --, therefor.

Column 81
Line 40 (Approx.); Delete "(M+H);" and insert -- $(M+H^+)$; --, therefor.

Column 83
Line 23; Delete "$C_{19}H_{18}N_4O.0.10H_2O$:" and insert -- $C_{19}H_{18}N_4O \cdot 0.10H_2O$: --, therefor.

Column 98
Line 22 (Approx.); In Claim 1, delete "—X—$R_4$;" and insert -- —X—O—$R_4$; --, therefor.
Line 31; In Claim 1, delete "aryl Z-alkylenyl," and insert -- aryl-Z-alkylenyl, --, therefor.

Column 99
Line 17 (Approx.); In Claim 1, delete "-Z'$R_4$'," and insert -- -Z'-$R_4$', --, therefor.
Line 61; In Claim 1, delete "($R_6$) Y $R_4$) ;" and insert -- ($R_6$)—Y—$R_4$)—; --, therefor.

Column 102
Line 43 (Approx.); In Claim 2, delete "-Z'$R_4$'," and insert -- -Z'-$R_4$', --, therefor.

Column 103
Line 16 (Approx.); In Claim 2, delete "alkylene," and insert -- alkylene; --, therefor.
Line 18 (Approx.); In Claim 2, delete "—$S(O)_2$ N($R_6$)—," and insert -- —$S(O)_2$—N($R_6$)—, --, therefor.

Column 104
Line 38 (Approx.); In Claim 2, delete "$S(O)_2$—." and insert -- —$S(O)_2$—. --, therefor.